United States Patent
Gray

(10) Patent No.: US 11,696,571 B2
(45) Date of Patent: Jul. 11, 2023

(54) SYSTEMS AND METHODS FOR AUTOMATED MATURATION OF OYSTERS

(71) Applicant: HASLEA, INC., Westport, CT (US)

(72) Inventor: Luke Gray, Exeter, NH (US)

(73) Assignee: Mint Machine Technologies, Inc., Dover, DE (US)

( * ) Notice: Subject to any disclaimer, the term of this patent is extended or adjusted under 35 U.S.C. 154(b) by 0 days.

(21) Appl. No.: 17/551,801

(22) Filed: Dec. 15, 2021

(65) Prior Publication Data

US 2022/0183261 A1 Jun. 16, 2022

Related U.S. Application Data

(60) Provisional application No. 63/255,213, filed on Oct. 13, 2021, provisional application No. 63/170,565, (Continued)

(51) Int. Cl.
*A01K 61/54* (2017.01)
*A01K 61/60* (2017.01)
*A01K 67/033* (2006.01)

(52) U.S. Cl.
CPC ............. *A01K 61/54* (2017.01); *A01K 61/60* (2017.01); *A01K 67/033* (2013.01); *A01K 2227/70* (2013.01)

(58) Field of Classification Search
CPC ...... A01K 61/54; A01K 61/60; A01K 67/033; A01K 2227/70
See application file for complete search history.

(56) References Cited

U.S. PATENT DOCUMENTS 2,818,598 A * 1/1958 Skrmetta ............... A22C 29/046
452/12
5,046,411 A * 9/1991 le Grand ................ A23N 1/003
99/584
(Continued)

FOREIGN PATENT DOCUMENTS

AU 2007200790 A1 9/2007
AU 2016101044 A4 8/2016
(Continued)

OTHER PUBLICATIONS

Chesapeake Bay Oyster Company, "Quicktube Sorter," Mar. 28, 2009. Available at http://chesbayoysterco.blogspot.com/2009/03/quicktube-sorter.html (Year: 2018), retrieved on Mar. 15, 2022.
(Continued)

*Primary Examiner* — Monica L Perry
*Assistant Examiner* — Aaron M Rodziwicz
(74) *Attorney, Agent, or Firm* — Amster, Rothstein & Ebenstein LLP

(57) ABSTRACT

An automated oyster maturation system including a containment assembly rotatably disposed within a housing. The containment assembly includes a spiral construction that includes compartments that are in communication with one another, walls that define the compartments, and ramps. Openings disposed in the walls and ramps increase in size from the outer diameter to the inner diameter of the spiral construction so that, with every complete rotation of the containment assembly, every oyster will tumble further into the spiral construction and ascend from its original compartment into the adjacent inner compartment where opening size is larger than in the original compartment such that only oysters which have grown sufficiently can remain in the adjacent inner compartment while oysters that have not (Continued)

grown sufficiently yet will fall through the openings of the adjacent inner compartment into the original compartment.

26 Claims, 34 Drawing Sheets

Related U.S. Application Data filed on Apr. 5, 2021, provisional application No. 63/135,800, filed on Jan. 11, 2021, provisional application No. 63/125,971, filed on Dec. 15, 2020.

(56) References Cited

U.S. PATENT DOCUMENTS

| | | | |
|---|---|---|---|
| 6,508,699 B1 * | 1/2003 | Santoriello | A22C 29/043 452/173 |
| 8,635,730 B2 | 1/2014 | Heard | |
| 10,462,989 B2 * | 11/2019 | Oney | A01G 33/00 |
| 10,624,283 B2 * | 4/2020 | Shoham | A01G 33/00 |
| 2002/0069833 A1 | 6/2002 | Salinas | |
| 2007/0048859 A1 * | 3/2007 | Sears | C12N 1/12 435/289.1 |
| 2011/0265730 A1 | 11/2011 | Farrington | |
| 2013/0255585 A1 | 10/2013 | Hamman | |
| 2018/0213752 A1 | 8/2018 | Goudey et al. | |
| 2020/0060242 A1 * | 2/2020 | Boyle | A01K 61/54 |
| 2020/0100473 A1 | 4/2020 | Rice et al. | |
| 2020/0367476 A1 | 11/2020 | Tur Estrada et al. | |
| 2021/0000084 A1 * | 1/2021 | Sampson | A01K 61/54 |
| 2021/0352878 A1 * | 11/2021 | Llecha Galiñanes | A01K 1/01 |

FOREIGN PATENT DOCUMENTS

| | | | |
|---|---|---|---|
| CA | 2319746 A1 | 9/2001 | |
| CN | 104396835 A | 3/2015 | |
| CN | 107079861 A | 8/2017 | |
| CN | 107372260 A | 11/2017 | |
| CN | 107667997 A | 2/2018 | |
| CN | 107980685 A | 5/2018 | |
| CN | 108207727 A | 6/2018 | |
| CN | 108419747 A | 8/2018 | |
| CN | 109561668 A | 4/2019 | |
| FR | 2 850 530 B1 | 4/2005 | |
| FR | 3039747 A1 | 2/2017 | |
| JP | 2014204709 A | 10/2014 | |
| KR | 20030065118 A | 8/2003 | |
| KR | 101584527 B1 | 1/2016 | |
| KR | 101629652 B1 | 6/2016 | |
| KR | 20160107455 A | 9/2016 | |
| KR | 20200045698 A | 5/2020 | |
| WO | 1996031117 A1 | 10/1996 | |
| WO | 2018201191 A1 | 11/2018 | |
| WO | WO-2018201191 A1 * | 11/2018 | A01K 61/54 |
| WO | WO-2020246958 A1 * | 12/2020 | A22C 29/043 |

OTHER PUBLICATIONS

"Oyster Sorting Tumbler," No. 289 Hongqi road, Anping County, Hengshui City, Hebei Province, China. Available at https://www.exportersindia.com/no-289-hongqi-road-anping-county-hengshui/oyster-sorting-tumbler-hengshui-china-1383727.htm, retrieved on Mar. 15, 2022.

International Search Report issued in Counterpart PCT Application No. PCT/US2021/063522 dated Mar. 15, 2022.

Written Opinion issued in Counterpart PCT Application No. PCT/US2021/063522 dated Mar. 15, 2022.

* cited by examiner

SYSTEMS AND METHODS FOR AUTOMATED MATURATION OF OYSTERS

RELATED APPLICATIONS

This application claims priority to and the benefit of U.S. Provisional Patent Application No. 63/255,213, filed Oct. 13, 2021 and entitled SYSTEMS AND METHODS FOR AUTOMATED MATURATION OF OYSTERS, U.S. Provisional Patent Application No. 63/170,565, filed Apr. 5, 2021 and entitled AUTOMATED OYSTER MATURATION CONTAINMENT, U.S. Provisional Patent Application No. 63/135,800, filed Jan. 11, 2021 and entitled AUTOMATED OYSTER MATURATION CONTAINMENT, and U.S. Provisional Patent Application No. 63/125,971, filed Dec. 15, 2020 and entitled AUTOMATED OYSTER FARMING SYSTEM, the contents of which are incorporated herein by reference in their entirety.

FIELD OF THE INVENTION

The present invention relates to systems and methods for automated maturation of oysters.

BACKGROUND

Traditional oyster farmers rake wild oysters off the seafloor. The process is generally unsustainable and also inefficient.

Modern aquaculture farmers collect wild oyster spat (larvae that begin to attach to substrate) or buy oyster seed (when spat begin to grow shells) from hatcheries, and mature this seed using a variety of methods. Seed may be matured for, example, naturally in existing oyster beds, and/or in simple floating or bottom baskets, cages, or bags, to name a few.

Maturation of an oyster to a typical harvest size (e.g., 3" long) can take, for example, from as little as 9 months in warm water (e.g., near Virginia, Florida and Alabama, to name a few), to 12-24 months in temperate regions (e.g., near New England), to as long as 3 years in cold water (e.g., near Nova Scotia). Oysters may exhibit more consistent growth in water which is constantly warm (e.g., near Mexico), and may exhibit a pattern of hibernation and bolting (exhibiting slower and more rapid growth) in water which is less constantly warm but has high peaks of warmness (e.g., near Connecticut and other parts of New England).

In typical maturation methods, oysters are periodically removed from the water to be tumbled and sorted according to size. Tumbling is used to clean, shape, and stimulate growth while keeping oysters with other oysters of the same size in order to improve maturation rate. Allowing oysters to grow unchecked may result in substandard shapes and inconsistent meat content, which may affect the sale price of the oysters. Because larger oysters are able to pump disproportionately more water compared to smaller oysters, stocking oysters of appreciably different sizes together results in smaller oysters being outcompeted for water and nutrients.

Conventional sorting methods are tedious and expensive. Sorting oysters requires taking all oysters off lines/beds, bringing them to land-based facilities for processing manually and/or with mechanical/optical graders, and then putting them back out in the farm. As a result, oysters cannot economically be sorted more than a few times throughout their lifetime. Furthermore, because current farming methods require that oysters be handled so intensely, oysters must usually be cultivated in tidal basins or other nearshore locations, which are largely already fully utilized by farming (and other uses) and therefore have limited capacity to accommodate additional oyster growing. In many parts of the world, farm siting is further constrained by local ocean conditions, geography, and prevalence of natural disasters like algal blooms, viruses, and storms, to name a few. In general, nearshore growing conditions (e.g., turbidity, temperature, salinity, prevalence of disease, to name a few) are poor such that mortality is high, and growth is slow, compared to growing conditions exhibited in certain offshore trials. Nearshore leases may also be hard to acquire, pose an ecological risk, and have restrictions. Offshore permits cost hundreds of thousands of dollars to secure and provide no certainty. For example, even if a "federal permit" for an offshore lease is secured, a state or other local geographical area may not be obligated to allow landing of the product on their shore. Technologies and farm conditions vary so widely that optimal methods for a given farm can only be developed by costly trial and error. Oysters are often held in different containment-types during different stages of growth.

Conventional oyster tumbling sorters or oyster sorting tumblers, which often appear to be miniature versions of rock or gold trommels, are used by some oyster farms to increase throughput during sorting operations. Screw flighting and/or inclination is sometimes used to transport oysters through the rotating sorting tube as they are tumbled and exposed to openings of increasing size along the length of the straight tube. For example, Korean Patent Nos. KR101584527B1, KR101629652B1, and KR20160107455A disclose apparatuses resembling conventional tumbling sorters for temporarily sorting and/or cleaning shellfish/other small marine organisms in transient processing applications, but they do not contain the organisms during the normal course of cultivation. Korean Patent No. KR20200045698A discloses a platform whereon a conventional tumbling sorter is provided next to oyster containments, but the oyster containments are separate from the sorter. U.S. Patent Application Publication No. 20200060242A1 discloses a mechanized oyster containment, but does not provide the ability to sort oysters.

Other types of marine organisms, such as salmon and shrimp, for example, are matured on farms that include through-flow systems near/on bodies of saltwater or recirculating systems in land-locked locations, the latter usually requiring advanced filtration systems. However, such farming systems do not currently exist for oysters.

SUMMARY

High labor costs (related to oyster handling/sorting) and high overhead costs (resulting from limited farm capacities) have established oysters as one of the most luxurious proteins in the world. Accordingly, what is needed is an oyster maturation containment that is also able to sort oysters internally, without any human intervention or removal of oysters from the containment, so that such a containment could be deployed offshore or inland in great number. To date, no such containment has been conceived that meets the design challenge of being cost-effective, mass-manufacturable, reliable, and long-lived in the marine environment. To meet this need, the present invention provides an oyster maturation containment that can continuously sort oysters, thereby maximizing maturation rate and obviating the need for human intervention during maturation, which reduces costs and allows oyster farms to be moved offshore where space is more available and water quality is better. High quality oysters can thereby be grown in limitless quantities for less than the cost of beef or poultry.

An object of this invention is to provide a containment that may, for example, float, sink, pitch, and/or rotate around an axis of revolution, to name a few, via, for example, ballast tanks, water turbines, or outside mechanical manipulation by motors, to name a few.

A further object of the invention is to provide nested compartments, inside said containment, arranged around the axis of revolution, separated by walls with holes of specified size to allow oysters that are sufficiently small to fall through under gravity.

A further object of the invention is to make said holes smaller with distance from the axis of revolution such that, as the containment rotates and/or pitches, smaller oysters accumulate in outer compartments and larger oysters remain in inner compartments.

A further object of the invention is to transfer oysters from outer compartments into adjacent inner compartments so sorting can occur. This may be done with one-way valves and intermediate chambers (requiring both rotation and pitching of the containment), or with spiraling ramps (requiring only rotation of the containment).

A further object of the invention is to provide pumps and/or propellers for creating fresh, nutrient-rich water-flow through the containment.

A further object of the invention is to provide centerless rotating connections for introducing oyster seed into and extracting harvest-size oysters from the containment.

A further object of the invention is to provide screw flighting to convey oysters throughout the containment.

A further object of the invention is to make the containment very large and of a cylindrical or prismatic shape.

A further object of the invention is to deploy the containment in a floating grid.

A further object of the invention is to house the containment inside of a frame so that the containment can be easily transported and deployed as a bottom cage.

A still further object is to provide remote and/or autonomous control and monitoring of all aspects of operation of the containment.

Other and further objects will be explained hereinafter and more particularly delineated in the appended claims.

More specifically, exemplary embodiments of the present invention may include an oyster maturation containment assembly that tumbles and sorts oysters, which may provide advantages such as, for example, increased oyster maturation rate, reduced need for human intervention during maturation, and increased yield of more consistent and better-shaped oysters with higher meat-content, to name a few. By minimizing or even eliminating labor, said containment may be located offshore where, for example, growing conditions may be better, leases may be inexpensive, and growing capacity may be essentially limitless, to name a few advantages. Without being bound by theory, oyster meat can thereby be produced in mass-quantities, at net-zero emissions, at a cost much less than beef or poultry.

In embodiments, the containment assembly may be of a cylindrical or prismatic shape and may include multiple compartments, which may be revolved around an axis of revolution and separated by walls and/or ramps, which may each include holes of a specific size to allow oysters that are too small for one compartment to fall through the holes into an adjacent compartment. In embodiments, the holes may decrease in size with distance from the axis of revolution. In embodiments, the containment assembly may also include, for example, one-way valves and intermediate chambers and/or spiraling ramps connecting adjacent compartments, which may periodically transfer oysters from outer compartments into adjacent inner compartments such that oysters can be sorted as the oysters grow. In embodiments, by periodically transferring oysters from outer compartments into adjacent inner compartments, oysters may interface with increasingly large holes, with smaller oysters returning to outer compartments and larger oysters remaining in inner compartments. The largest oysters may, for example, accumulate in the innermost compartment or be conveyed into a harvest-ready hopper outside the containment, thereby reducing the difficulty of harvesting oysters. In embodiments, for example, a Multilayer Inverting Trommel ("oyster mint"), may include spiraling ramps which may run the entire length of the containment assembly, to transfer oysters from outer compartments to adjacent inner compartments with every rotation. Continuing the example, the oyster mint may sit inside a housing (e.g., a steel frame or a shipping container, to name a few) which may be easily transportable and rapidly deployed as a bottom-cage. Continuing the example, the oyster mint may include as many compartments as is necessary to separate oyster sizes with sufficient resolution. Still continuing the example, the oyster mint may also be provided with pumps and/or propellers to provide axial through-flow of water/nutrients and centerless rotating connections to transport, for example, seed oysters, harvest-size oysters, feed/water, waste, compressed air/ballast, power, telemetry, controls, to name a few, into/out of the containment. Oyster mints may be made very large (e.g., 20 feet long, 30 feet long, 40 feet long, less than 40 feet long, or more than 40 feet long) and deployed in large quantities (e.g., less than 2,000 oyster mints, at least 2,000 oyster mints, less than 4,000 oyster mints, or at least 4,000 oyster mints).

In embodiments, the automated oyster maturation system may include: a) a housing, b) a containment assembly rotatably disposed within the housing, which may include: 1) an outer cylindrical enclosure, 2) one or more sheets of material contained within the outer cylindrical enclosure arranged to form a spiral construction having an outer diameter and an inner diameter, wherein the spiral construction may include at least three turns, and the spiral construction further may include: i) a plurality of compartments that are in communication with one another, ii) a plurality of walls that define the plurality of compartments, iii) a plurality of ramps, wherein each of the plurality of ramps may be attached to a corresponding wall of the plurality of walls so as to form a plurality of pairs of walls and ramps that provide the spiral construction with a spiral shape, iv) a plurality of openings disposed in the plurality of walls and the plurality of ramps, the plurality of openings including a plurality of sets of openings with the openings within each set having diameters of a respective common size, the respective common size increasing from the outer diameter to the inner diameter of the spiral construction so that, with every complete rotation of the containment assembly, every oyster will tumble further into the spiral construction and ascend from its original compartment into the adjacent inner compartment where opening size is larger than in the original compartment such that only oysters which have grown sufficiently can remain in the adjacent inner compartment while oysters that have not grown sufficiently yet will fall through the openings of the adjacent inner compartment into the original compartment, and 3) a hollow shaft having a first end and a second end disposed within the innermost one of the plurality of compartments, wherein the first end of the hollow shaft may be configured to receive seed-oysters and wherein the hollow shaft includes a plurality of holes formed in the wall of the hollow shaft between the first end and the second end and sized to allow seed-oysters to pass therethrough, c) an inlet assembly configured to feed seed oysters into the containment assembly, wherein the inlet assembly may be operatively connected to the hollow shaft, and d) an ejection assembly configured to eject harvest-ready oysters from the innermost compartment of the plurality of compartments.

In embodiments, the housing may be a frame that supports the containment assembly.

In embodiments, the housing may be a shipping container, which supports and substantially encapsulates the containment assembly.

In embodiments, the oyster maturation system further may include at least one rotational device disposed within the housing and configured to rotate the containment assembly within the housing In embodiments, the at least one rotational device may include a motor.

In embodiments, the motor may include an electric motor.

In embodiments, the motor may include a hydraulic motor.

In embodiments, the motor may be powered by a battery.

In embodiments, the battery may be charged by a solar panel.

In embodiments, the motor may be powered by a hydraulic accumulator.

In embodiments, the hydraulic accumulator may be charged by a solar panel.

In embodiments, the motor may be powered by underwater cables configured to transmit electricity.

In embodiments, the motor may be configured to provide at least 1,000 inch-pounds of torque.

In embodiments, the motor may be configured to provide torque in the range of 30,000 inch-pounds to 100,000 inch-pounds.

In embodiments, at least 10,000 inch-pounds of torque is applied to the containment assembly.

In embodiments, torque in the range of 300,000 inch-pounds to 1,000,000 inch-pounds is applied to the containment assembly.

In embodiments, the containment assembly further may include a plurality of sprockets along the outer cylindrical enclosure and a chain operatively connected to the motor and the sprockets such that the containment assembly may be configured to rotate by the motor via the chain.

In embodiments, the chain may include stainless steel.

In embodiments, the chain may include a roller chain.

In embodiments, the chain may include a toothed belt.

In embodiments, the toothed belt may include a v-belt.

In embodiments, the toothed belt may include a cogged belt.

In embodiments, the containment assembly further may include a plurality of sprockets along the outer cylindrical enclosure and a chain operatively connected to the motor and the sprockets such that the containment assembly may be configured to rotate by the motor via the chain.

In embodiments, the sprockets may be separated from the containment assembly by washers under bolt compression.

In embodiments, the washers may include nonporous alumina ceramic material and/or plastic.

In embodiments, the containment assembly further may include a channel formed along the outer cylindrical enclosure.

In embodiments, a belt may be operatively connected to the motor and the channel such that the motor may be configured to rotate the containment assembly via the belt.

In embodiments, the belt may include a drive belt.

In embodiments, the belt may include rope.

In embodiments, the belt may include wire rope.

In embodiments, the housing may include rollers upon which the containment assembly rests.

In embodiments, the rollers may be driven by the motor.

In embodiments, the rollers may include solid, cast, polyurethane.

In embodiments, the rollers may include solid aluminum or ferrous wheels.

In embodiments, the rollers may be supported by plain bearings and axles.

In embodiments, the bearings may include non-absorptive, non-metallic, self-lubricating (dry-running) material.

In embodiments, the axles may include stainless steel.

In embodiments, the motor may include a coaxial low speed high torque motor operatively connected to the hollow shaft.

In embodiments, the coaxial low speed high torque motor may include a deep planetary gear reduction.

In embodiments, the at least one rotational device may include a ratchet and pawl.

In embodiments, the ratchet and pawl may include hydraulic cylinders.

In embodiments, the at least one rotational device may include retracting clevis pins.

In embodiments, the retracting clevis pins may include hydraulic cylinders.

In embodiments, the at least one rotational device may include a gear drive.

In embodiments, the at least one rotational device may include a direct drive.

In embodiments, the at least one rotational device may include a strand-jack.

In embodiments, the at least one rotational device may include a rail-jack.

In embodiments, the at least one rotational device may include wedging force pads.

In embodiments, the at least one rotational device may include a water turbine and a gear reduction, such that the rotational device may be configured to be driven by passive motion from currents and the ocean.

In embodiments, the at least one rotational device may include a rope and a capstan, such that the rope and capstan are configured to rotate the containment assembly.

In embodiments, the at least one rotational device may be configured to rotate the containment assembly about a central axis.

In embodiments, the at least one rotational device may be configured to rotate the containment assembly periodically.

In embodiments, the at least one rotational device may be configured to rotate the containment assembly completely at least once every 24 hours.

In embodiments, the at least one rotational device may be configured to rotate the containment assembly completely at least once every week.

In embodiments, the at least one rotational device may be configured to rotate the containment assembly completely at least once every month.

In embodiments, the at least one rotational device may be configured to rotate the containment assembly completely depending on the seasonal rate of growth of oysters which the containment assembly may be configured to hold.

In embodiments, the at least one rotational device may be configured to rotate the containment assembly completely at a rate configured to provide optimal growth for oysters which the containment assembly may be configured to hold.

In embodiments, the at least one rotational device may be configured to rotate the containment assembly aperiodically.

In embodiments, the at least one rotational device may be configured to rotate the containment assembly programmatically via a controller.

In embodiments, the controller may include a processor and memory configured to be programmed.

In embodiments, the controller may be programmed to operate the rotational device based on information from monitoring devices.

In embodiments, the at least one rotational device may be configured to rotate the containment assembly on demand after receiving an input from an external controller.

In embodiments, the external controller may be a remote control.

In embodiments, the at least one rotational device may be configured to rotate the containment assembly both clockwise and counterclockwise.

In embodiments, the at least one rotational device may be configured to rotate the containment assembly a first amount in a first direction and a second amount in a second direction.

In embodiments, the first direction may be opposite the second direction.

In embodiments, the first amount may be greater than the second amount.

In embodiments, the at least one rotational device may be further configured to dither the containment assembly within the housing.

In embodiments, the rotational device may include ballasts attached to the containment assembly.

In embodiments, the containment assembly may include a vibrator.

In embodiments, the vibrator may be configured to dither the containment assembly.

In embodiments, the outer cylindrical enclosure may include a set of openings in a wall of the outer cylindrical enclosure configured to allow water to flow through but prevent predators from entering the containment assembly and seed-oysters from exiting the containment assembly.

In embodiments, the set of openings in the wall of the outer cylindrical enclosure may be further configured to permit bio-deposits to exit the containment assembly.

In embodiments, the bio-deposits may include fecal matter.

In embodiments, the bio-deposits may include oyster shell shavings.

In embodiments, the bio-deposits may include dead oysters.

In embodiments, the dead oysters may include dead oysters ground up by rotation of the containment assembly.

In embodiments, the outer cylindrical enclosure may not include a set of openings in the wall of the outer cylindrical enclosure.

In embodiments, the containment assembly comprises at least one bulkhead configured to support the spiral construction.

In embodiments, the containment assembly comprises at least one beam configured to provide structural support to the spiral construction.

In embodiments, the spiral construction may include at least four turns.

In embodiments, the spiral construction may include at least five turns.

In embodiments, the spiral construction may include at least six turns.

In embodiments, the spiral construction may include at least seven turns.

In embodiments, the spiral construction may include a number of turns, wherein the number of turns may be configured to provide optimal oyster growth.

In embodiments, the spiral construction may be connected to an inner surface of the outer cylindrical enclosure.

In embodiments, the spiral construction may be welded to the inner surface of the outer cylindrical enclosure.

In embodiments, spacing between adjacent ones of the one or more sheets of material differ from the outer diameter to the inner diameter.

In embodiments, a thickness of the one or more sheets of material in each successive turn may be greater than that of a previous turn, from the outer diameter to the inner diameter.

In embodiments, a thickness of the one or more sheets of material may be substantially the same for each turn.

In embodiments, the one or more sheets of material may include a plurality of sheets of material.

In embodiments, the plurality of compartments may be in fluidic communication with one another.

In embodiments, an innermost one of the plurality of compartments may be configured to hold harvest-ready oysters (e.g., due to the openings being sized to retain oysters with a certain range of dimensions.)

In embodiments, an outermost one of the plurality of compartments may be configured to hold seed oysters.

In embodiments, each of the plurality of compartments is configured to be between 3 to 5 times the width of the oysters the compartment is configured to hold.

In embodiments, compartments in between an outermost one of the plurality of compartment and an innermost one of the plurality of compartments may be configured to hold oysters of increasing sizes, from a size of growth larger than seed-oysters to a size of growth smaller than harvest-ready oysters.

In embodiments, compartments in between an outermost one of the plurality of compartments and an innermost one of the plurality of compartments may be configured to be between 3 to 5 times the width of the oysters they are configured to hold.

In embodiments, each of the plurality of compartments besides the innermost one of the plurality of compartments may be configured to hold substantially a same number of oysters.

In embodiments, the outermost one of the plurality of compartments is configured to hold more oysters as compared to other compartments of the plurality of compartments.

In embodiments, the outermost one of the plurality of compartments may be configured to hold, for example, oysters from 4 to 34 mm in length, the next outermost one of the plurality of compartments may be configured to hold oysters from 34 to 51 mm in length, the next outermost one of the plurality of compartments may be configured to hold oysters from 51 to 60 mm in length, the next outermost one of the plurality of compartments may be configured to hold oysters from 60 to 69 mm in length, and the innermost one of the plurality of compartments may be configured to hold oysters from 69 to 78 mm in length.

In embodiments, each of the plurality of walls may include hollow half-cylinders.

In embodiments, each of the plurality of pairs of walls and ramps forms a corresponding turn of the at least three turns.

In embodiments, the plurality of walls and the plurality of ramps, increase in radius from the inner diameter of the spiral construction to the outer diameter of the spiral construction.

In embodiments, the plurality of pairs of walls and ramps may be arranged so that each of the plurality of walls is separated by a corresponding ramp of the plurality of ramps.

In embodiments, each of the plurality of ramps may include hollow half-cylinders.

In embodiments, the outermost ramp may be attached to an inner portion of the outer cylindrical enclosure.

In embodiments, the openings may be circular shaped.

In embodiments, the openings may be oval shaped.

In embodiments, the openings may be diamond shaped.

In embodiments, the openings may be square shaped.

In embodiments, the diameter of the openings increases from the inner to the outer end of each one of the plurality of walls.

In embodiments, the diameter of the openings increases from the inner to the outer side of each ramp.

In embodiments, the plurality of the sets of openings may include a set of openings having a common respective size of 1/16", a set of openings having a common respective size of 0.75", a set of openings having a common respective size of 1.375", a set of openings having a common respective size of 1.625", a set of openings having a common respective size of 1.875", and a set of openings having a common respective size of 2".

In embodiments, each of the plurality of ramps may include at least two of the plurality sets of openings so that each of the plurality of ramps may include openings of at least two different common sizes that increase from the outer diameter to the inner diameter of the spiral construction.

In embodiments, each of the plurality of walls may include only one set of the plurality of sets of openings so that each of the plurality of walls may include respective openings with diameters of a common size.

In embodiments, each of the plurality of ramps may include only one set of the plurality sets of openings so that each of the plurality of ramps may include respective openings with diameters of a common size.

In embodiments, each set of the plurality of sets of openings corresponds to one of the plurality of compartments so that each of the plurality of compartments may be configured to hold oysters of a corresponding size range.

In embodiments, the corresponding size range increases from the outermost compartment of the plurality of compartments to the innermost compartment of the plurality of compartments.

In embodiments, the corresponding size range may be configured to group oysters of appreciably the same size in only one corresponding compartment of the plurality of compartments.

In embodiments, the corresponding size range may be configured to promote oyster growth.

In embodiments, the corresponding size range may be configured to prevent bullying between oysters.

In embodiments, the containment assembly may be configured so that, when the containment assembly may be rotated, oysters which are smaller than the size range of the compartment holding the oysters pass through the set of openings corresponding to that compartment to other compartments surrounding that compartment.

In embodiments, the containment assembly may be configured so that, when the containment assembly may be dithered, oysters which are smaller than the size range of the compartment holding the oysters fall through the set of openings corresponding to that compartment to other compartments surrounding that compartment.

In embodiments, the containment assembly may be configured so that, when the containment assembly may be pitched, oysters which are smaller than the size range of the compartment holding the oysters fall through the set of openings corresponding to that compartment to other compartments surrounding that compartment.

In embodiments, the containment assembly may be configured so that, when the containment assembly may be rotated, oysters move towards the inner diameter from the outer diameter of the spiral construction along one of the at least three turns of the spiral.

In embodiments, the spiral construction may include aluminum.

In embodiments, the spiral construction may include plastic.

In embodiments, the plastic may include high-density polyethylene (HDPE).

In embodiments, the plastic may include marine grade plastic.

In embodiments, the plastic may include recycled material.

In embodiments, the spiral construction may include a composite material.

In embodiments, the spiral construction is pre-formed and supported by spiral pockets formed by bar stock.

In embodiments, the second end of the hollow shaft may be configured to receive seed-oysters.

In embodiments, the plurality of holes formed in the wall of the hollow shaft may be sized so that pressure loss may be distributed equally along a length of the hollow shaft and so that seed-oysters are distributed evenly along the length of the hollow shaft.

In embodiments, the size of the holes may be approximately ½" plus or minus a tolerance.

In embodiments, the size of the holes may be approximately three to five times an average diameter of seed-oysters of a species of oysters which the automated oyster maturation system may be configured to grow.

In embodiments, the plurality of holes formed in the wall of the hollow shaft may include four holes distributed every twelve inches of length of the hollow shaft.

In embodiments, the hollow shaft may be positioned along a central axis of the containment assembly.

In embodiments, the containment assembly further may include at least one monitoring device configured to receive and send information.

In embodiments, the at least one monitoring device may include at least one camera.

In embodiments, the at least one camera may be configured to capture visible light in the hopper.

In embodiments, the at least one camera may be configured to capture visible light in the containment assembly.

In embodiments, the at least one camera may be configured to capture infrared radiation in the hopper.

In embodiments, the at least one camera may be configured to capture infrared radiation in the containment assembly.

In embodiments, the at least one camera may include a security camera.

In embodiments, the at least one monitoring device may include at least one load cell.

In embodiments, the at least one load cell may be configured to measure the weight of the harvest hopper.

In embodiments, the at least one load cell may be configured to measure the weight of the containment assembly.

In embodiments, the at least one monitoring device may include a pressure gauge.

In embodiments, the at least one monitoring device may include a pitot tube.

In embodiments, the at least one monitoring device may include a force pad.

In embodiments, the force pad may include a force sense resistor.

In embodiments, the force pad may include a transducer.

In embodiments, the at least one monitoring device may include at least one anemometer.

In embodiments, the at least one monitoring device may include at least one accelerometer.

In embodiments, the at least one monitoring device may include a proximity sensor.

In embodiments, the proximity sensor may be configured to sense relative movement between the housing and settlement in a seabed.

In embodiments, the at least one monitoring device may include an encoder.

In embodiments, the encoder may be configured to reduce drift of the containment assembly relative to the housing.

In embodiments, the encoder may be configured to measure rotations.

In embodiments, the at least one monitoring device may include a light sensor.

In embodiments, the light sensor may include a spectrometer.

In embodiments, the at least one monitoring device may include at least one water quality sensor.

In embodiments, the at least one water quality sensor may be configured to measure water temperature.

In embodiments, the at least one water quality sensor may include a thermocouple.

In embodiments, the at least one water quality sensor may include a thermistor.

In embodiments, the at least one water quality sensor may be configured to measure water salinity.

In embodiments, the at least one water quality sensor may be configured to measure pH.

In embodiments, the at least one water quality sensor may be configured to measure water nutrient density.

In embodiments, the at least one water quality sensor may be configured to measure water turbidity.

In embodiments, the at least one water quality sensor may be configured to measure dissolved oxygen.

In embodiments, the at least one water quality sensor may be configured to measure dissolved carbon-dioxide In embodiments, the at least one water quality sensor may be configured to measure dissolved nitrogen.

In embodiments, the at least one water quality sensor may be configured to measure fecal coliform.

In embodiments, the at least one water quality sensor may be configured to measure chlorophyll.

In embodiments, the at least one water quality sensor may be configured to measure bacteria.

In embodiments, the at least one water quality sensor may be configured to measure Seston.

In embodiments, the at least one monitoring device may include at least one electro-chemical sensor.

In embodiments, the at least one electro-chemical sensor may be configured to measure ammonia.

In embodiments, the at least one electro-chemical sensor may be configured to measure nitrites.

In embodiments, the at least one electro-chemical sensor may be configured to measure nitrates.

In embodiments, the at least one electro-chemical sensor may be configured to measure a specific molecule.

In embodiments, the containment assembly may be configured to rotate based on information obtained or received from the at least one monitoring device.

In embodiments, the containment assembly may be configured to dither based on information obtained or received from the at least one monitoring device.

In embodiments, the containment assembly may be configured to pitch based on information obtained or received from the at least one monitoring device.

In embodiments, the containment assembly further may include a plurality of lights.

In embodiments, the plurality of lights may include a plurality of LED light strips.

In embodiments, each one of the plurality of compartments may include at least one LED light strip.

In embodiments, the plurality of lights may be configured to provide light approximating sunlight.

In embodiments, the plurality of lights may be configured to provide light in the ultra-violate wavelength.

In embodiments, the plurality of lights may be configured to provide light in the ultra-violet band.

In embodiments, the plurality of lights may be configured to receive electrical power.

In embodiments, the plurality of lights may be configured to provide illumination periodically.

In embodiments, the plurality of lights may be configured to provide illumination for 16 hours in a 24-hour period.

In embodiments, the plurality of lights may be configured to provide illumination aperiodically.

In embodiments, the plurality of lights may be configured to provide illumination in accordance with instructions received from a controller.

In embodiments, the controller may include a processor and a memory.

In embodiments, the controller may include a remote control configured for wireless communication (e.g., a remote control capable of WiFi/radio communication to send and receive data, new programs, etc.).

In embodiments, the automated oyster maturation system further may include a second inlet assembly configured to feed seed oysters into the containment assembly.

In embodiments, the housing includes an opening for the inlet assembly.

In embodiments, the inlet assembly may include an injection conduit configured to transport seed-oysters, the injection conduit comprising a first opening and a second opening.

In embodiments, the first opening of the injection conduit may be operatively connected to, and in fluidic communication with, an opening in the housing.

In embodiments, the first opening of the injection conduit may be below the water line.

In embodiments, a second opening of the injection conduit may be configured to receive seed-oysters.

In embodiments, the injection conduit may include rubber.

In embodiments, the injection conduit may include plastic.

In embodiments, the injection conduit may include a metal tube.

In embodiments, the second opening of the injection conduit may be operatively connected to and in fluidic communication with a first opening of an injection hose, wherein the injection hose may include a first opening and a second opening.

In embodiments, the first opening of the injection hose may be below the water line.

In embodiments, the second opening of the injection hose may be configured to receive seed-oysters.

In embodiments, the injection hose may include rubber.

In embodiments, the injection hose may include plastic.

In embodiments, the injection hose may include thermoset polymers.

In embodiments, the injection hose may include a layflat polyurethane hose.

In embodiments, the injection hose may include a metal pipe.

In embodiments, the inlet assembly further may include a float attached to the injection hose near the second opening of the injection hose assembly.

In embodiments, the inlet assembly further may include a funnel with a first opening and a second opening, wherein the second opening may be operatively connected to the injection hose and the first opening may be configured to receive seed oysters.

In embodiments, the funnel further may include a sump between the first and second openings and radial brushes which extend across the first opening and are configured to prevent seed-oysters from floating out of the sump.

In embodiments, the interior of the funnel may be filled with foam.

In embodiments, the inlet assembly may include a pump configured to pump seed-oysters through the inlet assembly.

In embodiments, the pump may include a titanium submersible pump with upwards of 60,000 hours of rated saltwater operation.

In embodiments, the pump may be further configured to pump nutrient-rich water through the inlet assembly and into the containment assembly.

In embodiments, the automated oyster maturation system further may include a second ejection assembly configured to eject harvest-ready oysters from the innermost compartment of the plurality of compartments.

In embodiments, the housing may include an opening for the ejection assembly.

In embodiments, the automated oyster maturation system further may include a floating hull, connected to the housing via at least one tether, wherein the floating hull may include at least one of: at least one solar panel, at least one battery, a hydraulic accumulator, a hydraulic pump, at least one programmable logic controller, comprising at least a memory and processor, a radio modem, a WiFi gateway, a telemetry device, a control device, a communication device, AIS, a security camera, and a flashing light.

In embodiments, the floating hull may be operably connected to the housing via electric cables and may be configured to provide electricity to components of the automated oyster maturation system.

In embodiments, the floating hull may be operably connected to the housing via hydraulic cables and may be configured to provide hydraulic power to components of the automated oyster maturation system.

In embodiments, the floating hull may be operably connected to the housing via communication cables and may be configured to send control instructions to components of the automated oyster maturation system.

In embodiments, the floating hull may be operably connected to the housing via communication cables and may be configured to receive information from components of the automated oyster maturation system.

In embodiments, the floating hull may be operably connected to the housing via at least one wireless communication device and may be configured to send control instructions to components of the automated oyster maturation system.

In embodiments, the floating hull may be operably connected to the housing via at least one wireless communication device and may be configured to receive information from components of the automated oyster maturation system.

In embodiments, the floating hull may be configured to send and receive information via the communication device.

In embodiments, the floating hull may be configured to send information to and receive information from cloud computing services.

In embodiments, the communication device may include a satellite uplink.

In embodiments, the at least one screw flight may be located within the innermost compartment of the plurality of compartments of the spiral construction.

In embodiments, the at least one screw flight may include two screw flights each having a handedness opposite to the other.

In embodiments, the at least one screw flight comprises a plurality of screw flights, each of the plurality of screw flights disposed within a corresponding one of the plurality of compartments.

In embodiments, the plurality of screw flights alternate handedness between the plurality of compartments.

In embodiments, the screw flight may include an auger.

In embodiments, the screw flight may be helical.

In embodiments, the screw flight may be one and a half times the diameter of the innermost one of the plurality of compartments.

In embodiments, the diameter of the innermost one of the plurality of compartments may be no greater than: $(4*N/(density*pi*1.5))^{(1/3)}$, wherein N may be the number of oysters which the automated oyster maturation system is configured to eject with each rotation of the containment assembly, and wherein the density is the density of oysters in the central compartment.

In embodiments, the automated oyster maturation system further includes a second hopper that receives harvest-ready oysters ejected from the containment assembly.

In embodiments, the second hopper may be located on the opposite side of the containment assembly as the first hopper.

In embodiments, the hopper may be configured to receive oysters from a plurality of ejection assemblies.

In embodiments, the hopper may include a vibrator.

In embodiments, the vibrator may be configured to dither the hopper.

In embodiments, the hopper may be within the housing.

In embodiments, the hopper may be connected to an end of the housing.

In embodiments, the hopper may be connected to the end of the housing via at least one lashing bar.

In embodiments, the hopper may be connected to the end of the housing via at least one hinge.

In embodiments, the material for the connection may be configured to prevent galvanic corrosion.

In embodiments, the automated oyster maturation system further may include an outlet assembly configured to eject harvest-ready oysters from the hopper.

In embodiments, the outlet assembly may include an ejection conduit with a first opening and a second opening, wherein the first opening may be configured to receive harvest-ready oysters.

In embodiments, the ejection conduit may include rubber.

In embodiments, the ejection conduit may include plastic.

In embodiments, the ejection conduit may include a metal tube.

In embodiments, the second opening of the ejection conduit may be operatively connected to and in fluidic communication with a first opening of an ejection hose, wherein the ejection hose may include the first opening and a second opening.

In embodiments, the first opening of the ejection hose may be below the water line.

In embodiments, the second opening of the ejection hose may be configured to receive seed-oysters.

In embodiments, the ejection hose may include rubber.

In embodiments, the ejection hose may include plastic.

In embodiments, the ejection hose may include a reinforced Kanaflex™ suction hose.

In embodiments, the ejection hose may include a metal pipe.

In embodiments, the ejection hose may be non-rigid.

In embodiments, the ejection hose may be substantially non-rigid.

In embodiments, the outlet assembly further may include a float.

In embodiments, the outlet assembly further may include a funnel with a third opening and a fourth opening, and wherein the third opening may be operatively connected to the injection hose and the fourth opening may be configured to receive harvest-ready oysters.

In embodiments, the interior of the funnel may be filled with foam.

In embodiments, a pump is used to pull harvest-ready oysters through the outlet assembly.

In embodiments, the pump may include a titanium submersible pump with upwards of 60,000 hours of rated saltwater operation.

In embodiments, the outlet assembly further may include an expanded flow insert near the first opening of the ejection conduit.

In embodiments, the outlet assembly further may include a male connector configured to connect with a matching female connector of a harvest vessel.

In embodiments, the automated oyster maturation system further may include a harvest vessel, wherein the harvest vessel may include i) a crane, wherein the crane may be configured to extend off the side of the harvest vessel, ii) a harvest hose operatively connected to the crane, iii) at least one seed injection hose, iv) a hopper to feed seed-oyster to the seed injection hose, v) at least one suction pump operatively connected to the harvest hose, vi) a deck hopper operatively connected to at least one suction pump, vii) a conveyor configured to facilitate oyster sorting, viii) a spillway operatively connected to the deck hopper, and ix) at least one reefer container onboard a deck of the harvest vessel.

In embodiments, the crane may be configured to rotate.

In embodiments, the crane may be configured to boom up and boom down.

In embodiments, the crane may be configured to telescope.

In embodiments, the crane may be configured to reel in and reel out wire rope.

In embodiments, the harvest hose may include a first vertical end-section and the at least one seed injection hose may include a second vertical end section.

In embodiments, the first vertical end-section may be operatively connected to the harvest hose via a 180-degree bend.

In embodiments, the first vertical end-section and the second vertical end-section may be mechanically connected via a coupler.

In embodiments, the harvest hose may include a female connector.

In embodiments, the female connector may be configured to connect to a male connector.

In embodiments, the male connector and the female connector may be configured to sync via GPS coordinates.

In embodiments, the harvest hose may include a camera configured to capture the female connecter.

In embodiments, the harvest hose may be configured to receive harvest-ready oysters which have been ejected from the containment assembly.

In embodiments, the at least one seed injection hose may be configured to inject oysters into the inlet assembly.

In embodiments, the harvest hose may be configured to feed oysters into the at least one suction pump.

In embodiments, the at least one suction pump may be configured to pump between 1800 and 5000 gallons per minute.

In embodiments, the at least one suction pump may include an industrial mining pump.

In embodiments, the at least one suction pump may include an industrial solids-handling pump.

In embodiments, the at least one suction pump may include an industrial dewatering pump.

In embodiments, the at least one suction pump may include a venturi pump.

In embodiments, the at least one suction pump may include a jet pump.

In embodiments, the at least one suction pump may include a fish pump.

In embodiments, the deck hopper may be configured to receive discharge from the at least one suction pump.

In embodiments, the conveyor may be configured to receive oysters from the deck hopper.

In embodiments, the harvest vessel may include optical compressed air graders to sort oysters on the conveyer.

In embodiments, the harvest vessel may be configured such that oysters on the conveyor may be sorted by hand.

In embodiments, the spillway may be configured to receive water discharged from the deck hopper.

In embodiments, the spillway may be configured to receive discarded oysters from the conveyer.

In embodiments, the at least one reefer container may be electrically connected to the harvest vessel.

In embodiments, the at least one reefer container may be configured to store harvest-ready oysters which were sorted on the conveyor.

In embodiments, the at least one reefer container may be configured to be loaded upon a trailer.

In embodiments, the harvest vessel may include a plurality of bow thrusters.

In embodiments, the harvest vessel may be configured to hold at least or up to 2,000,000 oysters.

In embodiments, the automated oyster maturation system may include a marine growth prevention system.

In embodiments, the marine growth prevention system may include brushes.

In embodiments, the marine growth prevention system may include scrapers.

In embodiments, the marine growth prevention system may be mounted to the housing.

In embodiments, the marine growth prevention system may include a slippery coating.

In embodiments, the slippery coating may include PTFE.

In embodiments, the automated oyster maturation system further comprises legs disposed on the housing.

In embodiments, the legs are removably attached to the housing.

In embodiments, the legs are attached to one another by a frame.

In embodiments, a bottom of the housing comprises panels.

In embodiments, the panels have a convex curvature relative to a seafloor.

In embodiments, the panels are spaced from one another.

In embodiments, the automated oyster maturation system further comprises distribution pipes extending from the hollow shaft.

In embodiments, the hollow shaft is divided into a plurality of compartments that extend along the length of the hollow shaft.

In embodiments, the hollow shaft comprises a plurality of lengthwise sections, and each of the plurality of compartments is blocked off within a respective one of the plurality of lengthwise sections, with the number of blocked off compartment increasing along the length of the hollow shaft.

In embodiments, the distribution pipes comprise a plurality of distribution pipes, and one or more of the plurality distribution pipes correspond to a respective one of the plurality of lengthwise sections of the hollow shaft.

In accordance with an exemplary embodiment of the present invention, a method of maturing oysters comprises: (A) injecting seed-oysters into a containment assembly that is rotatably disposed within a housing, the containment assembly comprising: (1) an outer cylindrical enclosure; (2) one or more sheets of material contained within the outer cylindrical enclosure and arranged to form a spiral construction having an outer diameter and an inner diameter, wherein the spiral construction comprises at least three turns, and the spiral construction further comprises: (i) a plurality of compartments that are in communication with one another; (ii) a plurality of walls that define the plurality of compartments; (iii) a plurality of ramps, wherein each of the plurality of ramps is attached to a corresponding wall of the plurality of walls so as to form a plurality of pairs of walls and ramps that provide the spiral construction with a spiral shape; (iv) a plurality of openings disposed in the plurality of walls and the plurality of ramps, the plurality of openings comprising a plurality of sets of openings with the openings within each set having diameters of a respective common size, the respective common size increasing from the outer diameter to the inner diameter of the spiral construction; and (B) rotating the containment assembly so that, with every complete rotation of the containment assembly, every oyster will tumble further into the spiral construction and ascend from its original compartment into the adjacent inner compartment where the opening size is larger than in the original compartment such that only oysters which have grown sufficiently can remain in the adjacent inner compartment while oysters that have not grown sufficiently yet will fall through the openings of the adjacent inner compartment into the original compartment.

In embodiments, the step (A) of injecting the seed-oysters comprising injecting the seed-oysters into a hollow shaft disposed within the innermost one of the plurality of compartments, wherein the hollow shaft comprises a plurality of holes formed in a wall of the hollow shaft and sized to allow seed-oysters to pass therethrough.

In embodiments, the step (A) of injecting the seed-oysters comprises injecting the seed-oysters via an inlet assembly operatively connected to the hollow shaft.

In embodiments, the method further comprises the step of ejecting harvest-ready oysters from the containment assembly from the innermost compartment of the plurality of compartments via an ejection assembly.

BRIEF DESCRIPTION OF THE DRAWINGS

The above and related objects, features and advantages of the present disclosure will be more fully understood by reference to the following detailed description of the exemplary, albeit illustrative, embodiments of the present invention when taken in conjunction with the accompanying figures, wherein:

FIG. 11C shows the flow of oysters through a containment assembly in accordance with an exemplary embodiment of the present invention.

Figure 1:
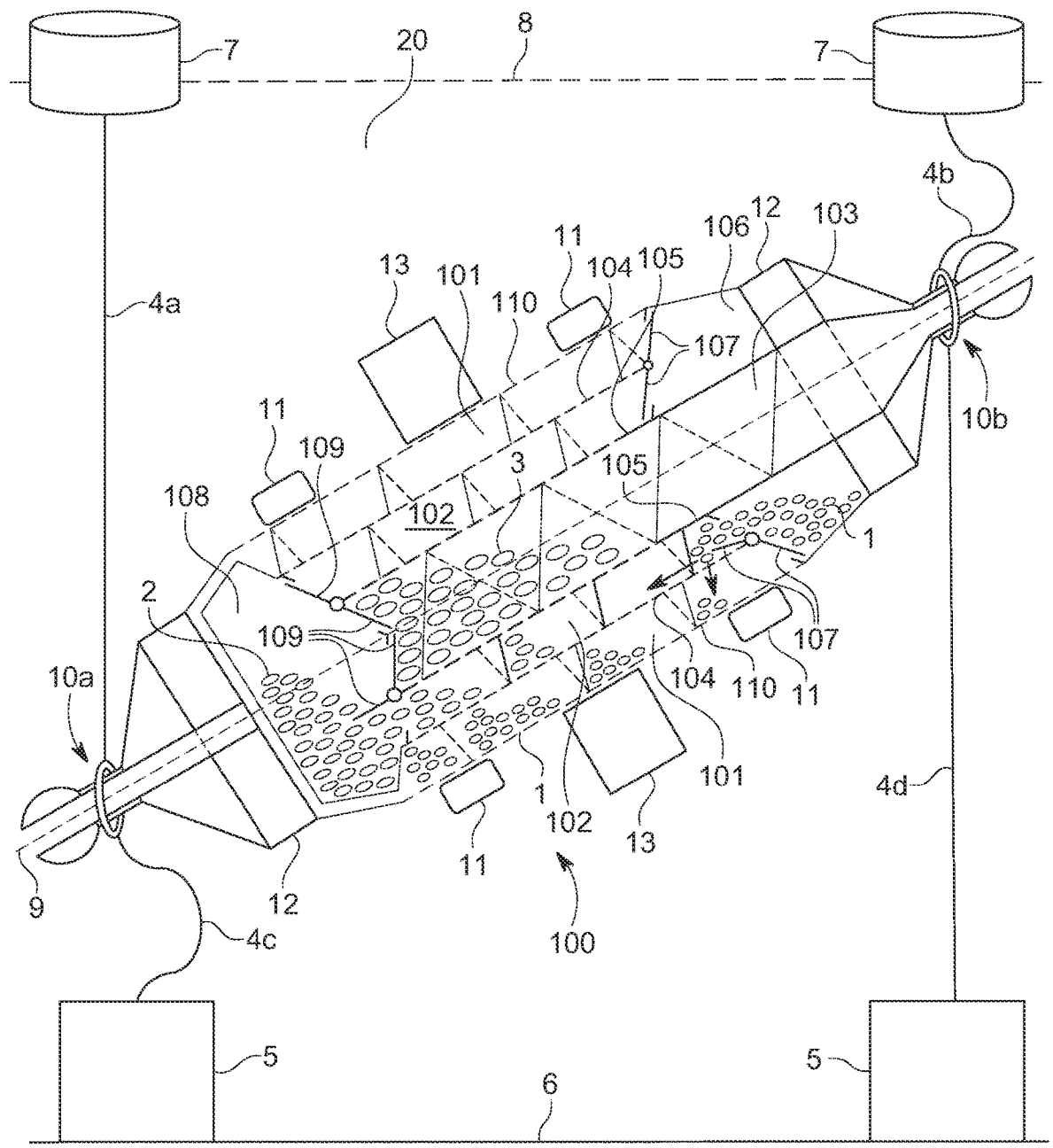
FIG. 1 is a schematic illustration depicting a cross section of an automated oyster maturation system in accordance with embodiments of the present invention.

In the drawings, exemplary embodiments of the invention are illustrated by way of example, it being expressly understood that the description and drawings are only for the purpose of illustration of exemplary embodiments and are not intended as a definition of the limits of the invention.

EXEMPLARY EMBODIMENT(S) OF THE INVENTION

As used herein, the term "automated oyster maturation system" may be used interchangeably with the terms "Multilayer Inverting Trommel" or "oyster mint" or "mint", to name a few.

FIG. 1 is a schematic illustration depicting a cross-section of an automated oyster maturation system in accordance with embodiments of the present invention. In embodiments, as shown by FIG. 1, the automated oyster maturation system may include a containment assembly 100, which may float in a body of water 20 and may contain oysters at different stages of maturation, such as, for example small oysters 1 (e.g., seed-oysters), medium oysters 2, and/or large oysters 3 (e.g., harvest-ready oysters), to name a few. In embodiments, the containment assembly 100 may be secured via tethers 4a, 4b, 4c, 4d to ballast(s) 5, which may be on a seafloor 6, and buoyancy 7, at free surface 8 (e.g., the water level). In embodiments, containment assembly 100 may also include rotating connections 10a and 10b connecting the containment assembly 100 to the tethers 4a, 4b, 4c, 4d. For example, in embodiments, rotating connection 10a may be connected to tethers 4a and 4c, and rotating connection 10b may be connected to tethers 4b and 4d. In embodiments, ballast tanks 11 may be attached to the exterior of the containment assembly. In embodiments, containment assembly 100 may be configured to move in one or more modes. For example, in embodiments, containment assembly 100 may float (e.g., via ballast tanks 11) sink (e.g., via ballast tanks 11), rotate around an axis of revolution 9 (e.g., through rotating connections 10), and/or pitch clockwise/counterclockwise in the X, Y and/or Z planes by changing ballast in ballast tanks 11 (or, for example, by changing the lengths of tethers 4a, 4b, 4c and 4d via external motors), to name a few. In embodiments, containment assembly 100 may be moved by transporting ballast to and/or from ballast tanks 11 by, for example, pushing ballast out of tanks (e.g., via air compressors) and injecting ballast into tanks (e.g., with pumps), with multiplexed valves on the discharge sides, which may enable an air compressor and/or pump to inject air and/or ballast into any ballast tank 11. In embodiments, components may be completely remotely and/or autonomously controlled. In embodiments, containment assembly 100 may include pumps 12 which may be provided to create through-flow of fresh water and nutrients in containment assembly 100. In embodiments, the direction of flow may depend on the pitch direction at any given time, such that the through-flow is upwelled from lower depths.

In embodiments, containment assembly 100 may include compartments 101, 102, 103 that may revolve around axis of revolution 9 and may be separated by perforated walls 104, 105. The compartments 101, 102, 103 may be in the shape of hollow cylinders or prisms, for example. Although the embodiment shown has only three compartments, it should be appreciated that the present invention is not limited to this number, and in other embodiments the containment assembly 100 may include any number of compartments, such as, for example, greater than three compartments, four compartments, five compartments, six compartments, etc., to name a few. In embodiments, walls 104 and 105 may include holes of specific sizes such that sufficiently small oysters can pass through to adjacent compartments. In embodiments, the size of holes may decrease with distance from the axis of revolution 9. For example, in embodiments, the holes in wall 104 may be sized to allow only small oysters 1 to pass through, whereas the holes in wall 105 may be sized to allow small oysters 1 and medium oysters 2 to pass through, and large oysters 3 may be too large to pass through the holes in either wall 104 or 105. Continuing the example, if containment assembly 100 is rotating and/or pitched, oysters may tumble inside compartments and fall through holes, accumulating in compartments with oysters of similar size, smaller oysters (e.g., small oysters 1) accumulating in outer compartments (e.g., compartment 101) and larger oysters (e.g., medium oysters 2 and/or large oysters 3) remaining in inner compartments (e.g., compartments 102 and/or 103). In embodiments, compartments 101, 102, and 103 may include screw flights (as shown), which may provide advantages such as, for example, increased path length, improved sorting efficiency, and enhanced holding capacity of the containment assembly 100, to name a few.

In embodiments, still referring to FIG. 1, compartment 101 may be connected to compartment 102 via an intermediate chamber 106 and a set of one-way valves 107, which may allow for oysters to be transported from compartment 101 to compartment 102. In embodiments, compartment 102 may be connected to compartment 103 via intermediate chamber 108 and a set of one-way valves 109, which may allow for oysters to be transported from compartment 102 to compartment 103. For example, in embodiments, if containment assembly 100 is rotated and repeatedly pitched in alternating directions, oysters from compartment 101 may flow through intermediate chamber 106 and the set of one-way valves 107 to compartment 102 and oysters from compartment 102 may flow through intermediate chamber 108 and one-way valves 109 to compartment 103. Continuing the example, in embodiments, if any oysters are too small to remain in compartments 102 or 103, they may fall through the holes in walls 104 or 105, respectively, returning to outer compartments with oysters of similar size (e.g., medium oysters 2 may return to compartment 102 and small oysters 1 may return to compartment 101). Still continuing the example, if containment assembly 100 is rotated and repeatedly pitched in alternating directions periodically (e.g., at least once every 24 hours, at least once a week, at least once a month, to name a few) oysters from outer compartments may be periodically recirculated into adjacent inner compartments and resorted into compartments with oysters of similar size.

In embodiments, oysters may grow while inside the containment assembly 100 and thus be unable to fall through holes in walls 104 or 105 of the compartments 102 and 103, respectively, of the containment assembly 100. For example, in embodiments, if a small oyster 1 becomes a medium oyster 2, it may remain in compartment 102 and may not be able to fall back into compartment 101 through the wall 104. Continuing the example, if a medium oyster 2 becomes a large oyster 3, it may remain in the innermost compartment 103 and may not be able to fall back into compartment 102 through the wall 105. Continuing the example, after a period of time (e.g., the time of growth from a small oyster 1 to large oyster 3) in the containment assembly, large oysters 3 in compartment 103 may be harvested. In embodiments, harvesting large oysters 3 from compartment 103 may be accomplished in a variety of ways, such as, for example, pumping large oysters 3 out through the centerless shaft at rotating connection 10b, temporarily removing compartment 103 and emptying large oysters 3 into a separate container for transport, opening one end and using the screw flights in compartment 103 to eject large oysters 3, and/or automatically ejecting into a secondary containment (e.g., a hopper, to name a few) with a much larger holding capacity, to name a few.

In embodiments, containment assembly 100 may include a plurality of nested compartments and intermediate chambers; for example, as many as may be necessary to separate oyster sizes with sufficient resolution so as to maximize oyster growth. Containment assembly 100 may be rotated and/or pitched on a periodic basis to optimize parameters, such as, for example, cleaning, shaping, abrading, sorting, to name a few, in order to improve oyster maturation rates and create well shaped, high-meat-content oysters. For example, the containment assembly may be rotated and/or pitched based on any suitable time period, such as, for example, on a period of any number of minutes (e.g., every 10 minutes, every 15 minutes, every 30 minutes, every 90 minutes, etc.), any number of hours (e.g., 1 hour, 5 hours, 12 hours, 24 hours, etc.), any number of days (e.g., daily, every two days, every three days, etc.), and/or any number of weeks (e.g., weekly, bi-weekly, etc.), to name a few.

In embodiments, the outermost compartment 101 may be surrounded by an outer wall 110, which may be either impervious or may include very small holes or perforations that prevent losses (e.g., seed oysters), particularly to predation. In embodiments, for example, holes in the outermost compartment 101 may be $\frac{1}{16}$ inch.

In embodiments, containment assembly 100 may include instrumentation, such as, for example, cameras, load cells, flow meters, temperature sensors, electrical conductivity/salinity sensors, to name a few, which may track oyster growing conditions and status. In embodiments, buoyancy 7 may be provided with communication equipment and energy plants such as, for example, solar panels, wave energy generators, and/or wind turbines, to name a few, for powering communication devices, measuring devices, motors, valves, and other components of the containment assembly 100. In embodiments, the automated oyster maturation system may include batteries, which may, for example, reduce intermittency in power.

Still referring to FIG. 1, in embodiments, the automated oyster maturation system may be configured to be completely or at least partially driven by tidal currents. For example, in embodiments where the automated oyster maturation system is located in areas where tidal currents are reversing (e.g., where the flood and ebb current are in approximately opposite directions)—drag on containment assembly 100 may cause it to sway and the fixed lengths of tethers 4a and 4b may cause it to pitch. Continuing the example, the shifting weight of any oysters contained in the containment assembly 100 may contribute to changing the pitch of the containment assembly 100. Continuing the example, in embodiments, a turbine 13 may be attached to the exterior of the containment assembly 100 and may be configured to provide rotation about the axis of revolution 9. In embodiments, the turbine 12 may turn the containment assembly 100 in a direction synchronized with the pitch for a given current direction (e.g., a first direction for the flood current and a second direction for the ebb current). Continuing the example, in embodiments, pumps 12 may be static propellers that provide through-flow if the containment assembly 100 rotates in tidal currents, and screw flights inside compartments 101, 102, and 103 may also be configured to provide some through-flow if the containment assembly 100 rotates.

Figure 2:
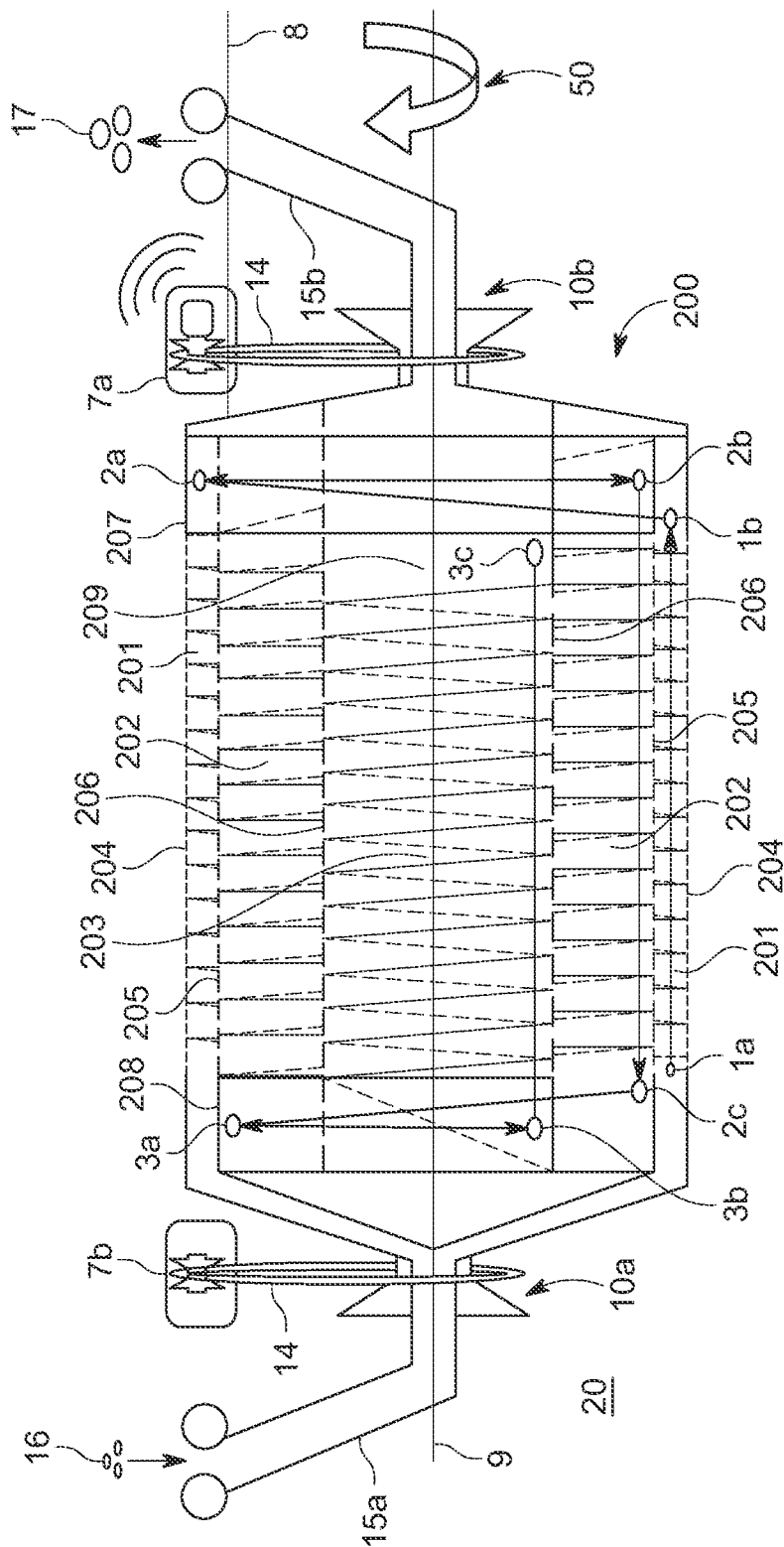
FIG. 2 is a schematic illustration depicting a cross section of an automated oyster maturation system in accordance with embodiments of the present invention.

FIG. 2 is a schematic illustration depicting a cross section of an automated oyster maturation system in accordance with embodiments of the present invention. In embodiments, the automated oyster maturation system may include containment assembly 200, which may float in a body of water 20 and may contain oysters at different stages of maturation, for example small oysters 1 (e.g., seed-oysters), medium oysters 2, and/or large oysters 3 (e.g., harvest-ready oysters), to name a few. In embodiments, the automated oyster maturation system may include buoyancy 7a, 7b and rotating belts 14a, 14b, and containment assembly 200 may be secured via the rotating belts 14a, 14b to buoyancy 7a, 7b at free surface 8. In embodiments, containment assembly 200 may rotate around axis of revolution 9 through rotating connections, for example, via motors 10a, 10b housed in buoyancy 7a, 7b (which may apply a torque on rotating belts 14a, 14b) and a follower bearing in buoyancy 7a, 7b. In embodiments, rotation speed may be controlled, for example, by remote and/or autonomous control of the motors, to name a few. As shown in FIG. 2, in embodiments, containment assembly 200 may be partially above the free surface 8. In other embodiments, containment assembly 200 resides below the free surface 8 (e.g., by an arbitrary distance) or is configured for operation both below the surface and at least partially above the surface.

In embodiments, containment assembly 200 may include multiple coaxial, cylindrical compartments 201, 202, and 203 that may revolve around an axis of revolution 9 and may be separated by perforated walls 205 and 206. Although the embodiment shown has only three compartments, it should be appreciated that the present invention is not limited to this number, and in other embodiments the containment assembly 200 may include any number of compartments, such as, for example, greater than three compartments, four compartments, five compartments, six compartments, etc., to name a few. In embodiments, walls 204 and 205 may have holes of specific sizes such that sufficiently small oysters can pass through to adjacent compartment. In embodiments, containment assembly 200 may be surrounded by outer wall 204, which may, for example, be impervious or may contain very small holes/perforations to prevent loss of seed oysters, particularly to predation. In embodiments, the size of holes may decrease with distance from the axis of revolution 9 and may vary along the length of the containment assembly. For example, holes in wall 205 may be sized to allow only small oysters 1 (e.g., seed oysters, to name a few) to pass through, whereas holes in wall 206 may be sized to allow small oysters 1 and medium oysters 2 to pass through, and large oysters 3 (e.g., harvest-ready oysters) may be too large to pass through the holes in either wall. In embodiments, if containment 200 is rotating, oysters may tumble inside compartments and fall through holes, accumulating in compartments with oysters of similar size, smaller oysters (e.g., small oysters 1) accumulating in outer compartments (e.g., compartment 201) and larger oysters (e.g., medium oyster 2 and/or large oysters 3) remaining in inner compartments (e.g., compartment 202 and/or compartment 203).

In embodiments, compartments 201, 202, 203 may include screw flights, which may be configured to convey oysters along the length of the respective compartments. In embodiments, screw flights may alternate chirality/handedness from compartment to compartment such that oysters are conveyed in opposite directions or screw flights may have the same chirality/handedness such that oysters are conveyed in the same direction through the compartments. For example, in embodiments, compartments 201 and 203 may contain right-handed screw flights and compartment 202 may contain left-handed screw flights. Continuing the example, the screw flights may be configured such that if the containment assembly 200 rotates in the indicated direction about axis of revolution 9, oysters in compartments 201 and 203 may be conveyed to the right and oysters in compartment 202 may be conveyed to the left. In embodiments, screws flights may include, for example variable pitch, variable diameter, flight geometry/profile, to name a few. In embodiments, screw flights may change with each compartment and/or vary along the length of each compartment. In embodiments, pitch and gap size may also be varied along the length of each compartment (e.g., to accommodate for increases in size as oysters grow or to increase conveyance speed in sections of a compartment, to name a few). In embodiments, screw flights may also be provided as multiple nested helices. In embodiments, the length of containment 200, the pitch of screw flights, the speed of rotation, and the number of compartments, may be configured to optimize, for example, residence time (e.g., the time spent by an oyster in the containment assembly 200), sorting frequency/efficiency, and/or holding capacity, to name a few.

In embodiments, it should be appreciated that any component of containment assembly 100 may be applied to containment assembly 200, and vice versa, without departing from the scope and spirit of the present invention. For example, as with containment assembly 100, containment assembly 200 may have centerless rotating connections 10.

Still referring to FIG. 2, a single oyster is used to illustrate the potential flow of many oysters through containment assembly 200. In embodiments, for example, an inlet 15a may introduce an oyster (e.g., one of a plurality of seed oysters 16) into containment assembly 200 so that the oyster falls to position 1a within the outermost compartment 201. Continuing the example, in embodiments, right-screw flights may convey the oyster, through compartment 201 from position 1a to position 1b. In embodiments, the screw flights may convey the oyster periodically (e.g., upon rotation of containment assembly 200). Continuing the example, the oyster may then enter spiral ramp 207 at position 2a and spiral ramp 207 may transfer the oyster into compartment 202 at position 2b. In embodiments, spiral ramp 207 may transfer the oyster as it rotates (e.g., upon rotation of containment assembly 200). Continuing the example, in embodiments, left-handed screw flights may convey the oyster through compartment 202 from position 2b to position 2c. Continuing the example, the oyster may then enter spiral ramp 208 at position 3a and spiral ramp 208 may transfer the oyster into compartment 203 at position 3b. In embodiments, spiral ramp 208 may transfer the oyster as it rotates (e.g., upon rotation of containment assembly 200). Continuing the example, in embodiments, the right-handed screw flight may transfer the oyster to position 3c in holding chamber 209 (e.g., upon rotation of containment assembly 200). Continuing the example, the oyster (e.g., now one of a plurality of harvest-ready oysters 17) may be extracted through outlet 15b.

Still referring to FIG. 2, and continuing the example, in embodiments, the holes may be sized such that, upon transfer from one compartment to another, if the oyster is too small to remain in compartments 202 or 203, the oyster may fall through the holes in walls 205 or 206, respectively, returning to outer compartments with oysters of similar size. In embodiments, the compartments may be configured so that oysters which grow more slowly may be "held back" whereas oysters that grow faster may be conducted into increasingly inner compartments. In embodiments, the containment assembly 200 may be configured such that an oyster may remain with oysters of approximately the same size and harvest-size oysters accumulate in holding chamber 209. In embodiments, the size resolution of oysters within each compartment may vary depending on the sorting efficiency and the number of compartments. In embodiments, rather than accumulating in holding chamber 209, harvest-ready oysters may be continuously ejected into a secondary storage compartment.

In embodiments, containment assembly 200 may receive pumped through-flow via inlet 15a or outlet 15b. As described previously with reference to the embodiments shown in FIG. 1, containment assembly 200 may include pumps and/or propellers that provide through-flow into one or both ends. Also as described previously with reference to the embodiment shown in FIG. 1, rotation of containment 200 may be at least partially caused by currents and/or via a turbine. In embodiments, the rotation of containment assembly 200 may be caused by a Wells turbine, which is a one-way turbine that could provide constant rotational direction regardless of the direction of current. In embodiments, the turbine may have free-swiveling turbine blades such that any current direction will turn the turbine in the same direction and enable a high angle of attack for both current directions.

Figure 3:
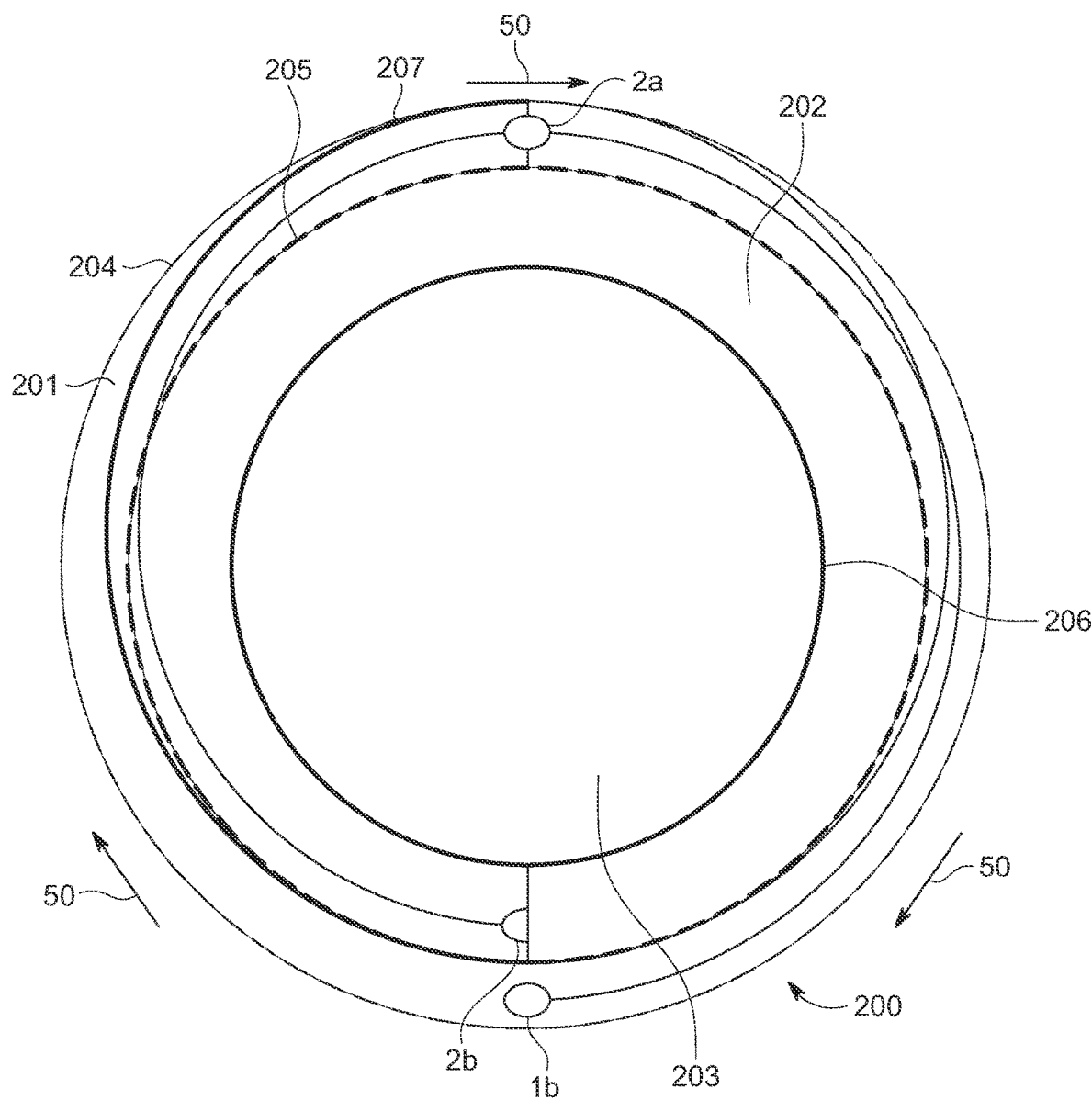
FIG. 3 is a schematic illustration of an end-view of a spiraling ramp in accordance with embodiments of the present invention.

FIG. 3 is a schematic illustration of an end-view of a spiraling ramp of the containment assembly 200 in accordance with embodiments of the present invention. In embodiments, the spiraling is configured such that if containment 200 rotates in the indicated direction, the oyster at position 1b may enter spiraling ramp 207 after tumbling inside compartment 201 along the face of the right-handed auger until it reached position 2a. In embodiments, the spiral ramp may be configured to allow an oyster to tumble down internally spiraling ramp 207 to position 2b, where an oyster may enter the left-handed auger inside compartment 202.

Figure 4:
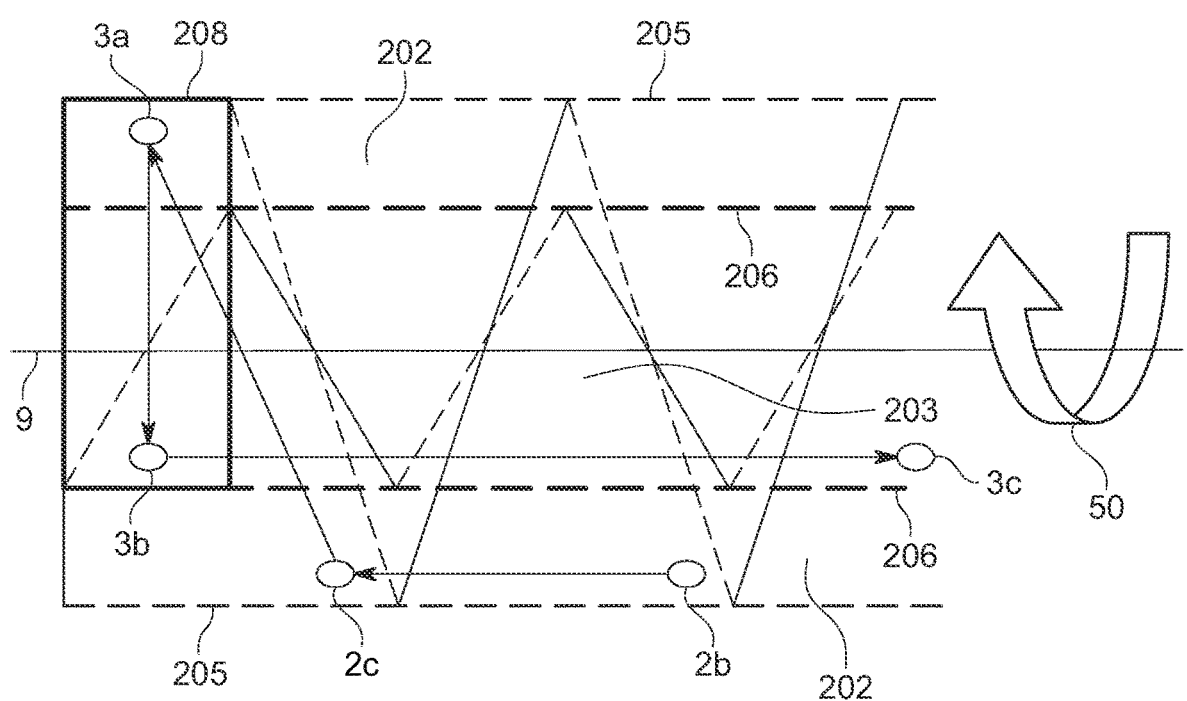
FIG. 4 is a schematic illustration of a side-view of a spiraling ramp in accordance with embodiments of the present invention.

FIG. 4 is a schematic illustration of a side-view of a spiraling ramp of the containment assembly 200 in accordance with embodiments of the present invention. FIG. 4 shows a close-up, side-view of the spiraling ramp 208 of containment 200. The oyster is conveyed by the left-handed auger inside compartment 202 from position 2b to position 2c and enters spiraling ramp 208 at position 3a. The oyster is then transferred into compartment 203 at position 3b and is conveyed through compartment 203 by the right-handed auger to position 3c.

Figure 5:
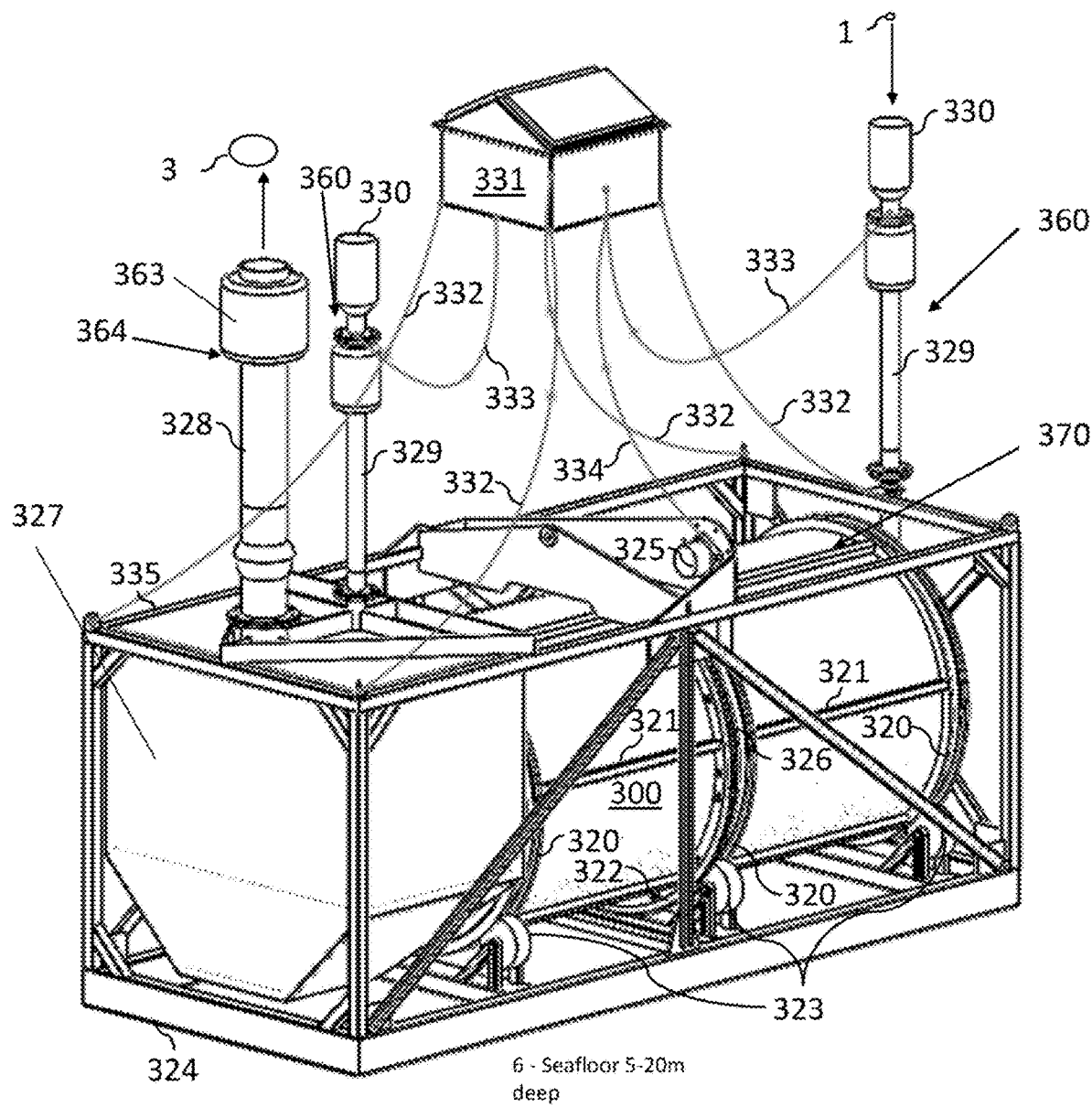
FIG. 5 is a schematic illustration of an automated oyster maturation system in accordance with exemplary embodiments of the present invention.

FIG. 5 is a schematic illustration of an automated oyster maturation system in accordance with exemplary embodiments of the present invention. In embodiments, the automated oyster maturation system includes a containment assembly 300 rotatably disposed within a housing 324. In embodiments, the housing 324 may have an open or closed frame structure. In embodiments, the housing 324 may be easily transportable and rapidly deployed as a bottom cage (for example, via a "pick and place" operation carried out by a crane and winch system attached to a ship).

In embodiments, the oyster maturation system includes at least one rotational device 325 disposed within the housing 324 and configured to rotate the containment assembly 300 within the housing 324. In embodiments, the rotational device 325 is a motor. The motor may be any suitable motor, such as, for example, an electric motor, a hydraulic motor, a battery-powered motor, a motor powered by a hydraulic accumulator, and/or a solar-powered motor (e.g., in the case of a battery-powered battery, the battery may be solar-powered, or, in the case of a motor powered by a hydraulic accumulator, the hydraulic accumulator may be solar-powered), to name few. In embodiments, the motor is configured to generate a suitable amount of torque, such as, for example, at least 1,000 inch-pounds of torque, or torque within a range of 30,000 to 100,000 inch-pounds. In embodiments, the amount of torque applied to the containment assembly may be at least 10,000 inch-pounds, or within a range of 250,000 to 1,000,000 inch-pounds.

In embodiments, the containment assembly 300 includes a power transfer mechanism 326 that transmits power from the motor to the containment assembly 300 to cause the containment assembly 300 to rotate. The containment assembly 300 may include at least one flange 322 that holds the power transfer mechanism 326 so that movement of the power transfer mechanism within the flange 322 causes the containment assembly 326 to rotate.

In embodiments, the power transfer mechanism 326 may be a roller chain drive, including a chain operatively connected to both a sprocket of the motor and a sprocket disposed within the flange 322 such that the containment assembly 300 is configured to rotate by the motor via the chain. The chain may be any type of chain that is able to transmit power generated by the motor to the sprocket to cause the containment assembly 300 to rotate. For example, the chain may be a stainless-steel chain, a roller chain, a toothed belt, a v-belt, or a cogged belt, to name a few. In embodiments, the sprockets may be separated from the containment assembly by washers under bolt compression to isolate the sprocket from the flange 322, and the washers may be made of materials such as, for example, plastic, composite and ceramic, to name a few.

In embodiments, the power transfer mechanism 326 may be a belt drive, including a belt operatively connected to the motor and which wraps around the containment assembly 300 on the flange 322 such that the containment assembly 300 is configured to rotate by the motor via the belt. The belt may be any type of belt that is able to transmit power generated by the motor to cause the containment assembly 300 to rotate. For example, the belt may be a drive belt (e.g., flat, vee, grooved, cogged, round), chain link, a rope, or a wire rope, to name a few.

It should be appreciated that the present invention is not limited to the use of any specific type of power transfer mechanism 326, and other embodiments may involve the use of other types of power transfer mechanisms such as, for example, direct drives, drive wheels, pistons, drive shafts, gears, or cogs, to name a few, without departing from the spirit and scope of the present invention.

In embodiments, the housing may include rollers 323 upon which the containment assembly 300 is able to rotate. The rollers 323 may be driven by the motor. The rollers 323 may be made of materials such as, for example, polyurethane or aluminum, to name a few. In embodiments, the rollers 323 may be made of a single material or may include a metal core with a rubber tread. The rollers 323 may be supported by plain bearings and axles. In embodiments, the bearings may include non-absorptive, chemical/saltwater resistant, non-metallic, dry-running material and the axles may be made of, for example, stainless steel, composite or other materials, to name a few.

In embodiments, the rotational device 325 may include a coaxial low-speed, high-torque motor operatively connected to a portion of the containment assembly 300, such as, for example, to a hollow shaft that extends through the containment assembly 300 (as described in more detail below). The coaxial low-speed high-torque motor may include a deep planetary gear reduction.

In embodiments, the rotational device 325 may include a ratchet and pawl. The ratchet and pawl may include hydraulic cylinders.

In embodiments, the at least one rotational device 325 may include components, such as, for example, retracting clevis pins, a gear drive, a direct drive, a strand-jack, a rail-jack, wedging force pads, a water turbine and a gear reduction (such that the rotational device is configured to be driven by passive motion from currents and the ocean), and/or a rope and a capstan (such that the rope and capstan are configured to rotate the containment assembly 300), to name a few.

In embodiments, the at least one rotational device 325 is configured to rotate the containment assembly 300 about a central axis 9, preferably on a periodic basis. For example, the containment assembly may be rotated based on any suitable time period, such as, for example, on a period of any number of minutes (e.g., every 10 minutes, every 15 minutes, every 30 minutes, every 90 minutes, etc.), any number of hours (e.g., 1 hour, 5 hours, 12 hours, 24 hours, etc.), any number of days (e.g., daily, every two days, every three days, etc.), any number of weeks (e.g., weekly, bi-weekly, etc.), to name a few. In embodiments, the rotational device 325 may be configured to rotate the containment assembly 300 completely at least once every 24 hours, completely at least once every week, completely at least once every month, completely depending on the seasonal rate of growth of oysters which the containment assembly 300 is configured to hold, completely at a rate configured to provide optimal growth for oysters which the containment assembly 300 is configured to hold, to name a few. In embodiments, the rotational device 325 may be configured to rotate the containment assembly 300 aperiodically.

In embodiments, the at least one rotational device 325 is configured to rotate the containment assembly 300 programmatically via a controller. The controller may include a processor and a non-transitory computer readable medium (e.g., a memory device) configured to be programmed with instructions that, when executed by the processor, cause the controller to rotate the containment assembly 300 by actuating the rotational device 325. The controller may be programmed to operate the rotational device based on information from a monitoring device. In embodiments, the monitoring device may monitor variables such as, for example, time, temperature, and/or water flow speed, to name a few.

In embodiments, the at least one rotational device 325 may be configured to rotate the containment assembly 300 on demand after receiving an input from an external controller. The external controller may be a remote control, such as a programmable logic controller.

In embodiments, the at least one rotational device 325 may be configured to rotate the containment assembly 300 both clockwise and counterclockwise on a periodic or aperiodic basis. For example, the rotational device 325 may be configured to rotate the containment assembly 300 a first amount in a first direction and a second amount in a second direction, where the first and second amounts may be the same or different (e.g., greater or less than one another) and where the first and second directions may be the same or different (e.g., opposite from one another). In embodiments, the at least one rotational device 325 may be configured to dither the containment assembly 300 within the housing 324.

In embodiments, the oyster maturation system may include a pitch device disposed within the housing 324 that is configured to agitate the containment assembly 300 so as to cause oysters within the cylindrical assembly 300 to shift positions. The pitch device may include, for example, ballasts 11 attached to the containment assembly 300.

Figure 6A:
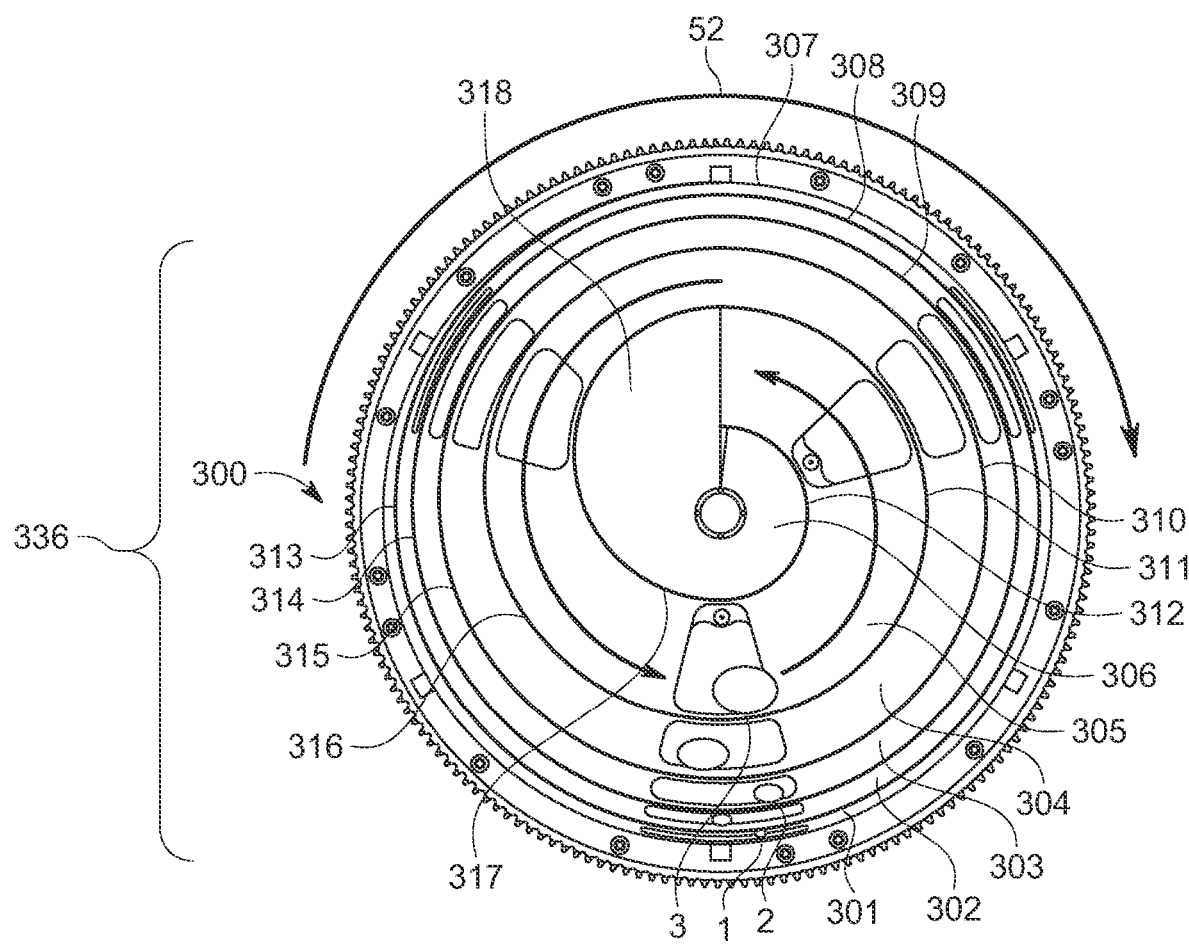
FIGS. 6A and 6B are schematic illustrations depicting a cross-section of the containment assembly 300 in accordance with an exemplary embodiment of the present invention.
Figure 6B:
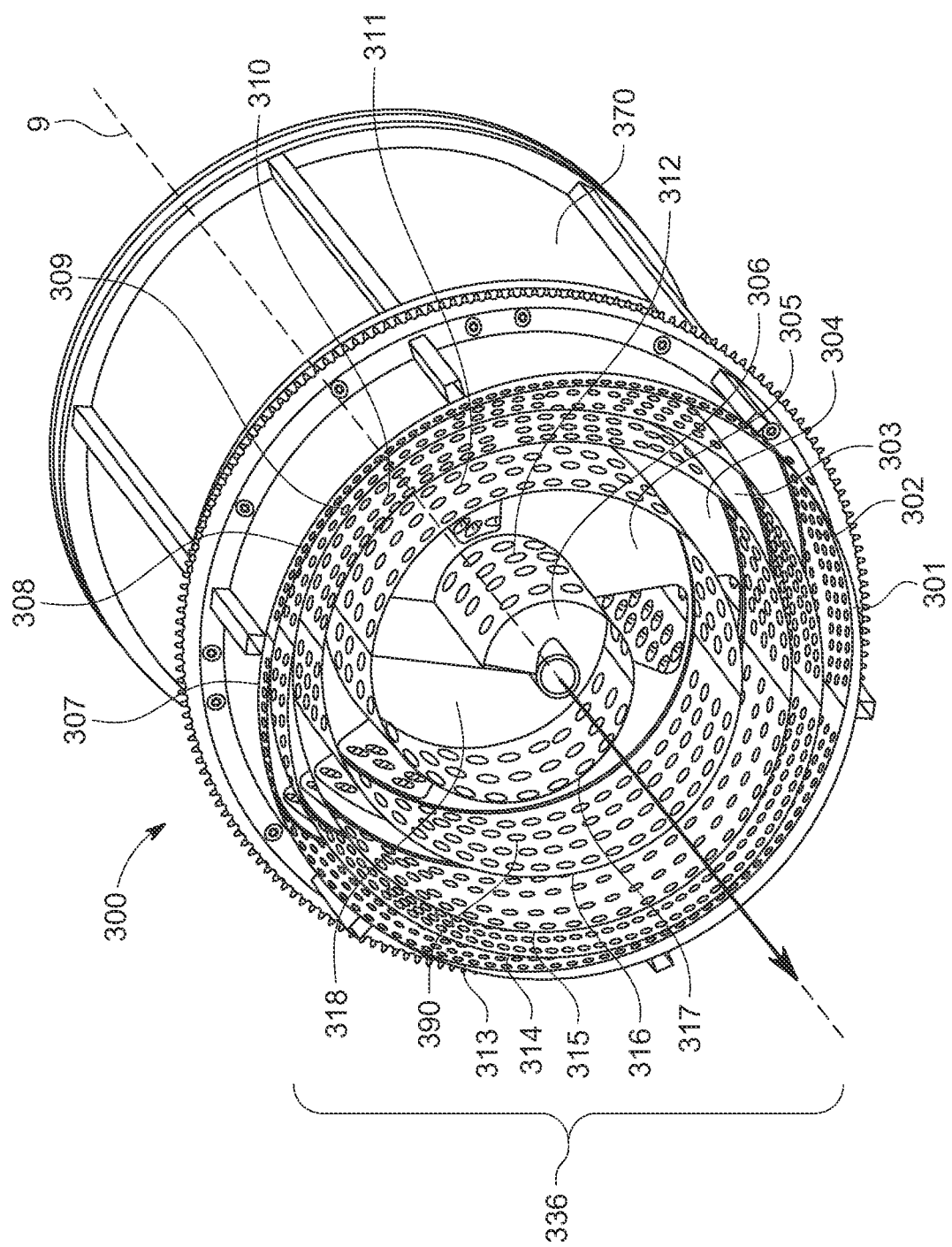

FIGS. 6A and 6B are schematic illustrations depicting a cross-section of the containment assembly 300 in accordance with an exemplary embodiment of the present invention. The containment assembly 300 includes an outer cylindrical enclosure 370 and one or more sheets of material contained within the outer cylindrical enclosure 370 arranged to form a spiral construction 336 having an outer diameter and an inner diameter. In embodiments, the spiral construction 336 may be connected to an inner surface of the outer cylindrical enclosure 370 by, for example, welding. The spiral construction 336 may be made of materials, such as, for example, metal, plastic, composite material, or combinations thereof, to name a few. In the case of plastic, the plastic may be high-density polyethylene (HDPE), marine grade plastic, or recycled plastic, to name a few. In embodiments, the spiral construction 336 may be shaped by spiraling pockets formed by bar stock.

In embodiments, the spiral construction 336 may include at least three turns, such as, for example, three turns, four turns, five turns, six turns, seven turns, to name a few. A thickness of the one or more sheets of material in each successive turn may be substantially the same or may be greater than that of a previous turn, from the outer diameter to the inner diameter of the spiral construction. In embodiments, the one or more sheets of material may include a plurality of sheets of material that are combined together to form a unitary structure.

In embodiments, the outer cylindrical enclosure 370 may include a plurality of openings configured to allow water to flow through but prevent predators from entering the containment assembly and seed-oysters from exiting the containment assembly. The openings in the outer cylindrical enclosure 370 may be further configured to permit biodeposits, such as, for example, fecal matter, oyster shell shavings, and dead oysters, to name a few, to exit the containment assembly 300. The containment assembly 300 may include one or more bulkheads 320 and beams 321 for structural support of the spiral construction 336.

In embodiments, the spiral construction 336 includes a plurality of compartments 301, 302, 303, 304, 305, 306 that are in communication with one another, a plurality of walls 308, 309, 310, 311, 312 that define the plurality of compartments 301, 302, 303, 304, 305, 306, and a plurality of ramps 313, 314, 315, 316, 317. Each of the plurality of ramps is attached to a corresponding wall of the plurality of walls 308, 309, 310, 311, 312 so as to form a plurality of pairs of walls and ramps that provide the spiral construction 336 with a spiral shape. Each of the plurality of pairs of walls 308, 309, 310, 311, 312 and ramps 313, 314, 315, 316, 317 may form a corresponding turn of the spiral construction 336. The plurality of walls 308, 309, 310, 311, 312 and the plurality of ramps 313, 314, 315, 316, 317 increase in radius from the inner diameter of the spiral construction 336 to the outer diameter of the spiral construction 336. In embodiments, the plurality of pairs of walls and ramps are arranged so that each of the plurality of walls 308, 309, 310, 311, 312 is separated by a corresponding ramp of the plurality of ramps 313, 314, 315, 316, 317. Each of the plurality of ramps may be made up of hollow half-cylinders or thin-walled half-pipes. The outermost ramp may be attached to an inner portion of the outer cylindrical enclosure. In embodiments, the plurality of walls 308, 309, 310, 311, 312 and ramps 313, 314, 315, 316, 317 may form 180 degree circular arcs. The plurality of walls 308, 309, 310, 311, 312 and ramps 313, 314, 315, 316, 317 may have constant curvature or non-constant curvature. The plurality of walls 308, 309, 310, 311, 312 and ramps 313, 314, 315, 316, 317 may be made of a perforated sheet, rolled into the proper shape and welded into a continuous spiral between bulkheads 320 and/or other support structures. In embodiments, the sheets may be made of plastic and supported by metal (e.g., aluminum) bulkheads instead of being welded together.

An innermost one 306 of the plurality of compartments is configured to hold harvest-ready oysters, and an outermost one 301 of the plurality of compartments is configured to hold seed oysters. Compartments in between an outermost one 301 of the plurality of compartment and an innermost one 306 of the plurality of compartments are configured to hold oysters of increasing sizes, from a size of growth larger than seed-oysters to a size of growth smaller than harvest-ready oysters. In embodiments, each of the plurality of compartments 301, 302, 303, 304, 305, 306 may be sized to hold oysters between 3 to 5 times the width of oysters that the compartment is configured to hold. In embodiments, each of the plurality of compartments 301, 302, 303, 304, 305 besides the innermost one 306 of the plurality of compartments may be configured to hold substantially the same number of oysters and each oyster is held for substantially the same amount of time in each compartment. For example, the sizes of the compartments may be selected so that every oyster spends approximately $\frac{1}{5}^{th}$ of its life in each compartment. In embodiments, the outermost compartment may be configured to hold more oysters than the other compartments because the seed oysters in that compartment are expected to experience a certain mortality (e.g., a mortality of at least 10%).

In embodiments, the outermost one 301 of the plurality of compartments may be configured to hold oysters from 3 mm to 34 mm in length, the next outermost one 302 of the plurality of compartments may be configured to hold oysters from 34 mm to 51 mm in length, the next outermost one 303 of the plurality of compartments may be configured to hold oysters from 51 mm to 60 mm in length, the next outermost one 305 of the plurality of compartments may be configured to hold oysters from 60 mm to 69 mm in length, and the innermost one 306 of the plurality of compartments may be configured to hold oysters from 69 mm to 78 mm in length. It should be appreciated that the size range of oysters held in each compartment is not limited to these dimensions, and the dimensions may be varied without departing from the spirit and scope of the invention.

In embodiments, a plurality of openings 390 are disposed in the plurality of walls 308, 309, 310, 311, 312 and the plurality of ramps 313, 314, 315, 316, 317. The plurality of openings 390 include a plurality of sets of openings 390 with the openings within each set having diameters of a respective common size, with the respective common size increasing from the outer diameter to the inner diameter of the spiral construction 336. In embodiments, each ramp/wall pair that defines a corresponding compartment has openings of a respective common size. In other embodiments, the diameters of the holes 390 may increase from an outermost end to an innermost end of each wall 308, 309, 310, 311, 312 and from an outermost end to an innermost end of each ramp 313, 314, 315, 316, 317. The diameter sizes of the openings 390 increase from the outermost compartment to the innermost compartment so that, with every complete rotation of the containment assembly, every oyster will tumble further into the spiral construction and ascend from its original compartment into the adjacent inner compartment where opening size is larger than in the original compartment such that only oysters which have grown sufficiently can remain in the adjacent inner compartment while oysters that have not grown sufficiently yet will fall through the openings of the adjacent inner compartment into the original compartment. This happens simultaneously for all oysters of all sizes in all compartments. Only harvest-size oysters will be able to remain in the innermost compartment. In embodiments, the openings 390 may have shapes such as, for example, circular, oval, diamond, and square, to name a few.

In embodiments, the plurality of the sets of openings 390 may include a set of openings having a common respective size of 1/16", a set of openings having a common respective size of 0.75", a set of openings having a common respective size of 1.375", a set of openings having a common respective size of 1.625", a set of openings having a common respective size of 1.875", and a set of openings having a common respective size of 2". It should be appreciated that these dimensions may be varied without departing from the spirit and scope of the invention.

In embodiments, each of the plurality of ramps 313, 314, 315, 316, 317 may include only one set of the plurality sets of openings so that each of the plurality of ramps 313, 314, 315, 316, 317 includes respective openings with diameters of a common size.

In embodiments, each of the plurality of ramps 313, 314, 315, 316, 317 may include at least two of the plurality sets of openings so that each of the plurality of ramps 313, 314, 315, 316, 317 include openings of at least two different common sizes that increase from the outer diameter to the inner diameter of the spiral construction 336.

In embodiments, each of the plurality of walls 308, 309, 310, 311, 312 may include only one set of the plurality of sets of openings so that each of the plurality of walls 308, 309, 310, 311, 312 includes respective openings with diameters of a common size.

In embodiments, each of the plurality of walls 308, 309, 310, 311, 312 may include at least two of the plurality sets of openings so that each of the plurality of walls 308, 309, 310, 311, 312 include openings of at least two different common sizes that increase from the outer diameter to the inner diameter of the spiral construction 336.

In embodiments, each set of the plurality of sets of openings 390 may corresponds to one of the plurality of compartments 301, 302, 303, 304, 305, 306 so that each of the plurality of compartments 301, 302, 303, 304, 305, 306 may be configured to hold oysters of a corresponding size range. The corresponding size range may increase from the outermost compartment 301 of the plurality of compartments to the innermost compartment 306 of the plurality of compartments. The corresponding size range may be configured to group oysters of appreciably the same size in only one corresponding compartment of the plurality of compartments 301, 302, 303, 304, 305, 306. In embodiments, the size range is chosen to achieve certain objectives, such as, for example, promote oyster growth and prevent bullying between oysters, to name a few.

In embodiments, when the containment assembly 300 is rotated, dithered and/or pitched, oysters which are smaller than the size range of the compartment holding the oysters may pass through the set of openings corresponding to that compartment to other compartments surrounding that compartment (e.g., the smaller oysters fall through the openings 390 to other more outwardly-disposed compartments).

Thus, in embodiments, a plurality of sheets is provided that forms a continuous spiral extending the length of the containment assembly and encapsulated by an outermost cylindrical barrier. Each turn of the spiral is made up of a 180-degree sheet concentric with the outermost cylindrical barrier ("wall sections") and a 180-degree sheet ("ramp sections") that connects adjacent wall sections (and the outermost cylindrical barrier) such that the internal volume of the spiraling sheets and outermost cylindrical barrier forms a continuous and contained spiral space. Each wall and each ramp has a unique radius of curvature. Each wall/ramp pair has a unique hole size configured to retain oysters of a certain minimum size (e.g., hole diameters are approximately 5-15% less than the second largest principal dimension, usually the width, of the minimum size of oyster to be retained) and therefore the internal volume of each ramp/wall pair can be considered a separate compartment in the continuous and contained spiral space, each compartment holding an exclusive range of oyster sizes between the defined minimum sizes. Hole sizes, and therefore the minimum size of oyster that each compartment will retain, increases towards the center of the spiral, the innermost compartment retaining harvest-size oysters and the outermost compartment, between the first ramp/wall pair and the outermost cylindrical barrier retaining seed oysters. With six (6) total compartments, size ranges may be 4 mm-34 mm in the outermost/first compartment (retained on 1/16" holes), 34 mm-51 mm in the second compartment (retained on 3/4" holes), 51 mm-60 mm in the third compartment (retained on 1+3/8" holes), 60 mm-69 mm in the fourth compartment (retained on 1+5/8" holes), 69 mm-78 mm in the fifth compartment (retained on 1+7/8" holes), and >78 mm in the innermost/sixth compartment (retained on 2" holes). The innermost compartment contains screw flighting that conveys harvest-size oysters out of the containment. As oysters grow, the entire containment is periodically rotated such that oysters tumble around the continuous and contained spiral space into higher/inner, adjacent compartments where oysters that have grown sufficiently large can remain and oysters that have not grown sufficiently will fall through holes, returning to the previous compartment. Oysters can thereby be continuously shaped and sorted frequently and simultaneously. Compartments may be sized to hold an approximately equal number of oysters per compartment and hole sizes may be chosen such that each compartment holds each oyster for an approximately equal amount of time during its growth from seed to harvest-size. Maximum holding capacity of the containment may be achieved by sizing each compartment to hold exactly the same number of oysters of each compartment's respective maximum oyster size in the same angular sector ("fill line") of the spiral. This leads to outer compartments being much thinner than inner compartments because in outer compartments oysters are smaller and the perimeter of the spiral inside the angular sector increases. However, without being bound by theory, a constraint on this maximization is that the width of each compartment (space from sheet to sheet) is preferably at least 3-5× the width of the largest oyster intended to be retained in that compartment to prevent bridging and other flow reliability problems.

In embodiments, a hollow shaft 319 having a first end and a second end may be disposed within the innermost one of the plurality of compartments 306, wherein the first end of the hollow shaft 319 is configured to receive seed-oysters. In embodiments, the seed oysters are pumped in with water at high velocity (e.g., higher than the settling velocity of the seed-oysters). The hollow shaft 319 may extend along a central axis of the containment assembly 300. The hollow shaft 319 may include a plurality of holes formed in the wall of the hollow shaft 319 between the first end and the second end and sized to allow seed-oysters to pass therethrough. The plurality of holes formed in the wall of the hollow shaft 319 may include rings of at least four holes distributed evenly along the length of the hollow shaft 319, for example, every 6 inches, every 12 inches or some other amount. It should be appreciated that the number of holes within each ring and the spacing between the rings are not limited by these amounts, and in embodiments the rings may have any number of holes and be spaced any distance apart.

In embodiments, the plurality of holes of the hollow shaft 319 may be sized so that pressure loss is distributed equally along a length of the hollow shaft 319 and so that seed-oysters are distributed evenly along the length of the hollow shaft 319. Without being bound by theory, pressure loss through the holes is so much greater than the pressure loss through the pipe itself that flow is equal through every hole regardless of its position along the length of the pipe. Because flow through each hole is approximately equal and because seed are well-mixed/suspended/non-settling, the number of seeds pushed through each hole is also equal and seed is evenly distributed lengthwise across the containment assembly.

The diameter of the holes may be, for example, approximately ½" plus or minus a tolerance. In embodiments, the size of the holes may be approximately three to five times an average diameter of seed-oysters of a species of oysters which the automated oyster maturation system is configured to grow.

In embodiments, the containment assembly 300 may include at least one monitoring device configured to receive and send information. The monitoring device may include devices, such as, for example, a camera, a load cell, a pressure gauge, a pitot tube, a force pad, a force sense resistor, a transducer, an anemometer, an accelerometer, a proximity sensor, an encoder, a light sensor, a water quality sensor, an electro-chemical sensor, and combinations thereof, to name a few.

In the case of a camera, the camera may be, for example, a camera configured to capture visible light in a harvest hopper, a camera configured to capture visible light in the containment assembly 300, a camera configured to capture infrared radiation in a harvest hopper, a camera configured to capture infrared radiation in the containment assembly 300, or a security camera, to name a few.

In the case of a load cell, the load cell may be, for example, a load cell configured to measure the weight of a harvest hopper, or a load cell configured to measure the weight of the containment assembly 300, to name few.

In the case of a force pad, the force pad may be, for example, a force sense resistor, or a transducer, to name few.

In the case of a proximity sensor, the proximity sensor may be, for example, a proximity sensor configured to sense relative movement between the housing 324 and settlement in a seabed 6.

In the case of an encoder, the encoder may be, for example, an encoder configured to reduce drift between the containment assembly and the housing, or an encoder configured to measure rotations, to name a few.

In the case of a light sensor, the light sensor may be a spectrometer.

In the case of a water quality sensor, the water quality sensor may be, for example, a thermocouple, or a thermistor, to name a few. The water quality sensor may be configured to measure one or more of the following variables: fecal coliform, chlorophyll, feces/pseudofeces, Seston (plankton, e.g., diatoms), nitrite, nitrate, ammonia, dissolved $O_2$, dissolved $CO_2$, dissolved nitrogen, bacteria, calcium, calcium carbonate, turbidity, salinity, pH, or combinations thereof, to name a few.

In the case of an electro-chemical sensor, the electro-chemical sensor may be configured to measure variables, such as, for example, ammonia, nitrites, nitrates, a specific molecule, or combinations thereof, to name a few.

In embodiments, the containment assembly 300 may be configured to rotate, dither and/or pitch based on information obtained or received from the at least one monitoring device. For example, a controller may take as input any one or combinations of measurements from the at least one monitoring device to determine whether the containment assembly 300 should be rotated, dithered and/or pitched.

In embodiments, the containment assembly 300 includes one or more lights, such as, for example, LED light strips. In this regard, each one of the plurality of compartments 301, 302, 303, 304, 305, 306 may include at least one LED light strip. The lights may be configured to, for example, provide light approximating sunlight, to provide light in the ultra-violate wavelength, to provide light in the ultra-violet band, to provide illumination periodically or aperiodically. As a further example, the lights may be configured to provide illumination for a predetermined length of time within a predetermined period of time, such as, for example, 16 hours in a 24-hour period, 32 hours in a two-day period, or 48 hours in a three-day period, to name a few. In embodiments, the lights may be configured to provide illumination in accordance with instructions received from a controller. In embodiments, the automated oyster maturation system may include one or more inlet assemblies 360 configured to feed seed oysters into the containment assembly 300 and flush out waste products (e.g., bio-deposits, which may include fecal matter, oyster shell shavings, dead oysters, which may be ground up by rotation of containment assembly 300, to name a few) from containment assembly 300 and/or harvest hopper 327. In embodiments, the system may include two inlet assemblies 360, with each inlet assembly 360 disposed as a respective end of the containment assembly 300. Each inlet assembly 360 may extend through an opening in the housing 324 and may be operatively connected to the hollow shaft 319. In embodiments, the inlet assembly 360 may include a pump 330 disposed at the distal end portion of the inlet assembly 360, and an injection hose 329 extending from the pump towards the containment assembly 300.

The pump 330 may be, for example, a titanium submersible pump with at least 60,000 hours of rated saltwater operation. The pump 330 may be configured to pump nutrient-rich water as well as the seed oysters through the inlet assembly 360 and into the containment assembly 300.

The injection hose 329 may include a first opening that is distal from the pump 330 and a second opening that is proximal to the pump 330. The first opening of the injection hose 329 may be below the water line and the second opening may be configured to receive the seed oysters pumped into the system through the pump 330. The injection hose 329 may be made of materials, such as, for example, rubber, plastic, thermoset polymers, layflat polyurethane hose, metal piping, and combinations thereof, to name a few. More details of the inlet assembly 360 are described below with reference to FIGS. 8-10.

In embodiments, a funnel with a first and second opening may be operatively connected to the injection hose and may be configured to receive and transmit seed oysters. In embodiments, the funnel may include, for example, a sump, radial brushes which extend across the first opening and are configured to prevent seed-oysters from floating out of the funnel, and/or foam, to name a few. In embodiments, the inlet assembly 360 may include an injection conduit, which may have a first and a second opening. In embodiments, the first opening of the injection conduit may be configured to connect to, and be in fluidic communication with, the opening in the housing of the containment assembly 300 (instead of the injection hose) and the second opening may be configured to connect to, and be in fluidic communication with, the first opening of the injection hose 329. In embodiments, the injection conduit may made materials, such as, for example, rubber, plastic, metal, and combinations thereof, to name a few. In embodiments, the automated oyster maturation system includes an ejection assembly 362 configured to eject harvest-ready oysters from the innermost compartment 306 of the plurality of compartments. More details of the ejection assembly 362 are described below with reference to FIGS. 8-10.

In embodiments, the automated oyster maturation system may include a floating hull 331 connected to the housing 324 by, for example, at least one tether 332. The floating hull 331 may include one or more components, such as, for example, a solar panel, a battery, an accumulator, a hydraulic pump, a programmable logic controller including at least a memory and a processor, a telemetry device, a radio modem, a control device, a communication device, an automatic identification system (AIS), a security camera, a flashing light, and combinations thereof, to name a few. The floating hull 331 may be operably connected to the housing via electric cables 333 and may be configured to provide electricity to components of the automated oyster maturation system. In embodiments, the floating hull 331 may be operably connected to the housing 324 by, for example, hydraulic cables 334 so that the floating hull 331 may provide hydraulic power to components of the automated oyster maturation system, and communication cables, wireless communication devices, a WiFi gateway, cloud computing services and/or a satellite uplink so that the floating hull 331 may be configured to send information (e.g., control instructions) to and/or receive information from components of the automated oyster maturation system, to name a few. In embodiments, the hull 331 may connect to multiple housings. In embodiments, if the hull 331 is provided with solar panels, the panels may provide enough power to charge batteries and/or hydraulic accumulators between containment assembly 300 actuations (e.g., between rotations or other movements). In embodiments, underwater cables may provide enough power to actuate a rotational device (e.g., a motor). In embodiments, hull 331 may include deterrent spikes and/or other measures to prevent birds from roosting on top of them. In embodiments, hull 331 may include other features or structural elements to qualify as real maritime markers.

In embodiments, the hull 331 may be designed to appear as a buoy/high-flier or another object familiar to boat operators to avoid confusion/collision.

In embodiments, tethers 332, electric cables 333, and/or hydraulic cables 334 may be configured to include slack (e.g., to accommodate heaving of hull 331). Tethers 332 may have less slack than electric cables 333 and hydraulic cables 334 so that tethers 332 may become taught before the electric cables 333/hydraulic cables 334 and thereby protect the latter from excessive strain. Hull 331 may be designed to be very weakly buoyant so that in strong sea states with large swells/waves, hull 331 submerges rather than break tethers 332. This may also help to clean solar panels of any debris. In this regard, solar panels may be angled to allow water and debris to run off.

In embodiments, rather than floating at the surface, the hull may be disposed below the surface at, for example, a position attached to the housing 324. Wave energy converters, tidal power generators, and/or grid power via subsea cable may then be used to power the overall system. The distal ends of the harvest hose and injection hose may be arbitrarily far from the surface since coupling between the harvest vessel and the twin funnels may be done remotely using live video. Thereby, all navigational and entanglement hazards may be completely removed, if necessary. With the hull on the housing 324, status updates and commands may be uploaded at high data rates by using an antenna or gateway at the water surface or via high-power transmitters/receivers.

In embodiments, the containment assembly 300 may include at least one screw flight 318 that is operable to push harvest-ready oysters from the containment assembly 300. The at least one screw flight 318 is preferably located within the innermost compartment 306 of the plurality of compartments of the spiral construction 336. In embodiments, the containment assembly 300 may include two screw flights 318 within the innermost compartment 306, with each screw flight having a handedness opposite to the other so that harvest-ready oysters may be ejected from both ends of the containment assembly 300. In embodiments, the at least one screw flight 318 may be, for example, an auger. The screw flight 318 may be helical throughout its entire extent. The diameter of the screw flight 318 may be, for example, one and a half times the diameter of the innermost one 306 of the plurality of compartments. In this regard, in a specific exemplary embodiment, the diameter of the innermost one 306 of the plurality of compartments is no less than:

$$(4*N/(\text{density}*\Pi*1.5)^{(1/3)}), \tag{1}$$

wherein N is the number of oysters which the automated oyster maturation system is configured to eject with every complete rotation of the containment assembly, and wherein density is the density of oysters in the central compartment.

In embodiments, the automated oyster maturation system may include at least one hopper 327 that receives harvest-ready oysters ejected from the ejection assembly 362. As described in more detail below with references to FIGS. 8-10, multiple hoppers 327 may be provided to receive harvest-ready oysters from multiple corresponding ejection assemblies 362. The hopper 327 may include a vibrator or other mechanism configured to dither the hopper 327. The hopper 327 may be disposed within the housing 324 or connected to an end portion of the housing 324. In embodiments, harvest-ready oysters may be ejected from compartment 306 by screw flight 318 into harvest hopper 327.

In embodiments, harvest hopper 327 may be configured to be evacuated rapidly using, for example, fish pumps, vacuum pumps, air lifts, venturi suction, regular end-suction centrifugal pumps and combination thereof, to name a few. In embodiments, the outlet assembly and harvest hopper 327 may have self-priming capability and/or a self-sealing suction connection, which may enable rapid cycle time. In embodiments, collection vessels may clean, bag, and ice oysters for just-in-time delivery to ports for immediate wholesale/distribution (e.g., no warehouse processing or inventory).

More details of the hopper are described below with reference to FIGS. 8-10.

In embodiments, the automated oyster maturation system may include at least one outlet assembly 364 configured to eject harvest-ready oysters from the hopper 327 and into a collection vessel. For example, if the system includes two hoppers 327, two corresponding outlet assemblies 364 may be provided to eject harvest-ready oysters from each hopper 327. The outlet assembly 364 may include a pump 363 disposed at the distal end portion of the outlet assembly 364, and an ejection hose 328 extending from the pump 363 towards the containment assembly 300.

The pump 363 may be, for example, a titanium submersible pump with at least 60,000 hours of rated saltwater operation. The pump 330 is configured to pump harvest-ready oysters from the hopper 327.

The ejection hose 328 may include a first opening that is distal from the pump 363 and a second opening that is proximal to the pump 363. The first opening of the ejection hose 328 may be below the water line and the second opening may be configured to eject the harvest-ready oysters pumped out of the system by the pump 363. The ejection hose 328 may be made of materials, such as, for example, rubber, plastic, reinforced Kanaflex™ suction hose, metal piping, two distinct conduits and/or hoses, each with two openings, a float (e.g., a funnel connected to an opening of the harvest hose and configured to receive harvest-ready oysters), an expanded flow insert near an opening of the harvest hose, a male connector configured to connect with a matching female connector, which may be from a harvest vessel, and combinations thereof, to name a few.

More details of the outlet assembly 364 are described below with reference to FIGS. 8-10.

As mentioned previously, in embodiments, each compartment of containment assembly 300 may be configured to hold oysters of a specific size range, defined by the sizes of the holes in the walls surrounding the compartment. In embodiments, holes may be sized such that each compartment may holds a given oyster for an approximately equal amount of time. For example, Crassostrea virginica oyster length ranges 4-34 mm, 34-51 mm, 51-60 mm, 60-69 mm, and 69-78 mm may represent approximately equal periods of an oyster's growth lifecycle with 78 mm (~3 in) being harvest size. Without being bound by theory, it is believed that the width of the oysters is the limiting dimension, as oysters may go through the smallest possible holes lengthwise, and in embodiments, the size of the circular holes may be configured to sort oysters based primarily on width. Continuing the example, the width of Crassostrea virginica oysters may be 70% of the length. Continuing the example, in embodiments, holes may be further undersized by a predetermined amount, such as, for example, 5%, 10%, 15%, or within a range of 0-15%, to name a few. Continuing the example, and rounding to standard imperial hole sizes, in embodiments, holes in containment assembly 300 for Crassostrea virginica oysters may be, for the outer enclosure 307 and the plurality of walls 308, 309, 310, 311, 312, 1/16" (outer enclosure 307), 0.75" (wall 308), 1.375" (wall 309), 1.625" (wall 310), 1.875" (wall 311), and 2" (wall 312), to name a few. In embodiments, hole sizes may be configured to accommodate any species of oyster (e.g., European, Pacific, and/or Japanese, to name a few) according to data on growth rates (e.g., in order to determine the correct size ranges) and careful measurements of proportions (e.g., in order to determine radius of the hole based off of the length and width of the oyster at each stage of growth).

In embodiments, the holes may be of a deterministic shape capable of sorting objects based on nominal maximum dimensions. For example, in embodiments, the holes may be circles formed in the walls and ramps of containment assembly 300. In embodiments, holes may be oval-shaped.

In embodiments, the sizing of the central compartment (e.g., the innermost one of the compartments, or compartment 306, to name a few) may be different from the other compartments. In embodiments, the size of the central compartment may be reduced relative to the other compartments, which may, without being bound by theory, help to, for example, evacuate harvest-size or close-to-harvest-size oysters as fast as possible from the central compartment and/or give more space, in other compartments, to oysters which are still growing. In embodiments, as described previously, the central compartment may include a screw flight, configured to transmit oysters along the central compartment in the direction indicated in FIG. 6B.

In embodiments, the last flight section should preferably hold the maximum number of oysters ejected from the mint with each rotation. As an example, assuming a 40 ft mint with 300,000 Crassostrea virginica oysters with a 12-month growing cycle and rotation frequency daily (365 rotations per year), ~800 oysters are ejected with each rotation (assuming the mint has been charged with 300,000 oysters evenly over one growth cycle). If seed is evenly distributed to both halves of the 40 ft mint (which it in this example is because of the ~½" holes distributed along the central shaft), then ~400 oysters will exit each side of the 40 ft mint with each rotation. In embodiments, the pitch of the screw flighting in the central compartment may be 1.5× the diameter of the central compartment. With an adult oyster density of 0.175 oysters/in$^3$ (relatively lower packing fraction while tumbling), the diameter of the central compartment and the pitch of the central screw flighting can be solved for as ~12" and ~18" ($400/0.175=\Pi*1.5*(d^3)/4$). A factor of safety may be included, but even if the central compartment is undersized slightly (because mint has been overcharged due to human error or less-than-expected seed mortality or because of variance in growth rate) it will not lead to catastrophic consequences because even if the central compartment overfills and oysters back up into outer compartments, the screw flighting will continue to convey and eventually push all harvest-size oysters out.

In embodiments, given a predetermined size of the central or innermost compartment and holes, the spiral construction 336 may be sized such that each revolution/compartment holds an approximately equal number of oysters and such that the holding capacity of the containment assembly 300 (in total number of oysters of all sizes) is maximized. Because oysters increase in size from outer compartments to inner compartments, outer compartments may be smaller than inner compartments (e.g., compartment 301 may be smaller than compartment 302, compartment 302 may be smaller than compartment 303, etc.). For example, in embodiments, the cross-sectional area of the containment assembly, excluding the area already dedicated to a central compartment (e.g., compartment 306), may be allocated approximately to each compartment/oyster-size in proportion with the relative volume of an individual oyster to be held in that compartment. Specifically, and without being bound by theory, dividing the rectangular volume of an oyster of a size which a compartment may be configured to hold by the sum of the rectangular volumes of oysters of each size which a compartment may be configured to hold may yield the fraction of the cross-sectional area of the containment assembly 300 (less that area already allocated to the central compartment) to be apportioned to the compartment intended to hold oysters of said certain size. In embodiments, adjustments may be made to accommodate for packing fraction (e.g., the tightness with which oysters pack together), which may decrease as oyster size increases, and/or level line (e.g., the angles of repose which oysters may settle to inside of the containment assembly 300). In embodiments, a different apportionment method may be used (e.g., where the containment assembly is less than 5 feet in diameter, which may otherwise cause the outermost compartment to be thinner than the smallest dimension of the oysters which it is meant to hold). In embodiments, walls and ramps may have a non-zero thickness, and compartment sizes may be configured to increase the gaps between adjacent ramps and walls, which may improve oyster flow (e.g., a space ~3-5× the width of the oyster-size in each compartment). In embodiments, the above method may be used to determine wall diameters, which may be considered the nominal "diameters" of each compartment.

Without being bound by theory, it is believed that even if oysters could be perfectly apportioned in each compartment so number and volume in each compartment is initially exactly the same, different standard deviations in growth rates at each stage of growth may cause the number of oysters in each compartment to fluctuate over time.

Turning to FIG. 6A, in embodiments, containment assembly 300 may be configured to rotate in the indicated direction 52 around axis of revolution 9 (FIG. 6B). In embodiments, spiraling ramps 313, 314, 315, 316, 317 may transfer oysters from outer compartments to adjacent inner compartments with every complete rotation. In embodiments, oysters which are too small to remain in the adjacent inner compartments may fall through the holes in the walls and ramps back into the outer compartments. For example, in embodiments, compartment 301, 302, 303, 304, 305, and 306 may be configured to hold oysters of a particular size (e.g., small oyster 1 for compartment 301, medium oyster 2 for compartment 303, and large oyster 3 for compartment 305, to name a few). Continuing the example, in embodiments, wall 307 may have holes configured to permit, for example, water and nutrients to flow into the containment assembly, and bio-deposits (e.g., fecal matter, oyster shell shavings, and/or dead oysters, which may be ground up by rotation of the containment assembly, to name a few) to flow out of the containment assembly. Continuing the example, in embodiments, ramp 313 and wall 308 may have holes which are configured according to the size of oyster which compartment 302 may be configured to hold (e.g., a size larger than the size of oyster which compartment 301 is configured to hold). Continuing the example, in embodiments, ramp 314 and wall 309 may have holes which are configured according to the size of oyster which compartment 303 may be configured to hold (e.g., a size larger than the size of oyster which compartment 302 is configured to hold). Continuing the example, in embodiments, ramp 315 and wall 310 may have holes which are configured according to the size of oyster which compartment 304 may be configured to hold (e.g., a size larger than the size of oyster which compartment 303 is configured to hold). Continuing the example, in embodiments, ramp 316 and wall 311 may have holes which are configured according to the size of oyster which compartment 305 may be configured to hold (e.g., a size larger than the size of oyster which compartment 304 is configured to hold). Continuing the example, in embodiments, ramp 317 and wall 312 may have holes which are configured according to the size of oyster which compartment 306 may be configured to hold (e.g., a size larger than the size of oyster which compartment 305 is configured to hold).

Continuing the example, in embodiments, as the containment assembly 300 rotates, small oyster 1 may leave compartment 301 and enter compartment 302 via ramp 313. Continuing the example, in embodiments, if the oyster has not grown large enough (e.g., the oyster is smaller than the size which compartment 302 is configured to hold), then the oyster may fall through the holes in the wall 308 or ramp 313 back to compartment 301. Continuing the example, in embodiments, if instead the oyster has grown large enough (e.g., the oyster is at least the size which compartment 302 is configured to hold), then the oyster may remain in compartment 302. Continuing the example, in embodiments, as the containment assembly 300 rotates, the oyster may leave compartment 302 and enter compartment 303 via ramp 314. Continuing the example, in embodiments, if the oyster has not grown large enough (e.g., the oyster is smaller than the size which compartment 303 is configured to hold), then the oyster may fall through the holes in the wall 309 or ramp 314 back to compartment 302. Continuing the example, in embodiments, if instead the oyster has grown large enough (e.g., the oyster is the size of medium oyster 2 and/or at least the size which compartment 303 is configured to hold, to name a few), then the oyster may remain in compartment 303. Continuing the example, in embodiments, as the containment assembly 300 rotates, the oyster may leave compartment 303 and enter compartment 304 via ramp 315. Continuing the example, in embodiments, if the oyster has not grown large enough (e.g., the oyster is smaller than the size which compartment 304 is configured to hold), then the oyster may fall through the holes in wall 310 or ramp 315 back to compartment 303. Continuing the example, in embodiments, if instead the oyster has grown large enough (e.g., at least the size which compartment 304 is configured to hold), then the oyster may remain in compartment 304. Continuing the example, in embodiments, as the containment assembly 300 rotates, the oyster may leave compartment 304 and enter compartment 305 via ramp 316. Continuing the example, in embodiments, if the oyster has not grown large enough (e.g., the oyster is smaller than the size which compartment 305 is configured to hold), then the oyster may fall through the holes in wall 311 or ramp 316 back to compartment 304. Continuing the example, in embodiments, if instead the oyster has grown large enough (e.g., the oyster is the size of large oyster 3 and/or at least the size which compartment 305 is configured to hold, to name a few), then the oyster may remain in compartment 305. Continuing the example, in embodiments, as the containment assembly 300 rotates, the oyster may leave compartment 305 and enter compartment 306 via ramp 317. Continuing the example, in embodiments, if the oyster has not grown large enough (e.g., the oyster is smaller than the size which compartment 305 is configured to hold), then the oyster may fall through the holes in wall 312 or ramp 317 back to compartment 305. Continuing the example, in embodiments, if instead the oyster has grown large enough (e.g., at least the size which compartment 306 is configured to hold, to name a few), then the oyster may remain in compartment 306. In embodiments, when oysters grow to the size that they to remain in the central compartment 306, they may be conveyed out of containment assembly 300 by screw flight 318. The hole sizes and diameters of each compartment of containment assembly 300 may be designed such that each compartment holds approximately the same number of oysters for approximately the same amount of time. This maximizes the holding capacity of containment assembly 300 for a given envelope.

Without being bound by theory, it is believed that providing holes with a circular profile is preferred because circles sort purely based on maximum dimensions and eliminate orientation dependence.

Without being bound by theory, it is believed that containment assembly 300 presents several advantages over containment assemblies 100 and 200, including improvements in sorting frequency, ease in fabrication due to the single-spiral construction, and improvements in volumetric holding capacity for a given containment envelope, to name a few.

In the example of FIG. 6A, which is designed for a specific species of oyster, *Crassostrea virginica*, the outer diameters of compartments 301, 302, 303, 304, 305 and 306 are 48", 46", 43", 38", 30", and 12", respectively, and the hole sizes in walls 308, 309, 310, 311, and 312 are, 7/8", 1+3/8", 1+5/8", 1+7/8", and 2", respectively (the outer enclosure 307 may be perforated with 1/16" holes, for example). These hole sizes retain oysters with lengths 4 mm, 34 mm, 51 mm, 60 mm, 69 mm, and 75 mm, respectively—approximately even growth milestones during the lifecycle of an oyster. Each compartment holds approximately 2,000 oysters for a total holding capacity of ~10,000 oysters—a relatively small oyster mint compared to what is possible. Compartments may be increasingly large to accommodate oysters as they grow, however, outer compartments may not be so thin that the oyster size they are meant to hold cannot fit or properly tumble (twice the minimum oyster width is provided in the present example). In this example, the hole sizes are chosen based on the proportions and time-changing growing speeds of the specific species of oyster. Other oyster species may be accommodated by adjusting hole and compartment sizes. In embodiments, the containment assembly 300 is preferably kept not more than 1/2 full (e.g., not more than 1/3 full).

In embodiments, the containment assembly 300 may be configured to receive seed oysters having lengths larger than 4 mm. For example, in embodiments, the outer diameter of compartments 301, 302, 303, 304, 305 and 306 and the hole sizes in walls 308, 309, 310, 311, and 312 may be adjusted to accommodate seed oysters having a starting length of 9-12 mm. Seed oysters having such larger sizes have lower sensitivity and mortality as compared to smaller seed oysters. This results in less accumulation of dead shell and more predictability in knowing exactly how many seeds to inject to keep the output constant over time. In embodiments, the size of the central shaft 319 may be increased to a range of, for example, 3 inches to 6 inches, to accommodate the larger seed oysters.

An advantage associated with using larger seed oysters is that the material used to form the outer enclosure 307 may have larger openings. For example, instead of using 1/16" perforated sheet on the outside of the containment assembly 300 (which is expensive and only has 30-40% open area, which limits waterflow through the containment assembly 300 to retain 4 mm seed), the outer enclosure 307 may be made of 3/16"-1/2" expanded aluminum sheet or wire mesh or perforated sheet, for example, with larger/more closely spaced holes (which is very inexpensive and has 70% open area). Such expanded sheet has diamond-shaped openings and wire mesh has square openings, but circular openings are not required on the outer enclosure 307 because it is not intended for sorting oysters (i.e., no oysters pass through it). In embodiments, depending on, for example, the depth at which the system is placed and nutrient availability, the increased open area of the expanded metal (or other material with greater open area such as wire mesh or perforated sheet with larger holes and closer hole spacing) may obviate the need for injection pumps 430 altogether (e.g., flow through mint alone is enough to feed oysters), which eliminates the expensive pumps that would need to be serviced.

Figure 7:
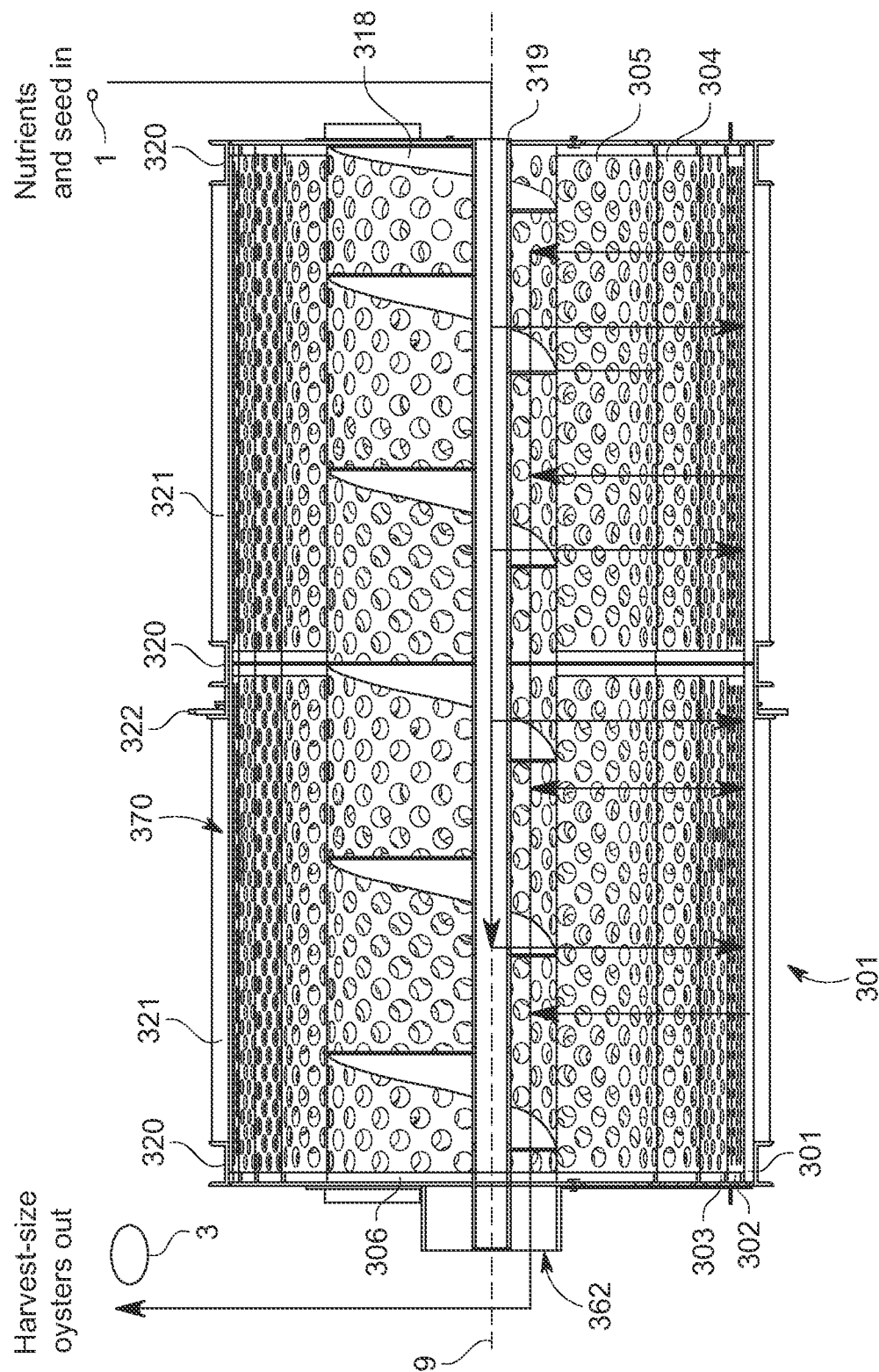
FIG. 7 shows a side-view cross-section of a containment assembly in accordance with an exemplary embodiment of the present invention.

FIG. 7 shows a side-view cross-section of containment assembly 300 according to an exemplary embodiment of the present invention. In embodiments, seed-oysters (e.g., small oysters 1) may be injected into containment assembly 300 via central shaft 319. In embodiments, central shaft 319 may be in the shape of a hollow cylinder. In embodiments, central shaft 319 may have holes formed in the wall of the shaft and distributed along its length. The holes of central shaft 319 may be of a minimum size to allow seed-oysters to pass through (e.g., 3 to 5 times the length of the seed oysters being injected). In embodiments, the holes of central shaft 319 may be sized such that the pressure loss through the holes is much greater than the pressure loss through the central shaft itself, which, without being bound by theory, may result in approximately equal flow and an equal number of seeds flowing through each hole. In embodiments, flow through holes may not decay substantially along length of central shaft 319. In embodiments, the seed-oysters may exit the central shaft and enter the central compartment 306. In embodiments, because the seed oysters may be smaller than the holes in various compartments and/or because the containment assembly 300 may be rotated, the seed oysters may readily fall through the successive layers of the spiral construction 336 (e.g., the walls and/or ramps of compartments 302, 303, 304, 305, and 306) and begin growing in the outermost compartment (e.g., compartment 301).

In embodiments, the central shaft 319 may be partitioned in two halves by an internal plate and seed oyster may be injected through both ends. In this regard, there may be an equal number of distributed holes between each pair of bulkheads. In general, holes may be evenly spaced, except in the containment assembly sections adjacent to adult-oyster exits ("spouts") where holes may be crowded towards the center of the containment assembly to prevent seed from inadvertently tumbling into the harvest hoppers after exiting the central shaft, before settling into the outermost compartment. The containment assembly 300 may be charged with seed in different ways, for example, by initially charging with seed all at once (250,000-500,000 seeds for a 40 ft mint, for example) or charging over a period of time, such as, for example, the first growth cycle to avoid spikes in compartment-change and harvest-size oyster discharge. Regardless, and not to be bound by theory, once a mint has been in operation for several growth cycles, the standard deviation in growth rates creates averaging so an approximately equal number of oysters may level-up and be discharged into harvest hoppers each rotation.

In embodiments, bulkheads 320 of the containment assembly 300 may include a rolled channel disposed around a thin, flat plate. Beams 321 may be provided between the bulkheads 320 to provide bending and torsional reinforcement such that the walls and spiraling ramps may be as thin as possible.

In embodiments, containment assembly 300 may be rotated continuously or at any suitable interval for the maintenance of maturation of oysters. For example, referring back to FIG. 7, in embodiments, containment assembly 300 may be configured to rotate every 20 minutes by a first amount (e.g., pi/4 radians) and a second amount (e.g., pi/12 radians) before venting (or driving) back the first amount (e.g., pi/4 radians) to equilibrium. In embodiments, the first amount may be configured to be the point at which oysters slip and/or tumble inside containment assembly 300. Continuing the example, in embodiments, by rotating the containment assembly 300 in this manner every twenty minutes for 8-hour daylight periods (24 rotations), the containment assembly 300 would rotate approximately one complete revolution each day. Continuing the example, by charging a hydraulic accumulator during the twenty-minute intervals and discharging it to actuate hydraulic motor 325, a relatively small hydraulic pump and solar panel may be used. Continuing the example, in embodiments, hydraulic motor 325 may be capable of 2,000 in-lbs at 100 rpm/1800 psi and sprocket 322 may provide a 180:12 speed reduction, which, without being bound by theory, would provide more than enough torque to drive the containment assembly 300 (e.g., with a maximum expected torque of 15,000 in-lbs). Continuing the example, and without being bound by theory, it is believed that by driving the containment assembly 300 the first and second amount (e.g., an amount slightly greater than the slip angle of the oysters (pi/4+pi/12 radians, for example)) and then allowing the hydraulic motor 325 to vent in reverse a greater path length and sorting efficiency can be achieved without increasing wall or spiraling ramp size. In embodiments, a rotational device (e.g., hydraulic motor 325) may use a fine jacking/stepping motion when tumbling/sorting, for example, rotating containment assembly 300 2*(slip angle)+pi/96 radians and then back by 2*(slip angle)+pi/192 radians.

In embodiments, the automated oyster maturation system may include one or more encoders, which may track any fine stepping motions (e.g., <5% step per stroke) of the rotational device (e.g., motor 325). In embodiments, the rotational device may jerk/dither the containment at the start and stop of each motion, which, without being bound by theory, is believed may help reduce friction.

In embodiments, containment assembly 300 may be configured by changing, for example, the period in each day which the assembly rotates, the interval between rotations, and the amount of rotations, to name a few, to rotate more or less frequently than once each day. For example, in embodiments, the containment device 300 may rotate at least once every 12 hours, at least once every 24 hours, at least once every week, at least once every month, at least once every 3 months, to name a few. In embodiments, containment assembly 300 may be configured to rotate aperiodically or irregularly (e.g., not at all between December through March, but at scheduled times from April to November, to name a few). In embodiments, containment assembly 300 may be configured to rotate via a controller, which may include a processor and memory, which may be programmed based on information from, for example, a monitoring device (e.g., a device tracking oyster growth). In embodiments, containment device 300 may be configured to rotate after receiving an input from an external controller (e.g., a programmable logic controller).

In embodiments, the bottom-cage design of FIG. 5 may be advantageous in that, for example, the weight of the system may no longer be as large of a constraint because floatation and complex grid moorings are not required, the device may be completely protected from storms, and the system may be more easily kept inconspicuous for security reasons, to name a few. Without being bound by theory, it is believed that the positive pressure created inside of containment assembly 300 by its depth and/or the additional head provided by submersible pumps 330 may increase the absorption of nutrients by the oysters and/or help to flush out waste products (e.g., bio-deposits). Also, it is believed that mortality of small oysters (which may be less than 20% in more favorable offshore growing conditions, compared to upwards of 70% for nearshore farms) may be diminished by the oyster-tumbling action of the containment assembly 300. Further, the system may be made predator-proof by providing it with features, such as, for example, the size of all openings being no greater than $\frac{1}{16}$" (e.g., of wall 307 and/or submersible pumps 330, to name a few), packing and/or trim which seal all connections (e.g., from inlet assembly to containment 300 and/or from containment 300 to harvest hopper 327, to name a few), and one-way valves or rubber/brush seals for use in, for example, the harvest hose 328 and injection hoses 329, to name a few.

In embodiments, containment assembly 300 and frame 324 may be made entirely from welded aluminum and welded/painted steel, respectively, using commonly available metal shapes that are cut and/or rolled/bent so as to minimize processing. In embodiments, use of non-TBT paints and food-grade hydraulic oil may make the device completely environmentally friendly.

In embodiments, the various components of the system may be configured to provide a year service life of twenty (20) years or longer in saltwater without maintenance. For example, in embodiments, containment assembly 300 may be aluminum. Continuing the example, in embodiments, the roller 323 may be solid, cast, polyurethane which may be supported by self-lubricating (e.g., dry-running) bearings and stainless-steel axles, to name a few. Continuing the example, in embodiments, chain 326 may be stainless steel, oversized, under unidirectional tension, and protected by "soft" hydraulic solenoid valves (which may, for example, prevent crack growth by preventing sudden change of direction or shock loads). Continuing the example, in embodiments, sprocket 322 may be separated from containment assembly 300 by washers under bolt compression, which, without being bound by theory, may exhibit, relative to other materials, high friction, high shear strength, high compressive strength, indifference to saltwater, and electrical insulation to prevent galvanic corrosion, to name a few. Such washers may be made of materials such as, for example, plastic, composite and ceramic, to name a few. Continuing the example, in embodiments, rollers 323 and an insulating line 335, which may be made of any appropriate insulating material (e.g., a plastic), may protect containment assembly 300 and harvest hopper 327 from galvanic corrosion by frame 324, which may, in embodiments, be made of steel. Continuing the example, and without being bound by theory, in embodiments, corrosion may be already significantly less aggressive where the automated oyster maturation system is placed on the seafloor, compared to the surface/"splash zone", because of the low-oxygen, low-temperature, and well-flushed conditions there.

FIGS. 8-12 illustrate an automated oyster maturation system according to another exemplary embodiment of the present invention. It should be appreciated that the prior exemplary embodiment of the inventive oyster maturation system described above with reference to FIGS. 5-7 may have the same or similar components as that of the present exemplary embodiment, so that more detailed descriptions provided herein with reference to the present embodiment may be applied to the prior exemplary embodiment and vice versa without departing from the spirit and scope of the present invention.

Figure 8:
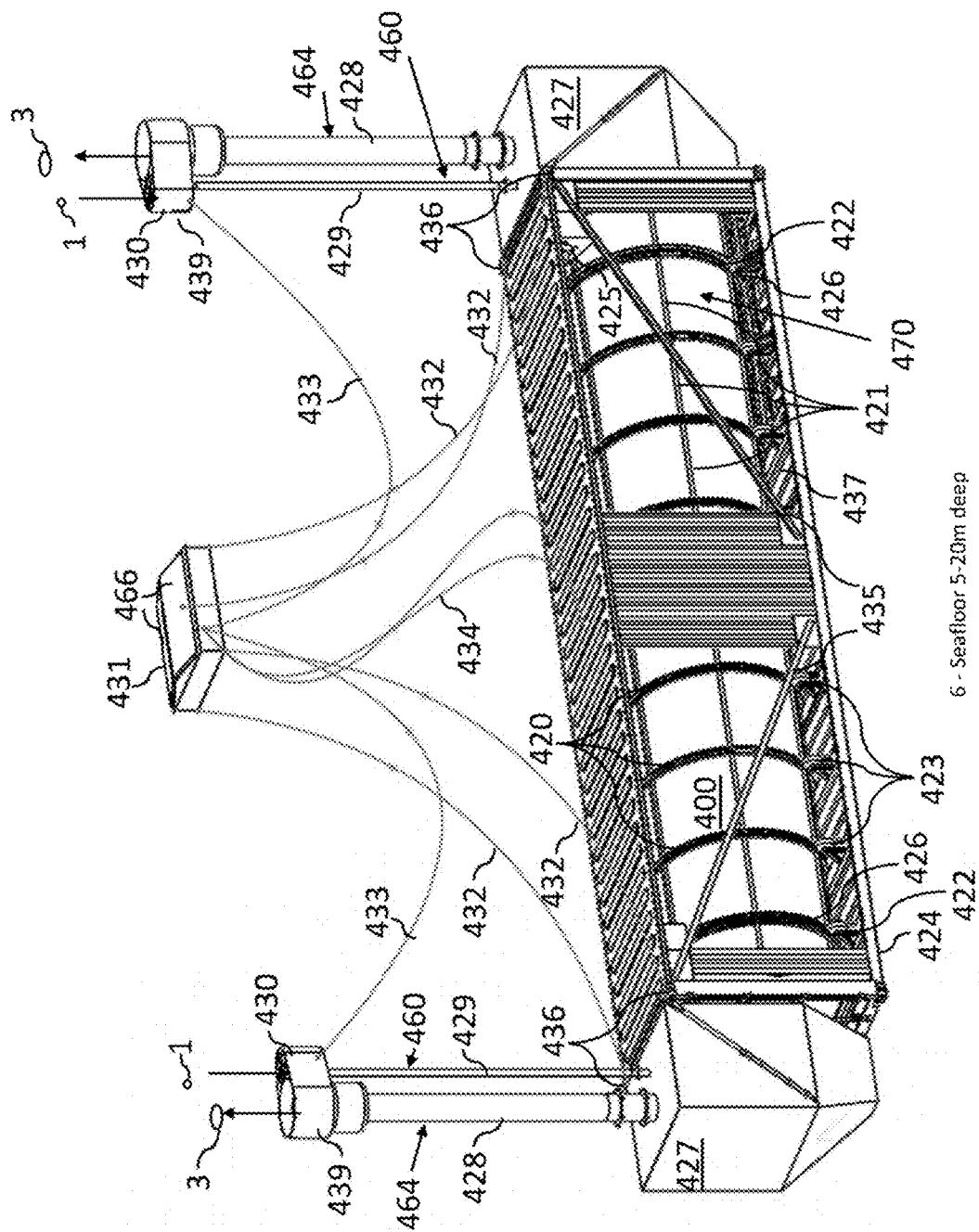
FIG. 8 is a schematic illustration depicting an isometric view of an automated oyster maturation system in accordance with an exemplary embodiment of the present invention.
Figure 9:
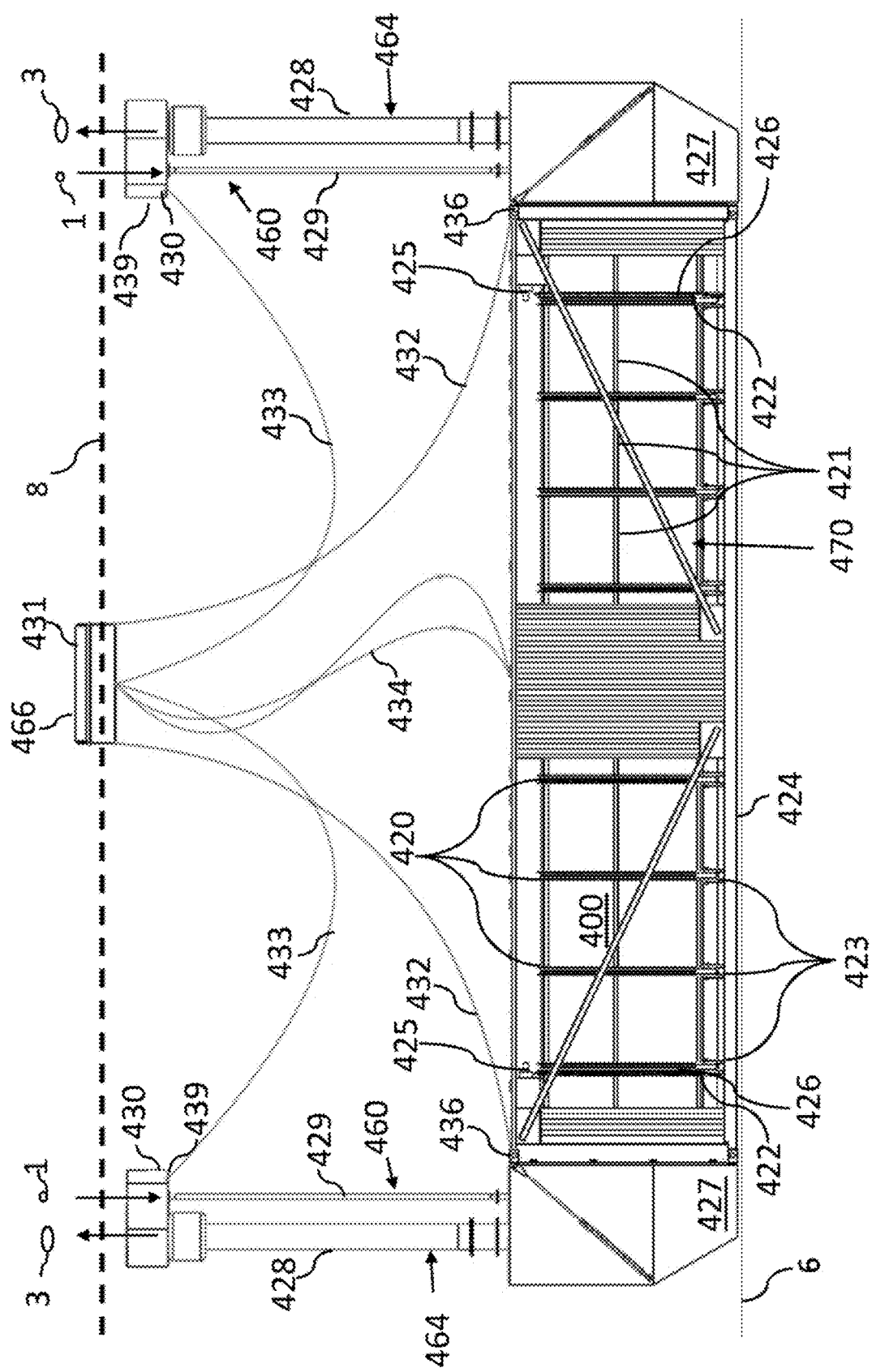
FIG. 9 is a schematic illustration depicting a side view of an automated oyster maturation system in accordance with an exemplary embodiment of the present invention.

Specifically, FIG. 8 is a schematic illustration depicting a perspective view of an automated oyster maturation system in accordance with an exemplary embodiment of the present invention. FIG. 9 is a schematic illustration depicting a side view of an automated oyster maturation system in accordance with an exemplary embodiment of the present invention. As in the previously described exemplary embodiment, the system of the present embodiment may include a containment assembly 400 having an outer enclosure 470, which may have, for example, a cylindrical shape. Also, as in the previously described exemplary embodiment, containment assembly 400 may include bulkheads 420 connected by beams 421 and may sit on rollers 423 inside of a housing 424.

In embodiments, housing 424 may be a mass-manufactured container, such as, for example, a shipping container. In the case of a shipping container, the container may be, for example, a 10 foot, a 20 foot, a 40 foot, a 45 foot, or a 53 foot, to name a few, high cube container (e.g., the container may have a length of, for example, 10 feet, 20 feet, 40 feet, 45 feet, or 53 feet, to name a few). In embodiments, housing 424 may be modified from its original configuration to adapt it for use with the containment assembly 400 and other components of the overall system. For example, portions of the side walls of housing 424 may be cut out to allow for seawater to flow through, housing 424 may be provided with diagonal reinforcements 435, flooring of the housing 424, particularly if the housing 424 is a shipping container, may be removed partially or completely (leaving flooring where possible may save time and helps stem subsidence in unstable soil conditions, although in pressure treated wooden container floors could pose a toxicity risk and in embodiments may need to be removed), floor beams 437 may be removed where they overlap with the positions of rollers 423 and replaced by wheel mounting beams (e.g., original c-channels may be replaced by closed box sections for wheel stands to be fixed thereupon), holes may be cut in both ends of shipping container such that outlets 438 (FIG. 10) from containment assembly 400 can exit shipping container 424 and enter harvest hoppers 427, and harvest hoppers 427 may be hung on the end-faces of housing 424, as shown in FIG. 8, such that space is reserved inside of housing 424 for a longer containment assembly 400, which can hold more oysters, to name a few.

In embodiments, if a shipping container is used for the housing 424, the shipping container may remain ISO certified for intermodal transport land/sea and may still be lifted from its corner castings 436. A 40-foot-high cube container would allow for use of a 40-foot mint, which in embodiments may hold between 250,000-500,000 oysters (50,000-100,000 oysters of each size). As in the previously-described exemplary embodiment, the system may include one or more inlet assemblies 460 that include injection hoses 429 and pumps configured to inject seed oysters into the containment assembly 400, one or more outlet assemblies 464 that include ejections hoses 428 and pumps configured to transport harvest-ready oysters to, for example, collection vessels, and one or more ejection assemblies 462 configured to eject harvest-ready oysters from the containment assembly 400. Ejection hoses 428 and injection hoses 429 may extend from harvest hoppers 427. In embodiments, each ejection hose 428 may be coupled with a corresponding injection hose 429 by twin funnels 439, which prevents the hoses from twisting together.

As previously described, containment assembly 400 may be actuated in a number of ways, such as, for example, hydraulic motors 425 turning sprockets 422 via chains 426, hydraulic pistons via a jacking motion (e.g., with ratchet and pawl, which could provide the ability to generate high accelerations to dither oysters and reduce friction and promote tumbling, although range of motion may be a concern with pistons of limited stroke inside a finite container envelope), by driving all or at least some of the rollers 423, or via a coaxial low speed high torque motor on a deep planetary gear reduction (similar to transit mixer motors) driving the central shaft of containment assembly 400, to name a few. In embodiments, passive motion may be achieved via water turbines and very large gear reduction.

As previously described, the system in accordance with the present exemplary embodiment may include a hull 431 that floats at the surface and houses components, such as, for example, solar panels, batteries, PLC(s), hydraulic accumulator, hydraulic pump, radio modem and other electronics necessary for telemetry, controls, and communication, to name a few. Hull 431 may be secured by tethers 432 to housing 424 and electric cables 433 and hydraulic cables 434 may run between the hull 431 and housing 424. In embodiments, multiple mints (e.g., 2, 3, 4, 5 or more mints) may share a single large hull. Motors 425 may be of any type, such as, for example, hydraulic or electric, to name a few. Solar panels may provide enough power to charge batteries and/or hydraulic accumulators between containment assembly 400 actuations (e.g., between each rotation of the containment assembly 400). Underwater cables may be used in the case of, for example, large mint farms. Hull 431 may include deterrent spikes and/or other measures to prevent birds from roosting on top of them and may include other features or structural elements to qualify as real maritime markers.

As described in regard to the previous exemplary embodiment, tethers 432, electric cables 433, and/or hydraulic cables 434 may be designed with slack to accommodate moderate heaving of hull 431 during typical ocean states. Tethers 432 may have less slack than electric cables 433 and hydraulic cables 434 so that tethers 432 become taught before the electric cables 433/hydraulic cables 434 and thereby protect the latter from excessive strain. Hull 431 may be designed to be very weakly buoyant so that in strong sea states with large swells/waves, hull 431 submerges rather than breaking tethers 432. This may also help to clean solar panels of any debris. In embodiments, solar panels may be angled to allow water and debris to run off.

In embodiments, the use of a shipping container as the housing 424 may allow the system to be mass produced. In this regard, the use of a shipping container maxes out the oyster holding capacity of a mint while still allowing the mint to be transported on roads and container ships. If proximity to manufacturing or alternative/future transportation methods make the transportation of larger oyster mints possible, mints may be made even larger (e.g., more compartments may be created to reduce pressure between oysters) inside of custom frames.

Without being bound by theory, it is believed that the holding capacity of a mint grows in at least somewhat direct proportion to the square of the diameter of the containment assembly 400 $D^2$ and in at least somewhat direct proportion to the length of the containment assembly 400 $L^1$ whereas material costs grow in at least somewhat direct proportion to the diameter of the containment assembly 400 $D^1$ and in at least somewhat direct proportion to the length of the containment assembly $L^1$. It is therefore advantageous to maximize mint diameter in a given envelope (a shipping container in the present example). For a given diameter, a length:diameter (L:D) ratio much greater than 2:1 to 3:1 may cause inner-most compartment 406 to overfill because it takes longer for harvest-ready oysters to exit into the harvest hopper (a longer mint requires more rotations to eject oysters). Therefore, in embodiments, where the housing 424 is a 40 foot shipping container, screw 418 inside the inner-most compartment 406 of the 40-foot containment assembly 400 may be right-handed in one half and left-handed in the other half so that oysters in different halves are ejected in opposite directions. In this regard, containment assembly 400 may be split into two 20-foot containment assemblies and built inside 20-foot shipping containers, although slightly greater economy of scale may be achieved by combining containment assemblies inside of a single 40-foot shipping container.

Figure 10:
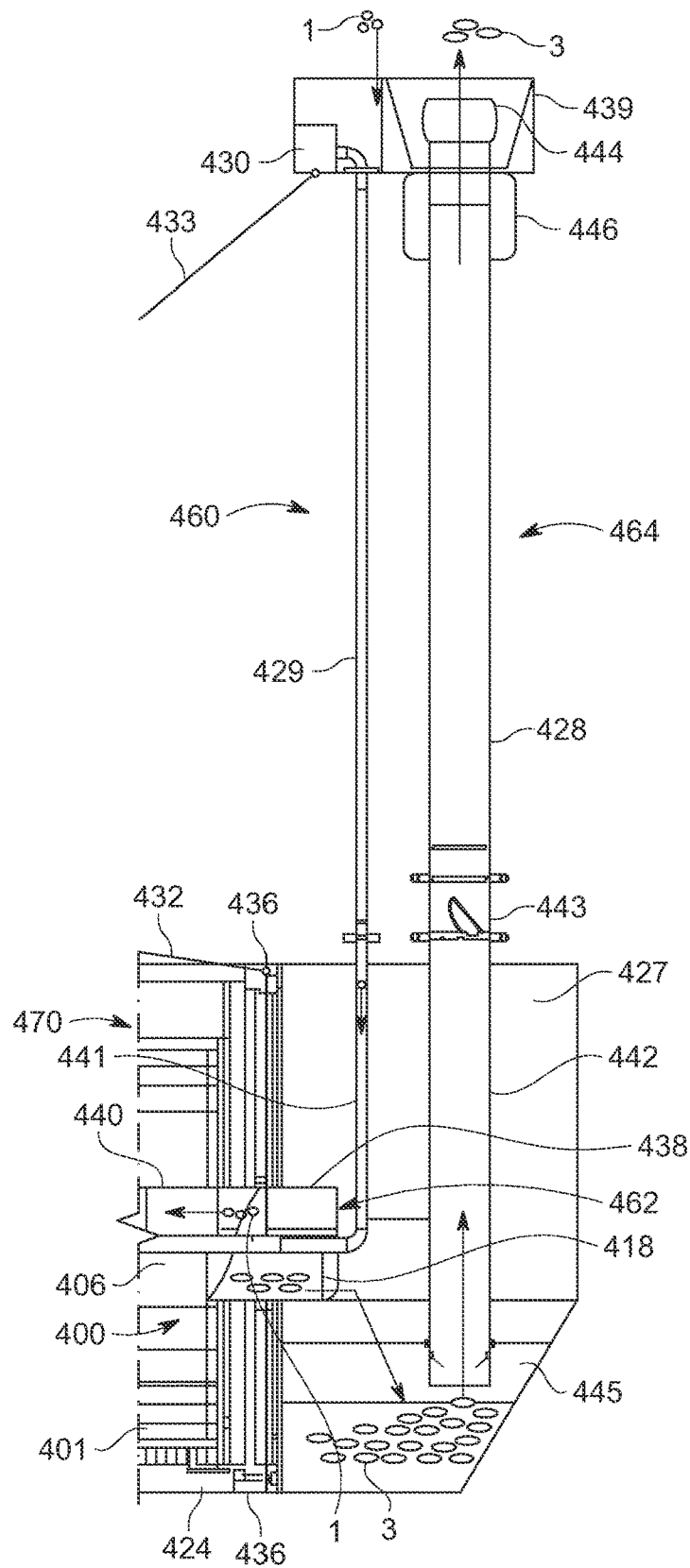
FIG. 10 is a schematic illustration depicting a cross-section of a hopper in accordance with an exemplary embodiment of the present invention.

FIG. 10 shows a cross section of one of the two harvest hoppers 427 in accordance with an exemplary embodiment of the present invention. Seed oysters 1 (~4 mm) may be dumped into the left-hand side of twin funnel 439 where pump 430 injects them into containment assembly 400 through injection hose 429, injection pipe 441 and central shaft 440. In embodiments, pumps 430 may also provide, for example, 200-1000 GPM in additional nutrients from the surface and positive containment pressure for cleaning and increasing nutrient absorption/availability to oysters. Central shaft 440 has holes that may be distributed equally along its length such that each section of containment assembly 400 receives approximately equal water/nutrient flow and equal numbers of seed oysters (the hole size is preferably small, for example, ½", so pressure loss inside central shaft 440 is insignificant compared to pressure loss through distributed holes and therefore each hole receives approximately equal flow). Seed oysters fall down to outer-most compartment 401 and progress back to inner-compartment 406 throughout their growth lifecycle. Once harvest-size oysters 3 are in inner-most compartment 406, screw flight 418 may push them through outlet 438 into harvest hopper 427 wherefrom they may be pumped through harvest pipe 442, one-way valve 443 (or, for example, rubber or brush seals), harvest hose 428, and male connector 444. Expanded flow insert 445 may be provided to prevent excessive pressure at the inlet of harvest pipe 442 and promote mass flow. Once the harvest vessel arrives and starts station-keeping over the shipping container 424 a tremie tube may be used to pour seed oysters 1 into the left-hand side of the twin funnel 439 and a female connector (which may be directly connected to a submersible pump, similar to purse seine vessels that use pumps for emptying seine nets, or connected to an onboard self-priming pump similar to the Transvac Silkstream fish pump (Environmental Technologies Inc., Washington, USA), which would prevent damage to harvested oysters, or a mining pump like the Godwin DPC 300 (Xylem Inc., Rye Brook, N.Y., USA)) may be simultaneously dropped onto the male connector 444 by a lift mechanism, such as, for example, a power block, sheave, pulley, or robotic arm, to name a few, to form a self-sealing connection for pumping oysters out of harvest hoppers 427. In embodiments, twin funnels 439 may be highly visible underwater and designed to be asymmetric so harvest vessel personnel can tell which end of the mint they are harvesting from. The funnel/sump shapes may provide some margin of error for pouring seed oysters and dropping the female connector for harvesting. As the harvest vessel moves from mint to mint in the farm the female connector may be kept below the waterline to avoid having to reprime the pump for every mint. This way the harvest vessel may be move rapidly from mint to mint. Pumped, harvested oysters may be immediately dewatered, graded, bagged and iced for just-in-time delivery to port for distribution (e.g., no warehousing as oysters are kept fresh in mints until harvest/sale). A purse seine vessel or super purse seine vessel is particularly well-suited to this mint harvesting operation because they are seaworthy, have a large stern deck, have rigging (power blocks, pulley, etc.) for manipulating the female connector/suction hose, and have refrigerated seawater systems. However, any stern-deck vessel (e.g., repurposed oilfield utility vessel) may be outfitted for the mint harvest operations. More details of the harvest vessel are described below in connection with FIGS. 13-15.

In embodiments, a large, centralized hopper may be provided to collect the product from multiple mints. For example, many mints may be arranged around a large central hopper. This may involve lifting of the large hopper onboard for harvesting instead of pumping oysters out directly from the system hoppers. In general, it is believed that keeping hoppers smaller minimizes risk of clogs and avoids the potential need for divers or hoisting of large hoppers onboard to remove clogs.

In embodiments, the one-way valve 443 or rubber or brush seals and various trims seals and packing seals around the system may be provided to prevent predators from entering the harvest hopper and/or the containment assembly 400. Harvest hose 428 and injection hose 429 may be fit with hose floats 446 to help them remain upright (in embodiments, both hoses are preferably already relatively neutrally buoyant). Harvest hose 428 may be, for example, a reinforced Kanaflex suction hose and injection hose 429 may be, for example, a layflat polyurethane hose, although other types of hoses may be used as described herein. Pump 430 may be, for example, a titanium submersible pump with upwards of 60,000 hours of rated saltwater operation. In embodiments, the pump 430 may be the only component requiring replacement during the life cycle of the system and thus is preferably located at the surface for easy servicing.

The harvest hopper 427 may be hung off the end of housing 424 using, for example, lashing bars and turnbuckle 447 which may be designed to engage with corner castings 436 in the same way as in normal intermodal transport (e.g., for lashing container stacks to container ships). Lashing bars and turnbuckles may leave enough room in corner castings 436 such that the twistlocks of a spreader crane can still pick up the shipping container 424 even with harvest hoppers 427 attached (e.g., the entire machine can be lifted off a vessel and installed in the seafloor in a single lift). In embodiments, insulating pads and/or coatings may be used to prevent galvanic corrosion between corner castings 436 and lashing bars 447 and between harvest hoppers 427 and shipping container 424. Lashing bars 447 may be adjustable in length so misalignment between injection pipe 441 and central shaft 440 may be easily accommodated and harvest hoppers can be quickly and efficiently hung off shipping container 424 using a hoisting device, such as, for example, a forklift. In this regard, shipping container and harvest hoppers may be shipped separately and quickly assembled before loading onto a ship for installation on the seabed offshore. Alternatively, in embodiments, harvest hoppers 427 may be hung on the ends of housing 424 using custom hinges that insert into the top and/or bottom of corner castings 436 and then secured using, for example, pins, lashing bars, turnbuckles, or combinations thereof. Load cells may be installed on bearing surfaces to measure hopper weight and provide a signal indicating an appropriate time for harvesting.

Figure 11A:
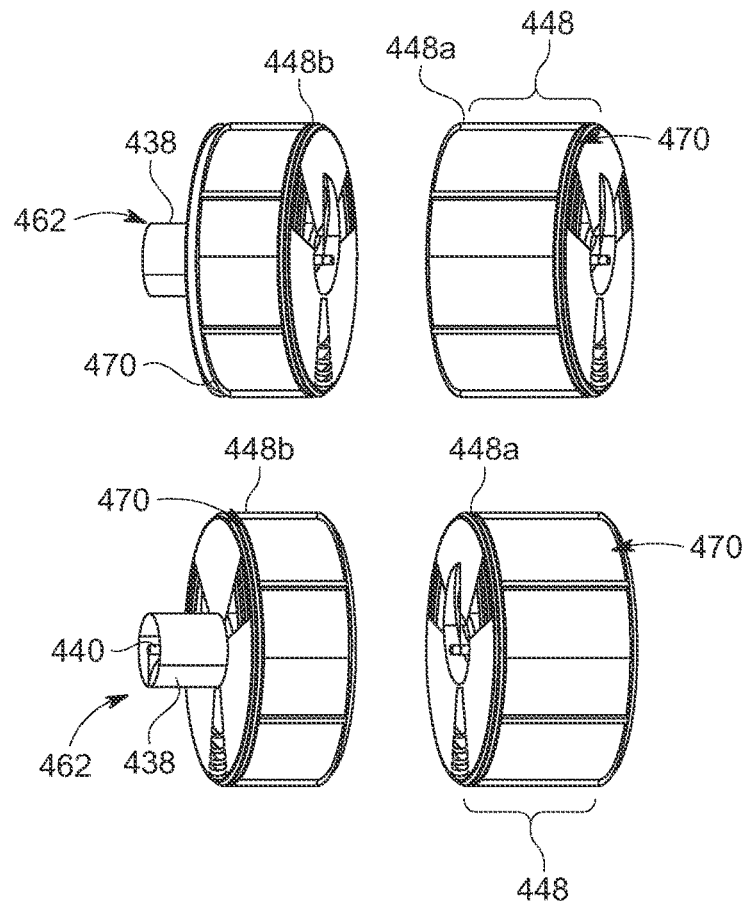
FIGS. 11A and 11B show a process of making a containment assembly according to an exemplary embodiment of the present invention.
Figure 11B:
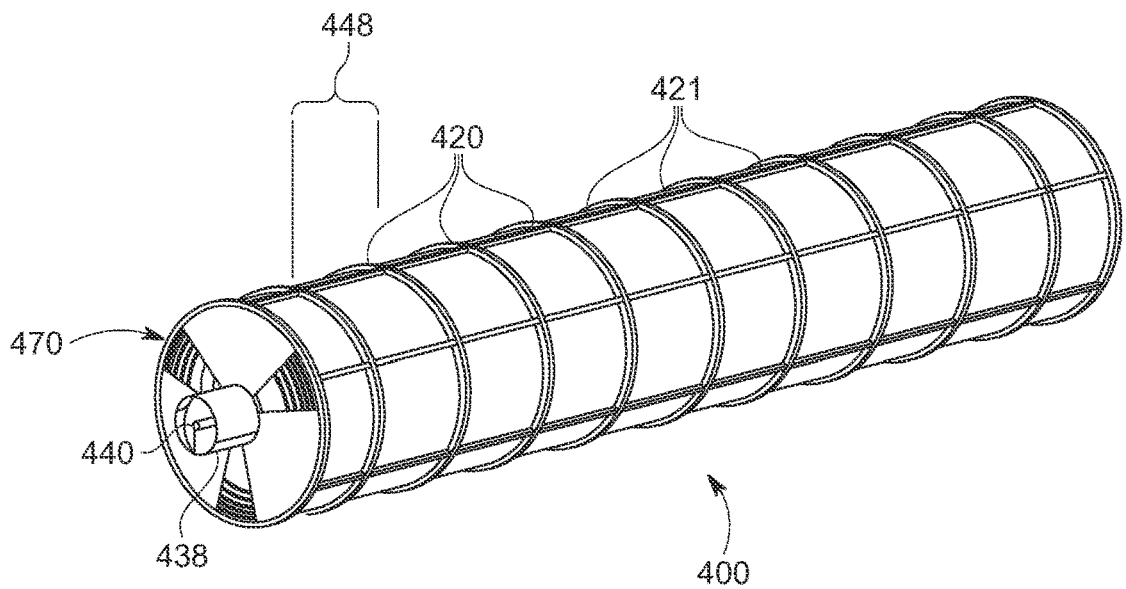

FIGS. 11A and 11B show a process of making the containment assembly 400 according to an exemplary embodiment of the present invention. Containment assembly 400 may be made up of lengthwise sections 448 that may be joined together inside housing 424 by, for example, welding the angle rings and bulkheads on both sides of every section 448 to form channel rings to rest on rollers 423. In embodiments, methods other than welding may be used to join the sections 448, such as, for example, bolt circle, torque couple friction or Oldham-style coupling, to name a few. In the present example, the first and last sections 448b may have outlets 438 attached and may be slightly shorter to allow the containment assembly 400 to fit inside the housing 424. For example, if a 40-foot shipping container is used for the housing 424, the containment assembly is preferably just under 40 feet in length. Other sections 448 may have additional angle rings added inline to provide mounting surfaces for components, such as, for example, drive sprockets, and ratchet pawls, to name two. Central shaft 440 may be divided between each section 448 and may mate together via male/female sockets and seals when the sections 448 are put together. Each bulkhead may be made up of two angle rings and two plates which when joined together between each section 448 form a channel ring and a plate of full thickness.

FIG. 11C shows the flow of oysters through containment assembly 400 in accordance with an exemplary embodiment of the present invention. Seed oysters 1 may be injected and evenly distributed through containment assembly 400 via central shaft 440 and settle to outmost compartment 401. When seed oysters 1 have grown to harvest size oysters 3 and remain in compartment 406, screw flight 418 may push them out through outlets 438. The screw flight 418 may be right-handed in one half and left-handed in the other half such that oysters on the left side of the containment assembly 400 are discharged through the outlet 438 on the left and oysters on the right side of the containment assembly 400 are discharged through the outlet 438 on the right.

Figure 12A:
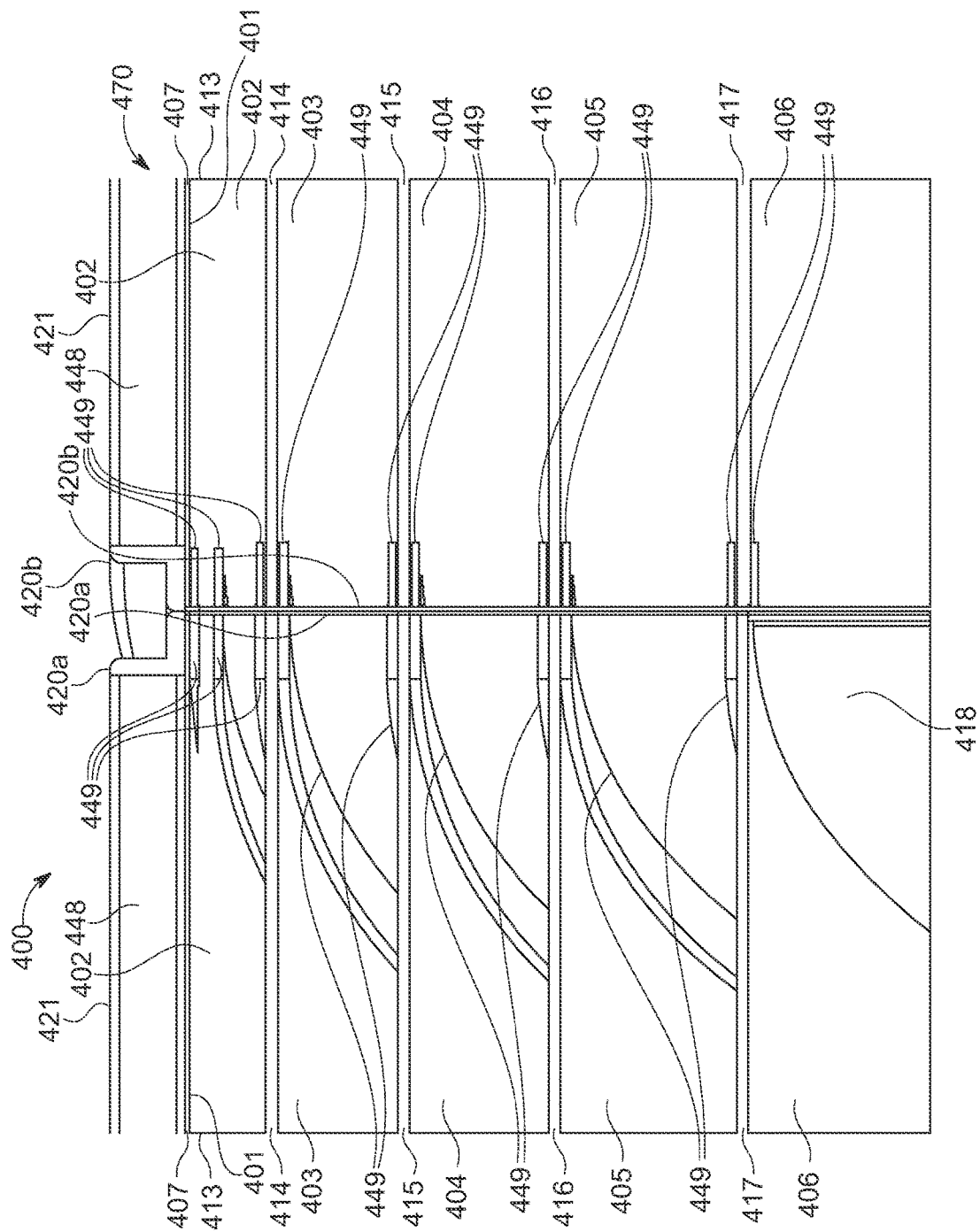
FIGS. 12A and 12B are schematic illustrations of a partial cross section of a containment assembly in accordance with an exemplary embodiment of the present invention.
Figure 12B:
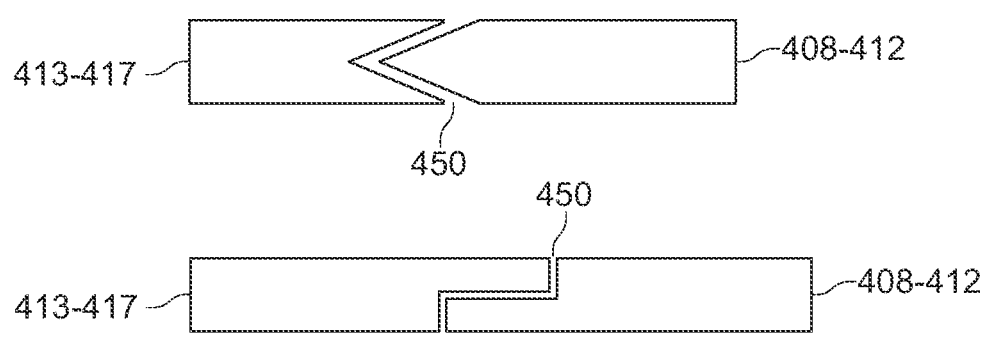

FIGS. 12A and 12B show a cross-section of a bulkhead 420 between two sections 448 of containment 400 in accordance with an exemplary embodiment of the present invention. Compartments 401, 402, 403, 404, 405, and 406 are separated by cylindrical enclosure 407 and ramps 413, 414, 415, 416, and 417 (walls 408, 409, 410, 411, and 412 are not shown in FIG. 12 because they are on the opposite cross-section). In the mass-manufacturable mint, all ramps 413, 414, 415, 416, 417 and all walls 407, 408, 409, 410, 411, 412 may be made of plastic material, such as, for example, high-density polyethylene (HDPE), polypropylene, and combinations thereof, to name a few, which may be marine grade and/or recycled material. In embodiments, the spiraling perforated sheets are a significant cost item for mints of any size, for example, upwards of 50% the cost of the mint described previously with reference to FIGS. 5-7, in the case where the mint is made with ⅛" perforated aluminum. The use of HDPE provides advantages, such as, for example, significant reduction in cost as compared to aluminum even for the same equivalent bending stiffness, reduced susceptibility to degradation in saltwater, and ability to be punched with larger holes (e.g., up to 2" diameter holes needed to sort harvest-size oysters) compared to aluminum which can only be punched with up to 1" holes and requires larger holes to be cut using lasers at very high cost (not suitable for mass-manufacturing). In order to constrain HDPE perforated sheets, bulkheads 420 of containment 400 may be provided with spiraling pockets formed by bar stock 449 into which may be inserted the ramps 413, 414, 415, 416, 417 and walls 408, 409, 410, 411, 412.

In a specific example, 3'-4'×15' perforated sheets may be used to form all ramps 413, 414, 415, 416, 417 and all walls 408, 409, 410, 411, 412. The perforated sheets may be pre-punched with holes of the desired size, heated in a large oven (e.g., forced convection or autoclave) up to ~350 degrees Fahrenheit, and drape-formed over a mold of the desired radius. Many walls and ramps may be formed at once by placing sheets on top of molds on multi-tier racks inside of a large oven for heat-cycling. In order to minimize or eliminate distortion of the sheet edges that might occur in this process, the sheet edges may be subjected to a final trim to ensure proper fit between bulkheads 420 and spiraling bar stock 449. In order to prevent longitudinal gaps between ramps and walls, longitudinal edges of perforated sheets may be trimmed to form mating edges 450 (male/female or stepped/lapped), as shown in FIG. 12B, or may be fused using heating plates (similar to HDPE pipe fusion). The rolled angle/channel rings and circular plates that make up bulkheads 420 may be welded on jigs and tied together by beams 421, thereby sandwiching ramps 413, 414, 415, 416, 417 and walls 407, 408, 409, 410, 411, 412 inside of the spiraling pockets formed by bar stock 449. Sections 448 may then be installed one-by-one on top of rollers 423 inside of shipping container 424 through cutouts in the container sides or through the container doorway (which may be still operational) using a hoisting mechanism, such as, for example, a telehandler, counterweight lift, or forklift, to name a few. Once aligned and resting on rollers 423, sections 448 can be welded, bolted, or otherwise coupled together. Paint on containers may be touched up, especially in areas where cutouts are made. Container losses from ships have provided the opportunity to observe container deterioration on the seabed and indicates exceptionally long-lived structural integrity due to the CORTEN/weathering steel used in shipping containers as well as the cold, low-oxygen, well flushed conditions on the seabed.

Instead of leaving containers as is, repainting them, or sealing them with an enamel, the CORTEN steel of the ISO containers may be weathered, which may require existing paint to be wire-brushed or sand/bead-blasted off so the containers can be weathered outdoors over several days or weeks. Weathered CORTEN steel would survive in saltwater and would eliminate the need for careful/costly painting of all surfaces, but the containers must be weathered before installation because the stable oxide layer cannot form once the steel is already in saltwater. Weathering would also eliminate the controversy around toxicity of various paint options.

In embodiments, since plastic perforated sheets retain their heat/formability for several minutes, perforated sheets may be heated in an oven on densely packed flat racks and then pulled over drape molds after being removed from the oven. Drape molds may be metal sheets supported by wooden frames with an adjustable radius of curvature.

While mint assembly may be done in a manufacturing assembly line, mint assembly may also be done in open fields/lots or even quayside with hoisting mechanisms, such as for example, telehandlers and forklifts using factory-made perforated sheets and bulkheads. Such containers may be loaded directly onto a barge or self-unloading container vessel or, in remote locations without port facilities, loaded onto large landing craft carriers directly on the beach for installation offshore. Because road transport is avoided, this would allow construction of mints with very large diameters. For farm installation, the vessels may be provided with a crane, or a separate barge crane may be provided.

It should be appreciated that the material used for the bulkheads 420 is not limited to aluminum, and other materials, such as, for example, plastic, other types of metals, and combinations thereof, to name a few, may be used without departing from the spirit and scope of the present invention. In embodiments, oyster mint farms may be placed far enough offshore (e.g., 12 nautical miles or more) so that only federal permits may be required as opposed to requiring both federal and state/local jurisdiction permits (although location within state waters may be necessary given water depth of mints should not exceed 20 m). Further, in embodiments, oyster mint farms may have minimal impact on the environment and marine life because, for example, there is no need for onsite assembly, quick and efficient farm construction can happen in a very short period of time (mints may be merely picked from a vessel's deck and placed on the ocean floor), relatively little space needs to be occupied, machine density is high, and less restrictive siting requirements means mints can take up less sensitive habitat. In comparison, offshore wind farms, for example, are located in deeper water, require extremely noisy and years-long construction, and have thin, but very strong, lines spanning large distances, thereby having serious implications for marine life. Mint tethers 432 may be significantly weaker than wind farm mooring cables and therefore pose less environmental risk, as well.

In embodiments, individual mints or mint farms may be located at an ocean depth of, for example, 3 m, 10 m, 15 m, 20 m, anywhere within a range of 3 m to 20 m, less than 3 m, or greater than 20 m, to name a few. Mint farms may be placed nearshore to act as breakwaters and artificial reefs to prevent stormwater overrun and coastal erosion. In this regard, electric fields may be applied to the mint container frames in order to accelerate the growth of coral and other fauna on them.

In a specific example, a billion oyster per year farm might require 2,000-4,000 40 ft mints and take up approximately 20-80 acres of seabed. Flux of water through this footprint, assuming a 5:1 farm aspect ratio, may be upwards of 20 billion gallons per day and therefore, assuming that an adult oyster filters an average of 20 gallons per day, nutrient availability is not a concern. Farm installation may be a simple matter of placing mints on the seafloor with adequate spacing to allow water flow and to easily tell adjacent mints apart (e.g., 50% packing fraction). Lanes may be provided at 2-3 times the length of the harvest vessels to allow passage/maneuvering. Farms may be rapidly constructed by placing large numbers of preassembled mints on a vessel with a spreader crane and DP2 (e.g., a dynamic positioning system rating of DP2) station keeping ability and picking/placing each container into place on the seabed. No decommissioning may be required because mints are either refurbished or left as artificial reefs and/or dive sites for perpetuity. Compressible seabed or otherwise non-loading-bearing strata and other risks such as frequent benthic storms/plumes/solid precipitant may cover parts of mint farms over long periods of time. In this regard, in embodiments, mints may be lifted out of accumulating sediment and placed back on top or moved to other areas. Maintenance, repairs, and/or refurbishment of mints may happen in situ by hoisting a mint onboard a vessel, performing work, and immediately replacing the mint back on the seafloor. Repairs may include, for example, replacing rollers/bushings, sprockets/chains, and/or motors/fittings, to name a few. The only regular expected maintenance may be replacing the titanium pumps 430 after a predetermined period of operation, such as, for example, 60,000 hours of operation. Refurbishment might involve replacing aluminum bulkheads, which may warrant transport back to land.

In embodiments, mints may be placed on land inside structures, such as, for example, warehouses or artificial canals in order to grow fresh oysters in landlocked locations or to better control growing conditions (e.g., temperature, salinity, nutrients, etc., to name a few), for example in order to grow exotic species of oysters close to demand centers. Such mints may have additional costs, such as, for example, costs associated with warehouse construction, large pumping/plumbing installations, heating, water treatment, salt (for a land-locked closed systems), land costs, additional permitting/monitoring, and bioreactors for growing food, to name a few, as compared to regular offshore mint farms where operational growing costs are minimal. Thus, warehouse mint oysters may be produced at a cost above the current market average. Such a use case for the mint preferably must be able to sell oysters for a premium because, for example, the oysters are exotic and/or because they are grown for a landlocked demand center that does not otherwise have access to fresh oysters. In a warehouse scenario, mints may be stacked 2-3 high (e.g., above ground in air) and nutrient rich water may be pumped through and caught in catch basins for recycling, cleaning, or for disposal (depending, for example, on whether the system is making its own saltwater or using seawater).

In embodiments, marine growth may be a major concern for the mint as too much marine growth could sap nutrients, cover perforations, and/or disrupt mechanisms. In this regard, oyster tumbling action may be enough to kill any larvae that attaches to the inside walls of the mint or to the oysters themselves before the growth can grow to a more resilient size, as long as the mint is tumbled often enough. Even if the mint is only rotated once a week for sorting, for example, the mint may still be rotated back and forth daily with net zero revolution for the sole purpose of cleaning marine growth. Marine growth on the bulkhead rings is limited to the flanges of the channel rings and angles rings because nothing can grow where the wheels tread/make contact. Marine growth on the struts, ring flanges, and container/housing does not matter as such growth does not impede any functions of the mint. Marine growth on the outside of the outermost perforated sheet has a negative effect because holes are very small (e.g., ~1/16" diameter; thus easily covered by growth) and easily colonized by marine growth larvae. This surface may be kept clean by simply placing scrapers or stationary brushes inside the container frame of the mass-manufacturable mint (e.g., metal or plastic or horsehair) that contact the outer wall of the containment assembly and clean larvae off as the containment assembly rotates (microscopic larvae that deposit will not have time to attach or grow because the entire outside surface of the containment assembly is touched by the brushes at least once for every rotation of the containment assembly). Brushes may also be used to clean roller chain, wheels, and other surfaces in a similar way. Internal pressurization of the containment assembly and flow through the outermost holes may be provided to help keep them clear. Directed jets inside the containment assembly may be provided to help keep specific surfaces clean, such as those surfaces that are not in contact with tumbling oysters or brushes/scrapers. Coatings, such as, for example, PTFE coatings may be applied on parts of the mint, such as, for example, on the outside of the outermost perforated layer, to prevent marine growth, as ocean currents will rip marine growth off the containment assembly once the growth reaches a critical size and drag is too great compared to friction/adhesion between the marine growth and the PTFE coating (this is a method used to prevent marine growth on oil containment booms).

In embodiments, for large enough mint farms it may be most cost-effective to provide a subsea high-voltage cable that brings power into a central transformer and/or distribution hub.

As previously described, in embodiments, the sun/UV exposure provided by tidal estuaries during low tide may be mimicked in mints by providing full spectrum lamps or distributed LED strips throughout the compartments. This may also prevent marine growth and strengthen oyster shells.

In embodiments, mints may be individually loaded on ISO trailers for road transport. Modifications (e.g., reinforcements) may be made to the mint as necessary to certify the mint for intermodal transport such that the mint can be stacked with ordinary container cargo onboard ocean-going container ships.

In embodiments, instead of or in addition to relying on gravity to distribute seed from the central shaft, components, such as, for example, radial piping or bulkhead cavities may be provided to carry seed directly to the outer layer of the containment assembly. In this regard, in order to accommodate such components, cutouts may be formed in perforated sheets and/or bar stock spiraling pockets to allow piping to pass through and/or bulkheads may be made hollow.

In embodiments, the mint may have a large central hopper inside the container frame with a single pair of hoses, in which case the containment assembly may be split in half to accommodate the hopper in between the two halves. It would allow only one harvest step per mint, but a larger hopper is not as efficient or reliable for mass-flow as two smaller hoppers.

Figure 13:
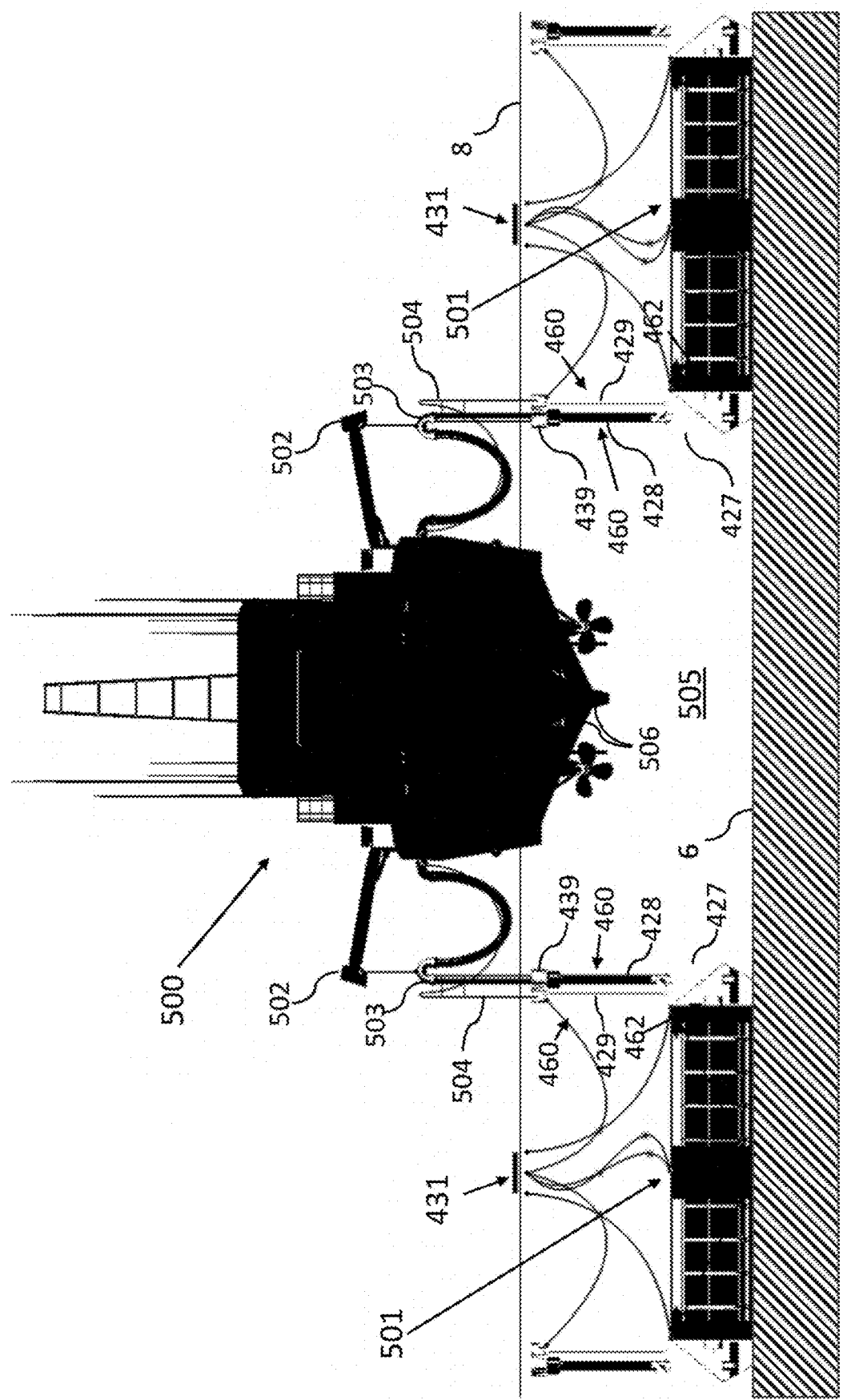
FIG. 13 shows a mint harvest vessel harvesting simultaneously from two rows of mass-manufactured mints in accordance with an exemplary embodiment of the present invention.

FIG. 13 shows a mint harvest vessel 500 harvesting simultaneously from two rows of mass-manufactured mints 501 in accordance with an exemplary embodiment of the present invention. Cranes 502 may be used to lower harvest hoses 503 and seed injection hoses 504 onto twin funnels 439, which pass through injection hoses 428 and injection hoses 429 to harvest hoppers 427. Harvest hoses 503 and seed injection hoses 504 may have slack to allow recovery onto harvest vessel 500 and a large range of adjustment to accommodate movements of the crane 502, such as, for example, rotation, booming up/down, telescoping, and reeling in/out, to name a few. A lane 505 may be left between rows of mass-manufactured mints 501 to allow harvest vessel 500 to traverse through the mint farm. Harvest vessel 500 may be provided with bow thrusters 506 for dynamic positioning accurately over each mint location, and position may further be aided with GPS. In embodiments, harvest vessel 500 may harvest from approximately 50-100 mints in a working day and assuming every mint is harvested every 10 days, each pair of hoppers may yield 10,000 oysters per harvest and harvest vessel 500 may hold upwards of 1,000,000 oysters onboard. Harvest vessels 500 may be capable of harvesting a billion or more oyster mint farm (e.g., 2,000-4,000 40 ft mints). It should be appreciated that the number of mints in each farm, the harvesting periods and the harvesting capacity of the harvest vessel 500 are not limited to those examples provided herein, and these parameters may be varied without departing from the spirit and scope of the present invention.

Figure 14A:
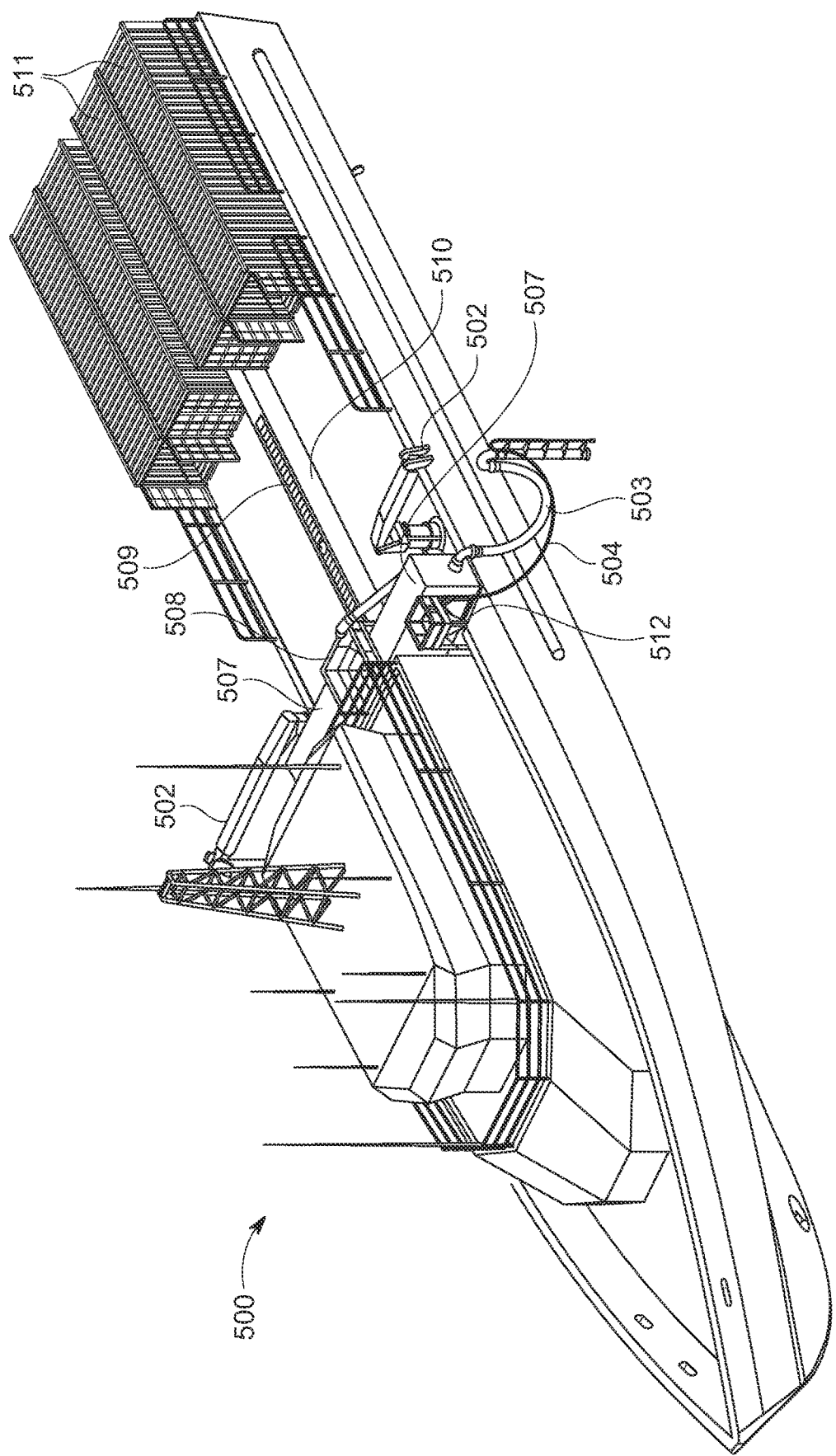
FIGS. 14A, 14B and 14C show several detailed views of a deck spread a harvest vessel in accordance with an exemplary embodiment of the present invention.
Figure 14B:
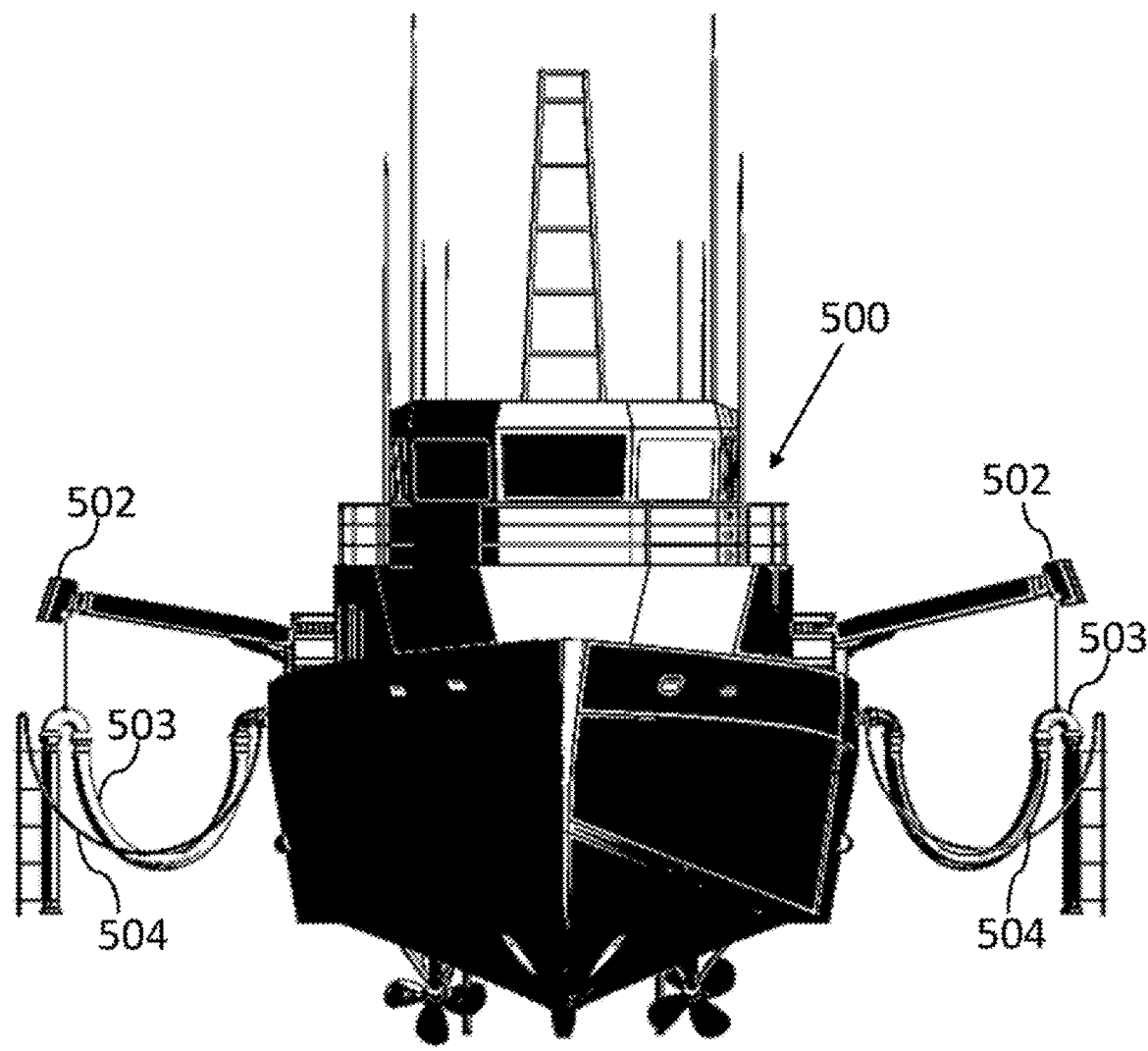
Figure 14C:
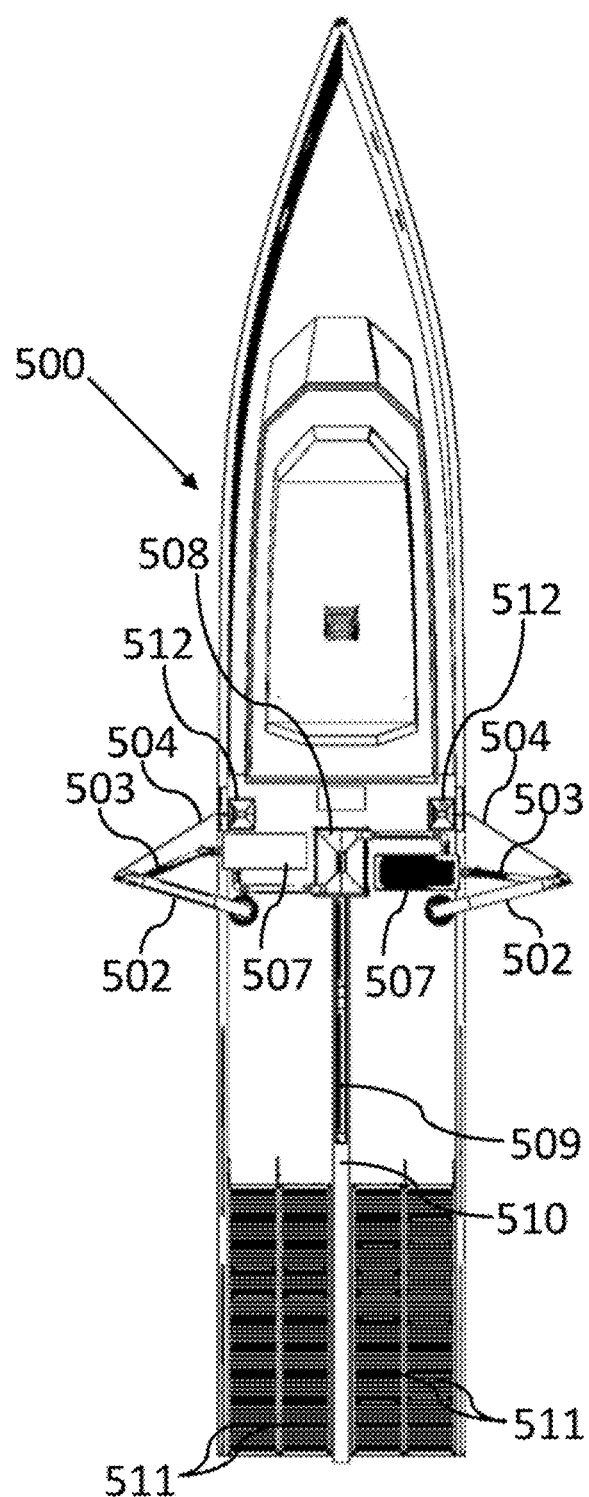

FIGS. 14A-14C show several detailed views of a deck spread of the harvest vessel 500 according to an exemplary embodiment of the present invention. In addition to cranes 502, harvest hoses 503, and seed injection hoses 504, the deck spread may include a variety of other components, such as, for example, pumps 507, deck hopper 508, conveyor 509, spillway 510, reefer containers 511, and seed oyster hopper 512, to name a few. Harvest hoses 503 may feed into the suction of pumps 507. Pumps 507 may be, for example, an industrial mining/solids-handling/dewatering pump or a venturi/jet/fish pump having a flow rate in the range of, for example, 1800-5000 GPM. Pumps 507 may discharge into deck hopper 508, which dispenses oysters onto conveyor 509 and water into spillway 510 that may be discharged off the stern of the harvest vessel 500. Oysters may be sorted on conveyor 509 manually (e.g., using about 20 workers) or automatically using, for example, optical/compressed air graders into market-ready boxes and/or bags, palletized and loaded into reefer containers 511. Dead or subpar oysters may remain on conveyor 509 and jettisoned through spillway 510. Reefer containers 511 may run off power from harvest vessel 500 and when harvest vessel 500 returns to port, reefer containers 511 may be immediately loaded onto semi-trailers for transport to distributor. Seed injection hoses 504 may be connected to seed oyster hopper 512 and seed oysters may be dispensed through seed injection hoses 504 into twin funnels 439 via a mechanism, such as, for example, a jet pump, positive displacement pump, flushing mechanism, flexible screw conveyor, a cable conveyor, a disc conveyor, a drag conveyor, a chain conveyor, a tubular conveyor, or combinations thereof, to name a few, so that the appropriate amount may be accurately and gently dispensed at each mint.

Figure 15A:
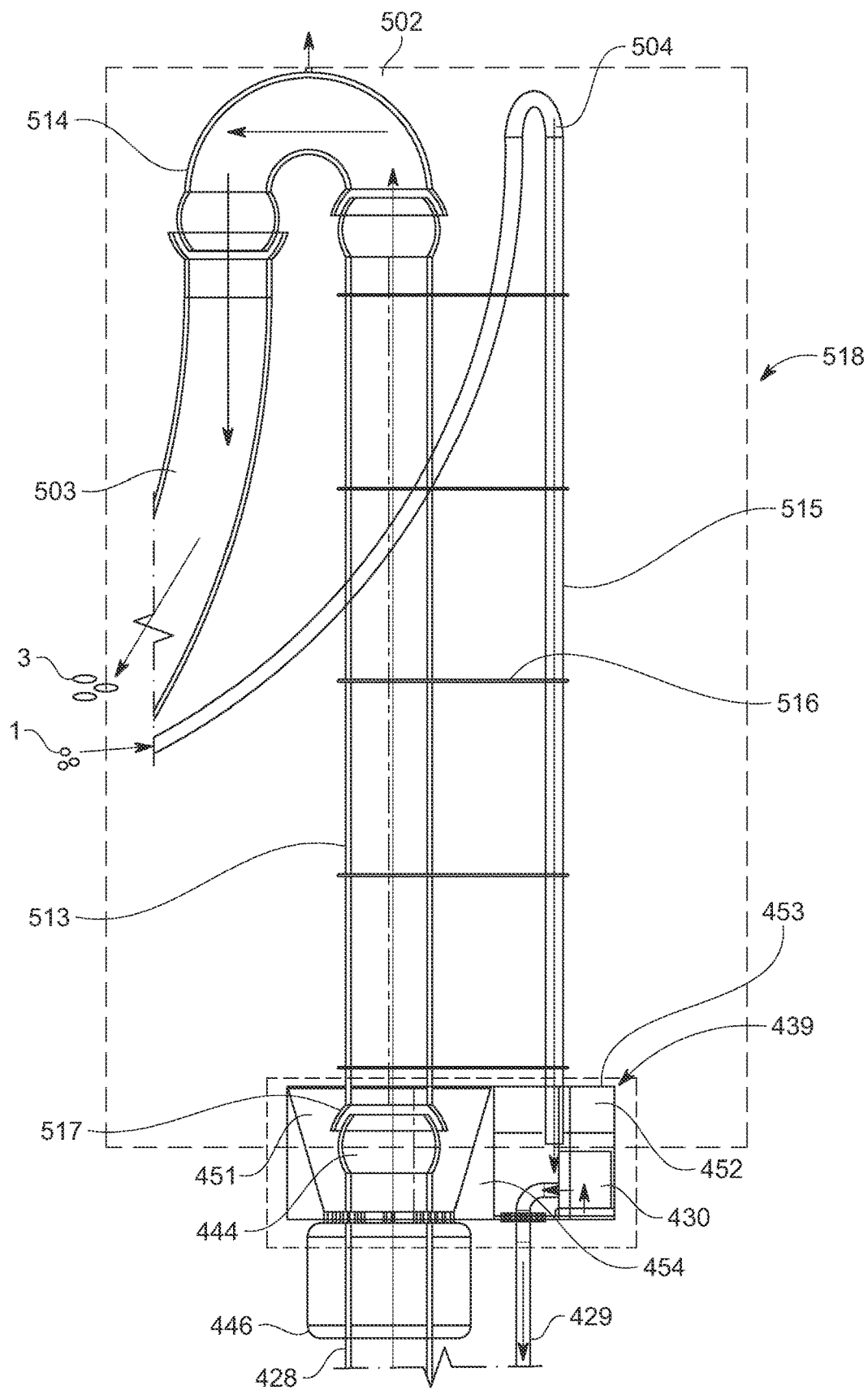
FIG. 15A shows a detailed view of the connection assembly between a harvest hose and a seed injection hose of a harvest vessel with a twin funnel according to an exemplary embodiment of the present invention.

FIG. 15A shows a detailed view of the connection assembly, generally designated by reference number 518, between the harvest hose 503 and the seed injection hose 504 of the harvest vessel 500 with the twin funnel 439 according to an exemplary embodiment of the present invention. Harvest hose 503 may be connected to a first vertical end-section 513 via a 180-degree pipe bend 514. The connection assembly 518 may be suspended from crane 502 by the pipe bend 514. Seed injection hose 504 may in turn mate with a second vertical end-section 515. First vertical end-section 513 and second vertical end-section 515 may be joined by coupler 516. Twin funnel 439 may be split into two halves. One half of the twin funnel 439 may provide an upward facing cone 451 to facilitate reliable and quick mating of female connector 517 with male connector 444 to create a self-sealing pumping connection to evacuate harvest-ready oysters 3 through harvest hoses 428 from harvest hoppers 427. The other half of twin funnel 439 may provide a sump 452 inside which sufficient downward fluid flow may be created by pump 430 to draw-down seed oysters 1 dispensed through seed injection hose 504 and vertical end-section 515 such that seed is taken in by pump 430 and injected into mint through injection hose 429. Radial brushes and/or leaves 453, for example, may be provided to prevent oyster seeds, which can sometimes exhibit positive buoyancy, from floating out of sump 452. Twin funnel 439 may be mass-manufactured using, for example, roto-molding such that the interior 454 can be foam-filled and/or sealed and act as additional buoyancy to hose float 446. Suction may be broken between female connector 517 and male connector 444 by lifting vertical end-sections 513 and 515 using crane 502.

Figure 15B:
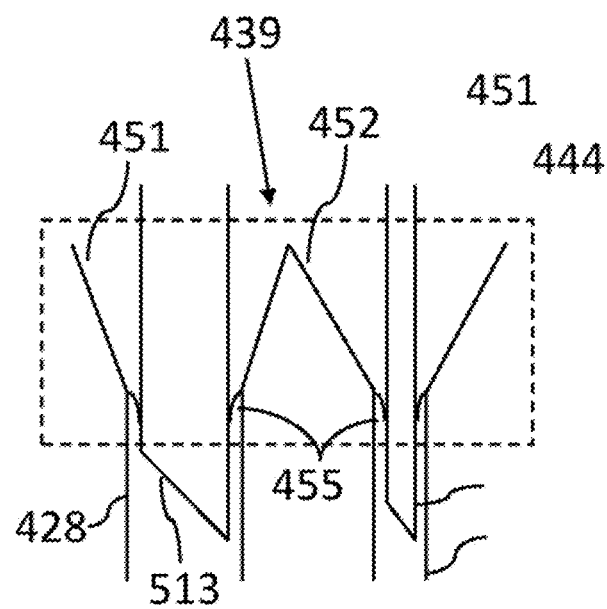
FIG. 15B shows a detailed view of the connection assembly between a harvest hose and a seed injection hose of a harvest vessel with a twin funnel according to an exemplary embodiment of the present invention.

It should be appreciated that the connection assembly 518 is not limited to the description provided herein, and embodiments of the present invention may include modifications of the connection assembly 518 without departing from the spirit and scope of the present invention. For example, while connections between harvest hose 503, pipe bend 514, and vertical end-section 513, etc. are pictured as spherical camlock fittings, which provides some angular compliance in these joints that may allow freer movement, rigid bolted connections may also be used. Similarly, vertical end-sections 513 and 515 may be flexible hose or rigid pipe. As shown in FIG. 15B, instead of using male/female connector on the harvest hose and the sump with pump for seed injection, the twin funnels may include two individual cones (e.g., shear spun from stainless steel cones) that guide beveled pipe ends (from the harvest vessel) into the harvest and seed injection hoses a certain distance to create a sufficient seal for pumping. The apex of each cone could comprise rubber or brush seals 455 that prevent predators from entering the hoses and help create static seals against pipes from harvest vessel.

In embodiments, because vertical end-sections 513 and 515 may be coupled, the connection assembly 518 is preferably placed in an appropriate angular orientation such that vertical end-section 513 can enter upward facing cone 451 and vertical end-section 515 can enter sump 452 at the same time. Besides accurate harvest vessel 500 positioning/station-keeping and the margin of error provided by oversizing upward facing cone 451 and sump 452, connection assembly 518 may be provided with rotational control by, for example, tag lines, push/pull arm(s), or by adding a rotating wrist to crane 502, to name a few. In embodiments, coupler 516 may be rotated and fixed at any angle on vertical end-section 513 (manually or automatically by, for example, motor/gearbox between vertical end-section 513 and coupler 516) such that any angular bias can be corrected such that the plane through the central axes of vertical end-sections 513 and 515 is approximately perpendicular to the port/starboard sides of the harvest vessel 500.

Oysters have a constantly varying width that may cause them to temporarily wedge in holes at their max width, however, the weight of other oysters tumbling over them may eventually force them through. In embodiments, drafting holes outward slightly (e.g., hole diameter increasing slightly from inner most end to outer most end of each wall/ramp) may also help reduce wedging because contact between oysters and holes is only at two points, rather than line contacts, and only a small displacement is required to punch wedged oysters through the holes due to the holes ability to expand, particularly in the case of the walls and ramps being made of HDPE or other flexible material that allows localized stretching and/or warping around the holes. Further, bending of sheets warps circular holes slightly and makes them slightly elliptical and slightly drafted, which may reduce risk of oysters getting stuck in the holes if their width is only slightly larger than a nominal hole diameter.

Jamming may occur if the containment assembly is not rotated often enough and oysters are allowed to grow for an extended period of time in one compartment. Thus, in embodiments, the containment assembly is preferably rotated often enough, or at least agitated, to prevent such jamming (e.g., as often as is possible without shrinking the oysters).

More specifically, in embodiments, the containment assembly is preferably rotated as frequently as possible to prevent jamming and/or compartment overfilling and to expel harvest-size oysters as quickly as possible, which in turn may minimize required size of the innermost compartment and maximize space for growing oysters. Without being bound by theory, it is believed that the limiting constraint is that rotating too often may shrink the size of the oysters by removing shell faster than they can grow. In embodiments, rotating weekly may be considered appropriate for capturing the growth progress of certain types of oysters, such as, for example, *Crassostrea virginica* oysters with an 18-month growth cycle, but frequency may be as high as daily or as low as monthly depending on species and growth conditions. In embodiments, containment assembly may be rotated back and forth, without any forward progress, in between rotations, to prevent jamming, and this may extend the allowable period between full rotations.

In embodiments, while rotating, the containment assembly preferably moves in an oscillating motion as it gradually makes forward progress. For example, if oysters take up approximately a 120-degree sector inside the containment assembly and the average slip/roll/cataract angle of the oysters is 30-degrees then the containment assembly may rotate 2×(60°+30°)+(forward step size), then back 2×(60°+30°)+(backward step size) and repeat until a full revolution is made. In embodiments, the total step size of the containment assembly movements is the difference between the forward rotations and the backward rotations (forward step size—backward step size). As the total step size of the containment assembly approaches 0, the sorting efficiency may approach 100% because oysters are sorted across a greater length of perforated sheet. In embodiments, the step size is preferably as small as possible such that the control system can still monitor and ensure forward progress is being made, but not so small that the rotational frequency cannot be achieved because rotational periods interfere.

In embodiments, encoders may be used to measure the rotations of the containment assembly directly to ensure drift/slip in motors and/or transmission does not affect forward progress (especially if rotations are slow/take a long time or if hydraulics or friction drives, like wheels and belts, are used). With manual control, a max step size of, for example, 30-degrees may be sufficient at 1 rpm containment assembly speed, however, for containment assemblies that are autonomously controlled, a step size as low as, for example, 1-degree, or even lower, may be achieved given encoder resolutions are measured in micrometers/millimeters and containment assembly circumferences are measured in tens of feet. Encoders may be, for example, optical, magnetic, capacitive, inductive, or eddy current-based, to name a few.

Without being bound by theory, containment assembly speed selection may be a component cost trade-off between generation (e.g., grid power or solar panels), storage (e.g., batteries or hydraulic accumulators), primary movers (e.g., pumps/motors), and, to a lesser extent, transmission/gear reduction/controls (e.g., roller chains, gear boxes, encoders). Containment assembly rotation is preferably as slow as possible to minimize the power required (e.g., fewer solar panels and smaller hydraulic pumps) but, again without being bound by theory, this optimization is ultimately constrained by the rotation frequency requirement (daily, weekly, monthly) and/or the efficient operating ranges of the primary movers that can provide the needed torque.

In embodiments, the containment assembly accelerations may be made as large as possible in order to reduce friction and help oysters flow. In this regard, hydraulic cylinders may be used to accommodate the shock loads associated with higher accelerations.

As with all bulk materials, particularly with particles of the same approximate size, oysters within the containment assembly may exhibit bridging or stable arch formation. Thus, in embodiments, the gaps between walls and ramps are preferably large enough to prevent this from happening (e.g., ~3-5× the width of the oyster-size in each compartment).

In embodiments, the torque required to rotate the containment assembly may be conservatively calculated by multiplying the submerged weight of oysters in each compartment by the average radius of each compartment. For example, for a 4 ft diameter×8 ft long containment assembly with 10,000 oyster holding capacity (2,000 in each compartment), the torque requirement is ~15,000 in-lbs. As another example, for an 8 ft diameter×40 ft long containment assembly with 300,000 oysters (60,000 in each compartment), the torque requirement is ~1,000,000 in-lbs. Without being bound by theory, it is believed that this torque requirement may never be reached because oysters slip/tumble before the center of submerged oyster mass reaches the maximum moment arm. In embodiments, factors of safety (e.g., ~2) may be used and the preferred transmission systems (e.g., roller chain, drive wheels, etc.) may provide deep gear reduction at the containment assembly to reduce torque requirement on the motor(s).

In embodiments, the power train for the containment assembly may include, for example, a roller chain (e.g., stainless, coated, sealed pin-ends, to name a few), a drive belt (e.g., flat reinforced/metal, vee, grooved, cogged/timing belt, to name a few), drive wheel (e.g., solid polyurethane wheels, solid stainless wheels, solid aluminum wheels with various coatings and textures, to name a few), a gear drive (e.g., spur, helical, etc.), a direct drive (e.g., with gear box, e.g. planetary, worm, spur, helical, bevel, etc.), a ratchet and pawl, hydraulic cylinders, retracting clevis pins, strand-jack/rail-jack/wedging force pads (e.g., hydraulic cylinders wedge onto strand or rail or flat flange), to name a few. In embodiments, containment assembly may be driven and hung from, for example, a roller chain, drive belt, and/or hydraulic cylinders (combining support and transmission).

In embodiments, mints may be designed to maximize the holding capacity of oysters by, for example, maximizing internal volumes, use of internal volumes, apportionment of respective oyster sizes, flow characteristics, etc., as holding capacity is one of the most important variables (along with oyster growth rate, machine cost, service lifetime) affecting return on investment (ROI). However, in embodiments, without being bound by theory, the best practice for reducing risk and maximizing reliability may be to underfill mints with the minimum number of oysters required to meet an ROI target (depending on the business plan chosen). Over time, the envelope can be pushed (e.g., from 30% circular sector to not more than 50% circular sector of the containment assembly volume).

Figure 16A:
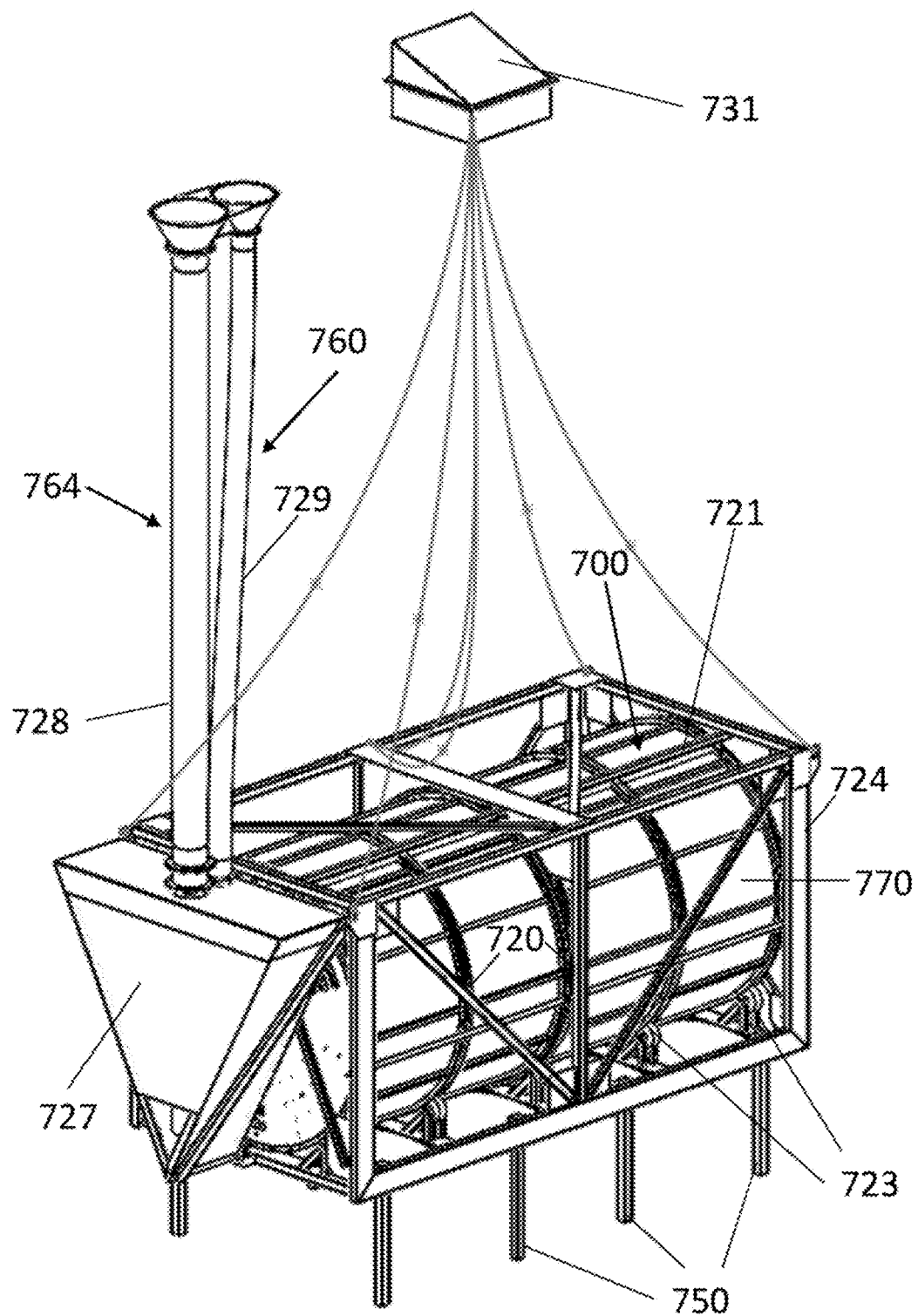
FIGS. 16A-16B illustrate an automated oyster maturation system according to exemplary embodiment of the present invention.
Figure 16B:
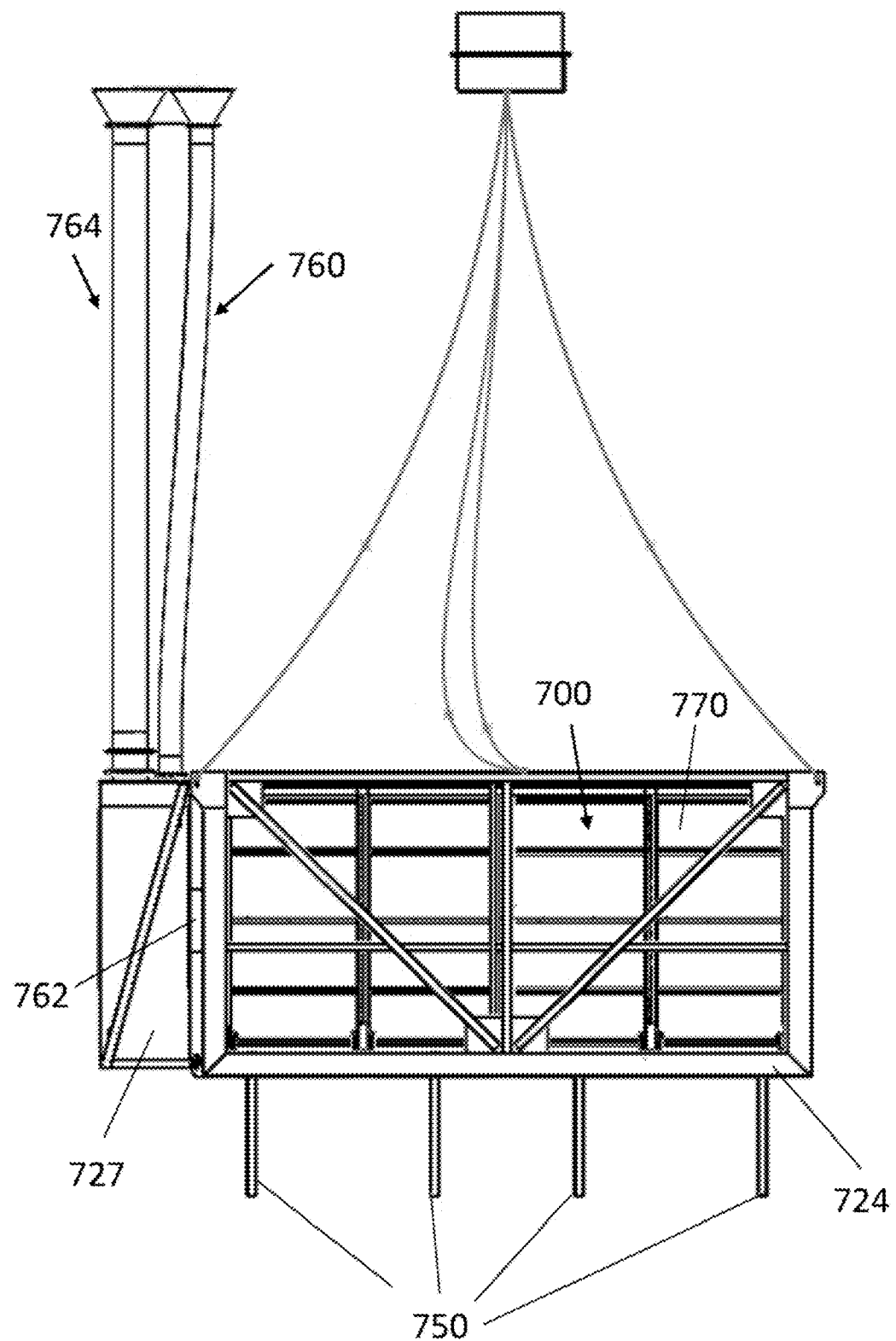

FIGS. 16A-16B illustrate an automated oyster maturation system according to another exemplary embodiment of the present invention. It should be appreciated that the prior exemplary embodiments of the inventive oyster maturation system described above with reference to FIGS. 5-15 may have the same or similar components as that of the present exemplary embodiment, so that more detailed descriptions provided herein with reference to the present embodiment may be applied to the prior exemplary embodiment and vice versa without departing from the spirit and scope of the present invention.

Specifically, FIG. 16A is a schematic illustration depicting a perspective view of an automated oyster maturation system in accordance with an exemplary embodiment of the present invention, and FIG. 16B is a schematic illustration depicting a side view of an automated oyster maturation system in accordance with an exemplary embodiment of the present invention. As in the previously described exemplary embodiments, the system of the present embodiment may include a containment assembly 700 having an outer enclosure 770, which may have, for example, a cylindrical shape. Also, as in the previously described exemplary embodiment, containment assembly 700 may include bulkheads 720 connected by beams 72 land may sit on rollers 723 inside of a housing 724. Although the housing 724 is shown having an open frame structure, it should be appreciated that the housing 724 may have a closed-frame structure or may be a shipping container, as described in relation to previously-described exemplary embodiments.

As in previous embodiments, the system in accordance with the present exemplary embodiment may include a hull 731 that floats at the surface and houses components, such as, for example, solar panels, batteries, PLC(s), hydraulic accumulator, hydraulic pump, radio modem and other electronics necessary for telemetry, controls, and communication, to name a few. Hull 731 may be secured by tethers 732 to housing 724 and electric cables and hydraulic cables may run between the hull 731 and housing 724.

As in the previously-described exemplary embodiments, the system includes an inlet assembly 760 that includes an injection hose 729 and pumps configured to inject seed oysters into the containment assembly 700, an outlet assembly 764 that includes an ejection hose 728 and pumps configured to transport harvest-ready oysters to, for example, collection vessels, and an ejection assembly 762 configured to eject harvest-ready oysters from the containment assembly 700. The ejection hose 728 and injection hose 729 may extend from a harvest hopper 727. In embodiments, the ejection hose 728 may be coupled with the injection hose 729 by twin funnels 739, which prevents the hoses from twisting together. Although the system in this exemplary embodiment includes only one inlet assembly 760, only one outlet assembly 764, only one ejection assembly 762, and only one hopper 727, it should be appreciated that the system may include more than one of each of these components, as disclosed in relation to previously-described exemplary embodiments.

In embodiments, the hopper 727 receives harvest-ready oysters ejected from the ejection assembly 762. As in previously-described embodiments, harvest-ready oysters may be ejected from an inner-most compartment of the containment assembly 700 by one or more screw flights into the hopper 727.

In embodiments, legs 750 may extend from the bottom of the housing 724. The legs 750 may be permanently fixed to the housing 724 so that the legs 750 and housing 724 form a unitary structure, or the legs 750 may be removable attached to the housing 724. If the legs 750 are removable attached, the system may be delivered to a site without the legs 750 attached, and then the legs 750 may be attached to the housing 724 just prior to the system is lifted overboard or otherwise submerged. In embodiments, the legs 750 may be removably attached to the housing 724 by components, such as, for example, pins, screws or rods, to name a few. In embodiments, the legs 750 may be attached to one another by a frame (not shown), so that the legs may be more easily attached to the housing 724. This would provide a modular arrangement in which all of the legs 750 may be quickly attached to or removed from the housing 724 using the frame. For example, for attachment, the frame may be aligned with the housing 724 so that the legs 750 may be placed in proper position relative to attachment points on the bottom of the housing 724.

In embodiments, the legs may be configured to keep the system a certain distance from the seafloor to prevent debris from burying the system. For example, the legs 750 may have suitable lengths to keep the system within a range of, for example, 1 to 5 feet off the seafloor, 2 to 3 feet off the seafloor, or any other suitable distance off the seafloor. In embodiments, the legs 750 may be piles, such as, for example, friction piles or end-bearing piles or have pedestals/footings that sit on the seafloor.

Figure 17A:
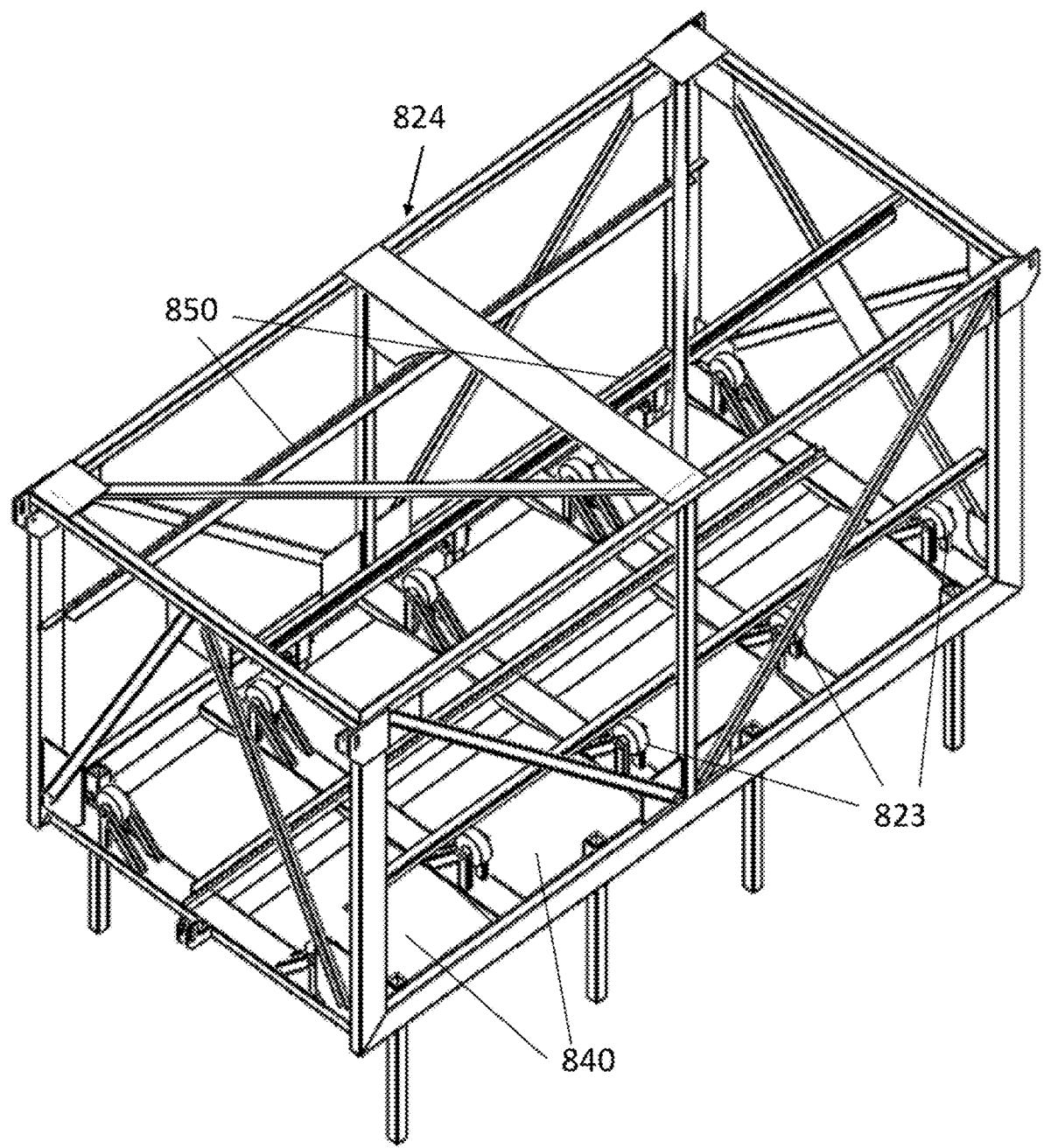
FIGS. 17A-17B illustrate an automated oyster maturation system in accordance with an exemplary embodiment of the present invention.
Figure 17B:
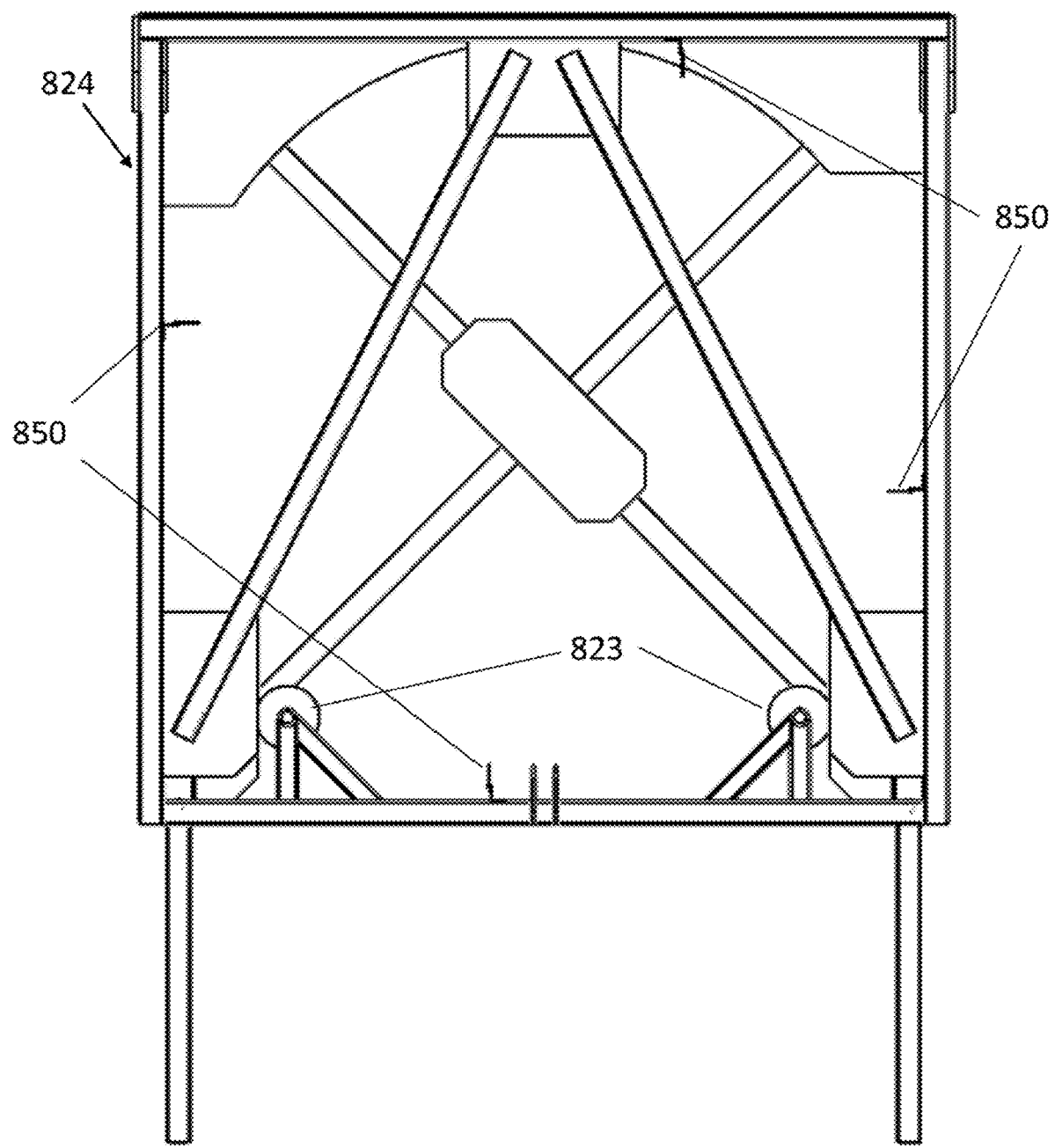

FIG. 17A is a schematic illustration depicting a perspective view of a housing 824 of an automated oyster maturation system in accordance with an exemplary embodiment of the present invention, and FIG. 17B is a schematic illustration depicting a side view of the housing 824. As in previously-described embodiments, the housing 824 may be provided with legs 850, rollers 823 may be disposed within the housing 824 so that a containment assembly may rotate within the housing 824, and brushes or scrapers 860 may be arranged around the inside of the housing 824 to make contact with the containment assembly as the assembly rotates to remove marine growth and debris off the assembly. In embodiments, the bottom floor of the housing 824 may be made up of a number of panels 840. Each floor panel 840 may be shaped with a convex curvature relative to the seafloor to prevent the frame from sinking into the seafloor. In embodiments, the convex curvature provides for enhanced bending stiffness and allows for use of relatively thin panels. In embodiments, the panels 840 may be provided with corrugations and/or sharp bends (either along with the convex curvature or without) to increase bending stiffness and decrease required material thickness of the panels. The panels 840 may be spaced from one another to allow debris to drain from between the panels when, for example, the housing 824 is lifted off or otherwise shifts relative to the seafloor.

In embodiments, the brushes 860 may be strip brushes made of, for example, polypropylene or polyester bristles with plastic or stainless steel or aluminum backing/holders. The use of plastic bristles provided advantages, such as, for example, longevity, resistance to salt, low water absorption, and resistance to bio-growth, to name a few. The brushes 860 may be installed inside the housing 824 by, for example, inserting the brushes into holders and fixing the holders onto steel angle irons that are welded onto the inside of the housing 824. The number of brushes 860 arranged around the containment assembly may be in the range of, for example, one to eight, preferably four to eight, or more than eight. The higher number of brushes allows for every part of the containment to be brushed without necessarily rotating the containment in complete revolutions. This is particularly important in the winter when oyster growth has slowed and aggressive rotation of the containment should be avoided to prevent chipping shells at a time when oysters are hibernating and cannot repair. For example, the containment may be rotated back and forth by 360/8 degrees to ensure all surfaces are brushed and avoid tumbling of any oysters because oysters do not exceed their slip angle. With four strip brushes, the entire surface of the containment gets brushed at least four times with every revolution and may get brushed many more times than this given oscillating/ratcheting motion of the containment. In embodiments, the strip brushes can be configured and/or mounted to clean other surfaces, such as, for example, sprockets, chains, and wheel, to name a few. In embodiments, the brushes 860 are not necessarily intended to remove large marine growth but if the containment is rotated often enough then the brushes 860 will continuously remove larvae and other marine growth before it can take hold and grow to any appreciable size. This is important for maintaining open area of the outer enclosure and ensuring good water flow through the containment.

FIGS. 18A-18D illustrate components of an automated oyster maturation system in accordance with an exemplary embodiment of the present invention. As in previously-described embodiments, the system of the present embodiment may include a containment assembly 900 having an outer enclosure 970, which may have, for example, a cylindrical shape. Also, as in the previously described exemplary embodiments, containment assembly 900 may be made up of lengthwise sections 948A, 948B, 948C, 948D that may be joined together inside housing 924 by, for example, welding the angle rings and bulkheads on both sides of every section 948A, 948B, 948C, 948D to form channel rings to rest on rollers (not shown). In embodiments, methods other than welding may be used to join the sections 948A, 948B, 948C, 948D, such as, for example, bolt circle, torque couple friction or Oldham-style coupling, to name a few. Central shaft 940 may be divided between each section 948A, 948B, 948C, 948D and may mate together via, for example, male/female sockets and seals when the 948A, 948B, 948C, 948D are put together. In this regard, compression seals may be sandwiched between the sections when the sections are joined together. Each bulkhead may be made up of two angle rings and two plates which when joined together between each section 948A, 948B, 948C, 948D form a channel ring and a plate of full thickness.

As in the previously-described exemplary embodiments, the system includes an inlet assembly 960 that includes an injection hose 929 and pumps configured to inject seed oysters into the containment assembly 900, an outlet assembly 964 that includes an ejection hose 928 and pumps configured to transport harvest-ready oysters to, for example, collection vessels, and an ejection assembly 962 configured to eject harvest-ready oysters from the containment assembly 900. The ejection hose 928 and injection hose 929 may extend from a harvest hopper 927. Although the system in this exemplary embodiment includes only one inlet assembly 960, only one outlet assembly 964, only one ejection assembly 962, and only one hopper 927, it should be appreciated that the system may include more than one of each of these components, as disclosed in relation to previously-described exemplary embodiments.

In embodiments, the hopper 927 receives harvest-ready oysters ejected from the ejection assembly 962. As in previously-described embodiments, harvest-ready oysters may be ejected from an inner-most compartment of the containment assembly 900 by one or more screw flights 918 into the hopper 927.

In embodiments, the housing 924 may be provided with legs 950, as described previously.

Figure 18A:
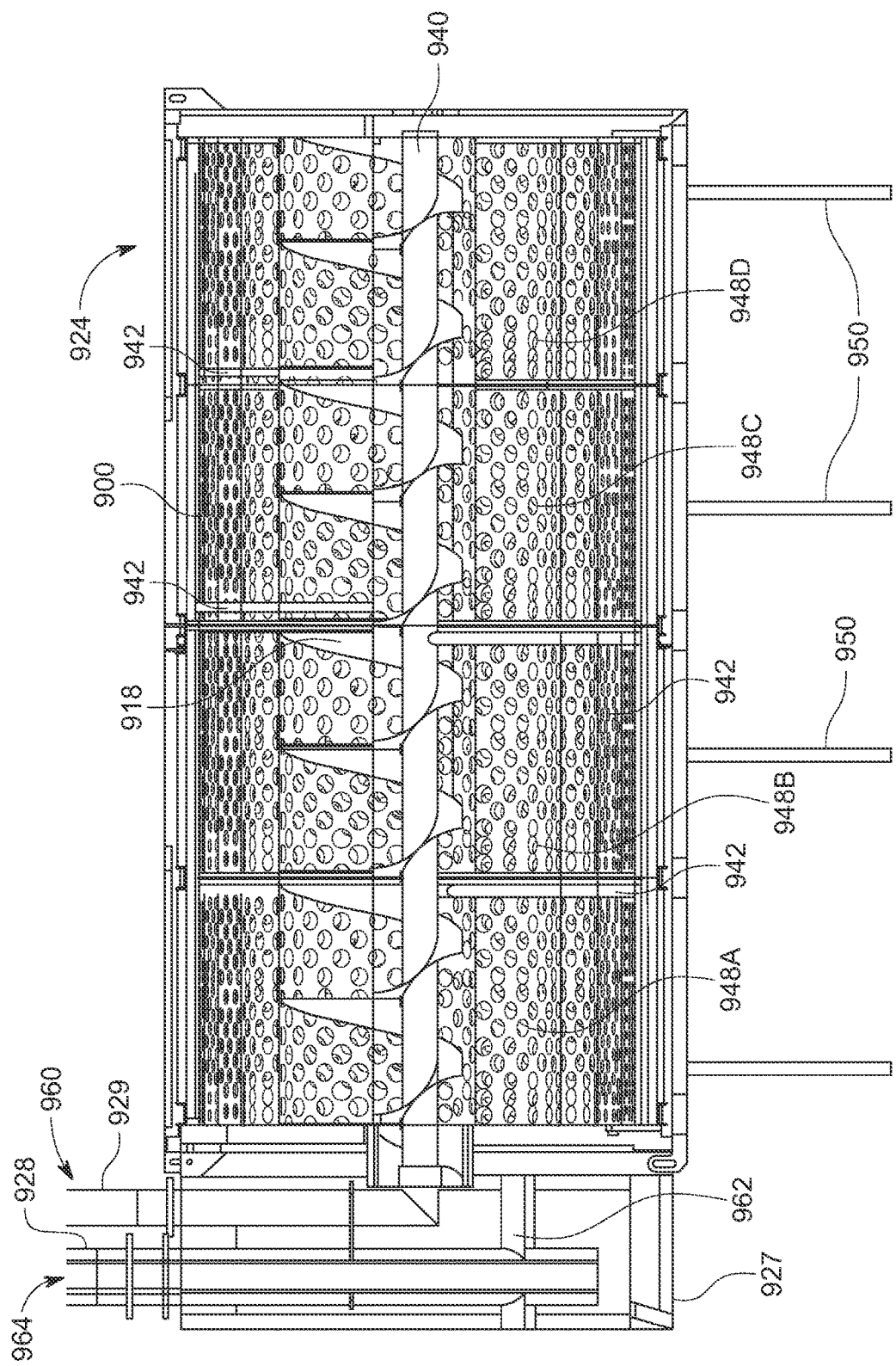
FIGS. 18A-18D illustrate components of an automated oyster maturation system in accordance with an exemplary embodiment of the present invention.
Figure 18B:
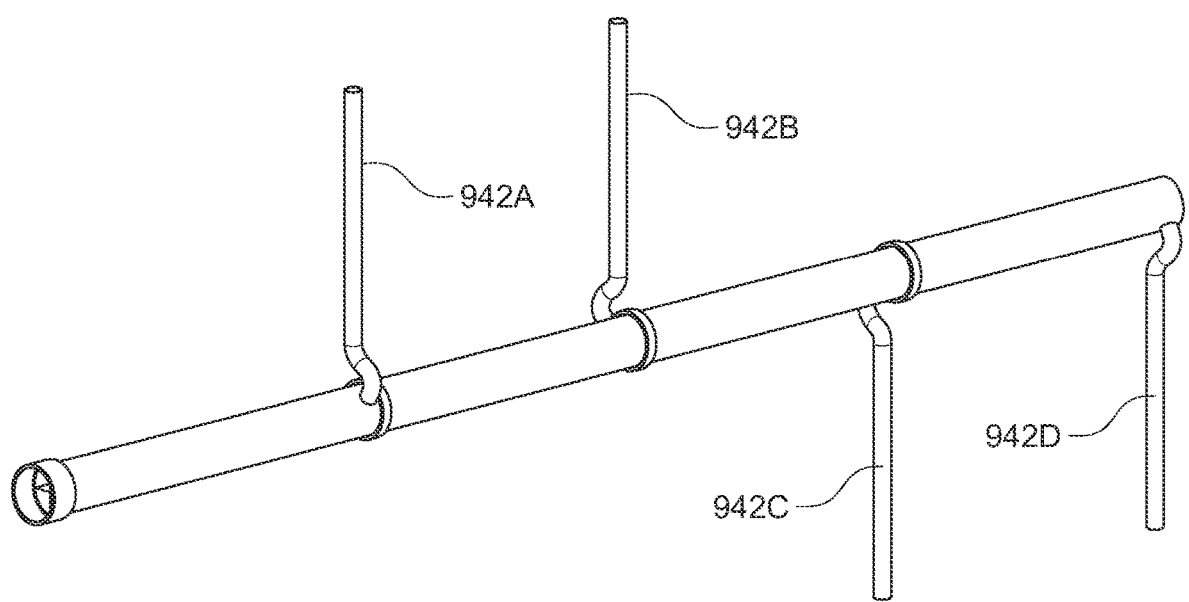
Figure 18C:
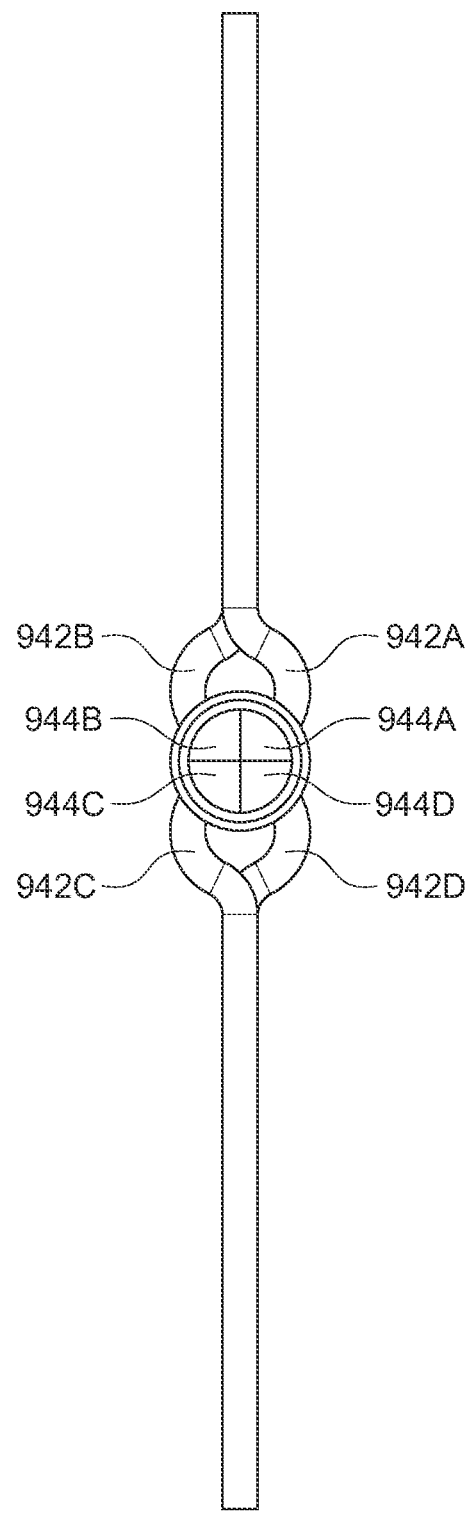
Figure 18D:
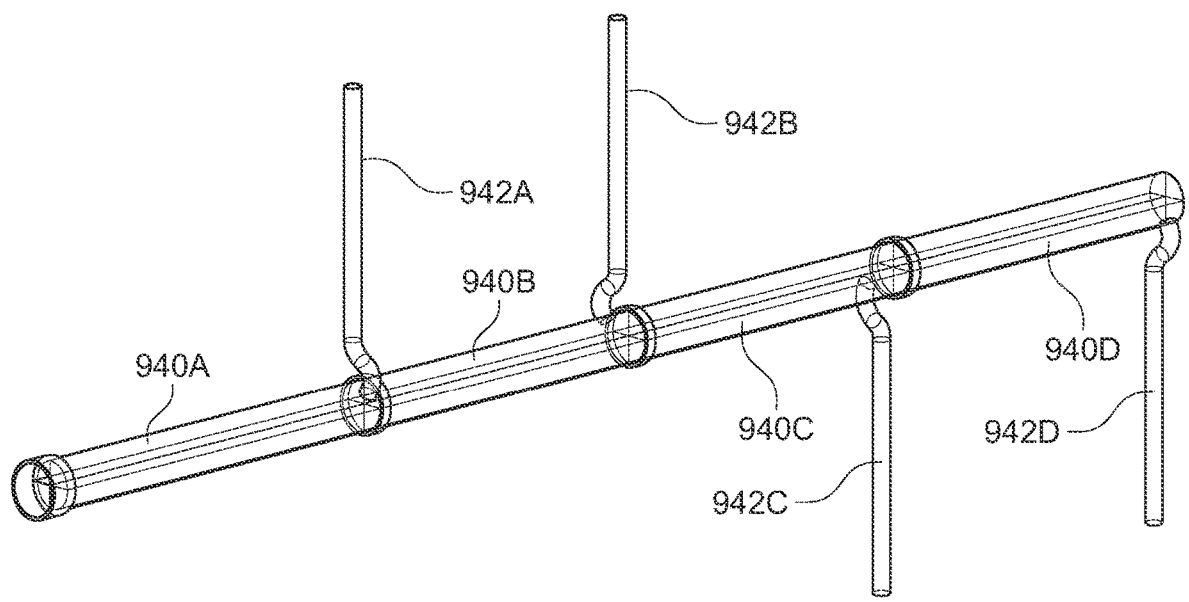
Figure 19A:
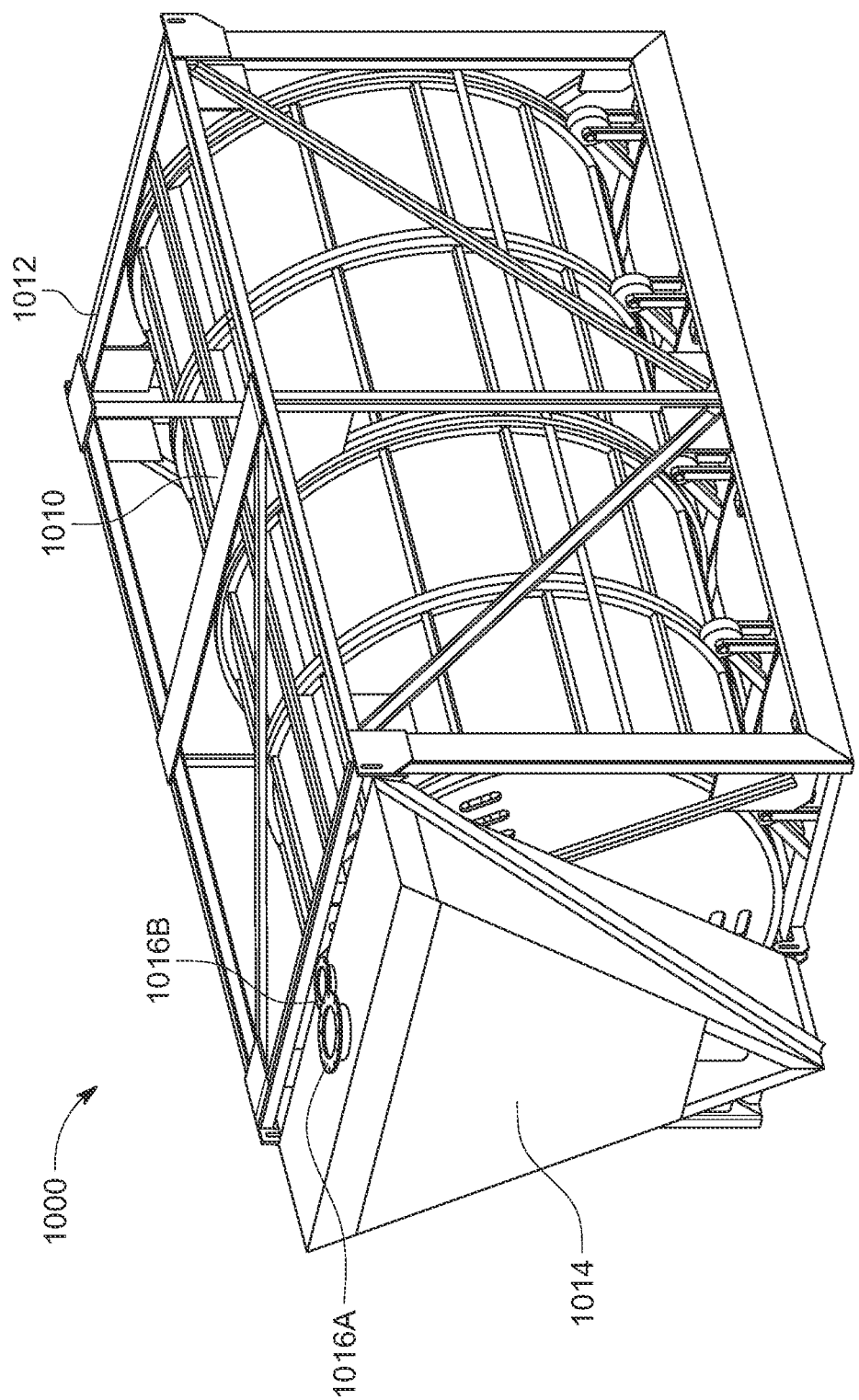
FIG. 19A provides a perspective view of an automated oyster maturation system in accordance with an exemplary embodiment of the present invention.
Figure 19B:
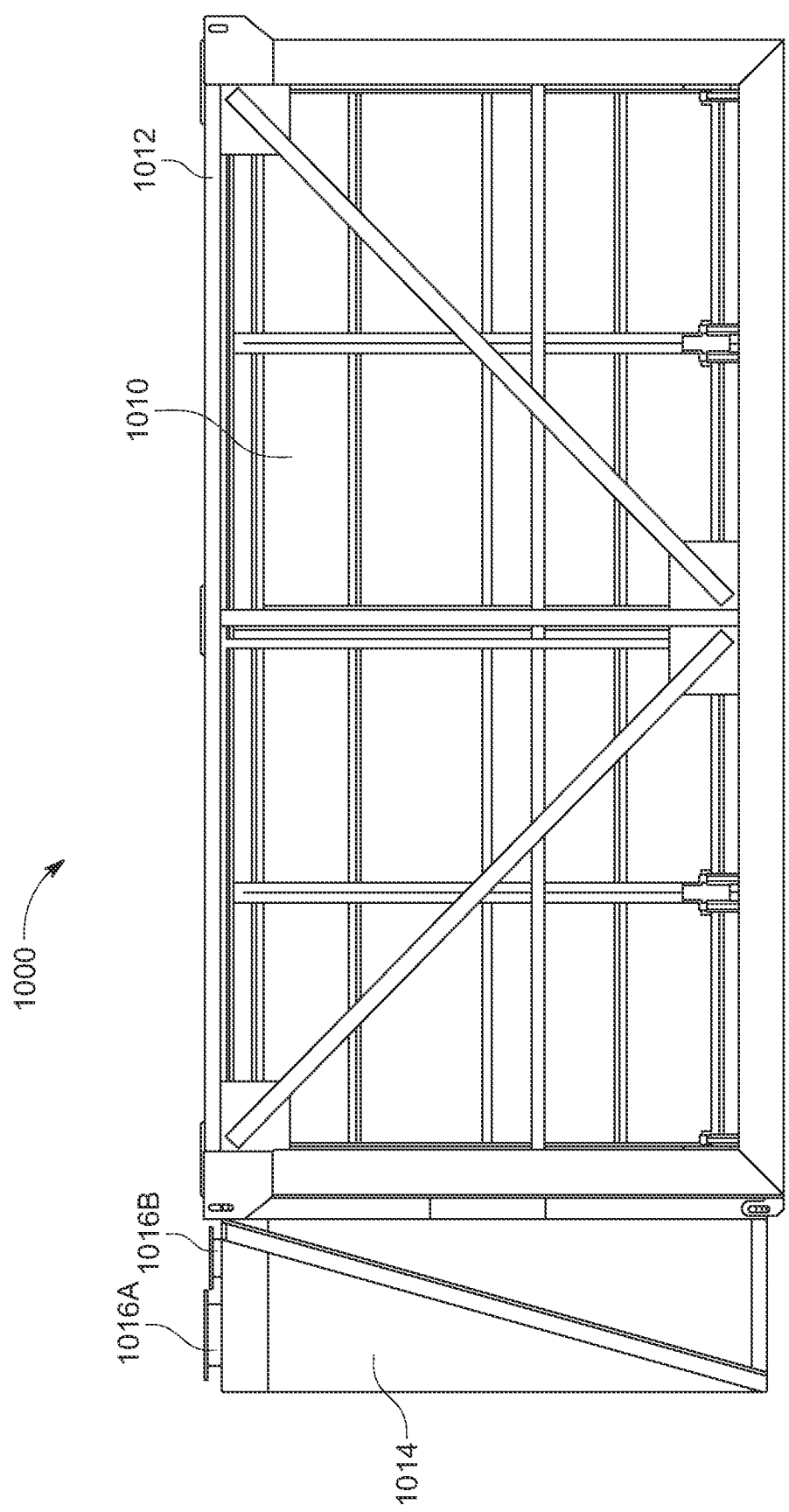
FIG. 19B provides a side view of the automated oyster maturation system of FIG. 19A.
Figure 19C:
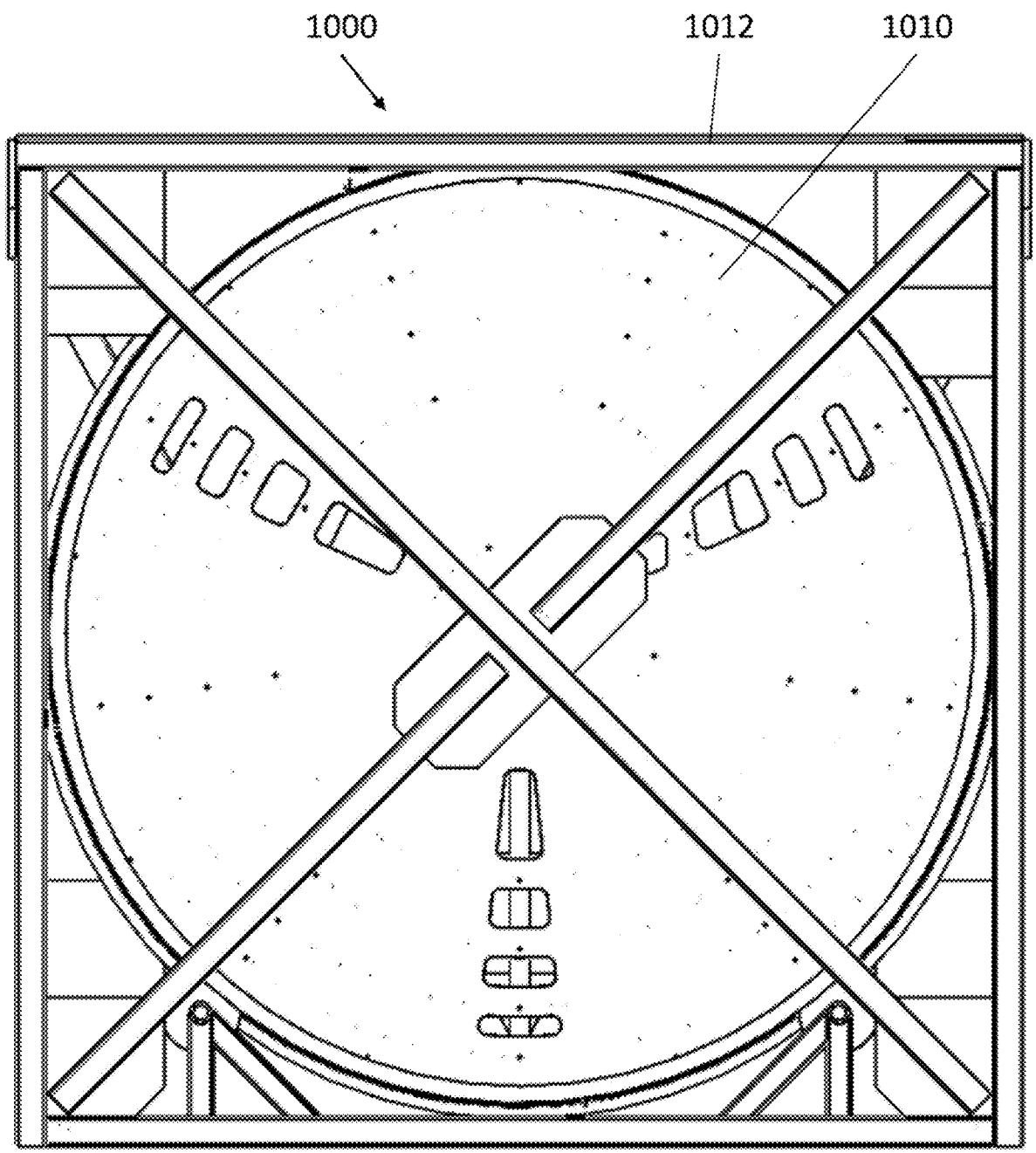
FIG. 19C provides a first end view of the automated oyster maturation system of FIG. 19A.
Figure 19D:
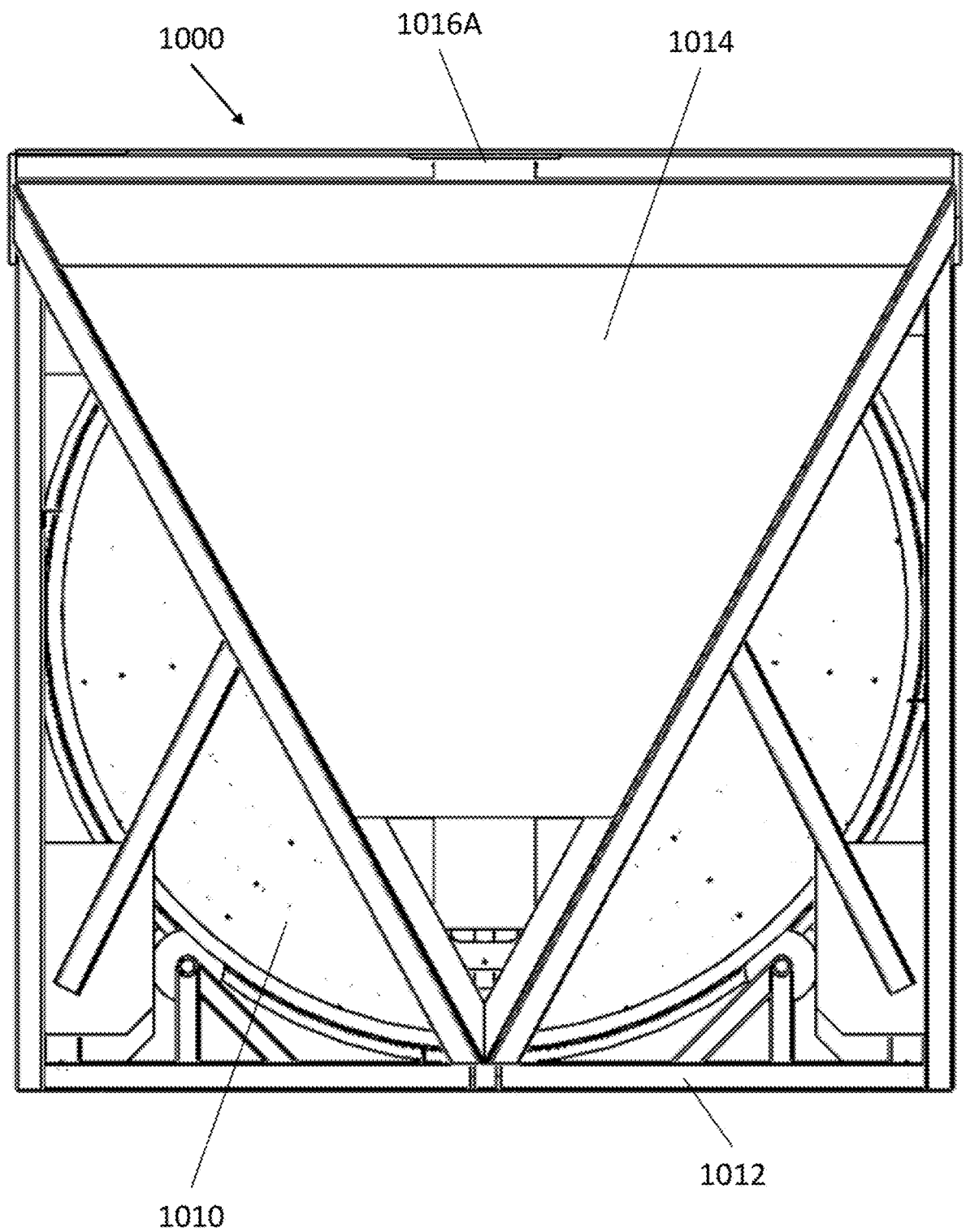
FIG. 19D provides a second end view of the automated oyster maturation system of FIG. 19A.
Figure 19E:
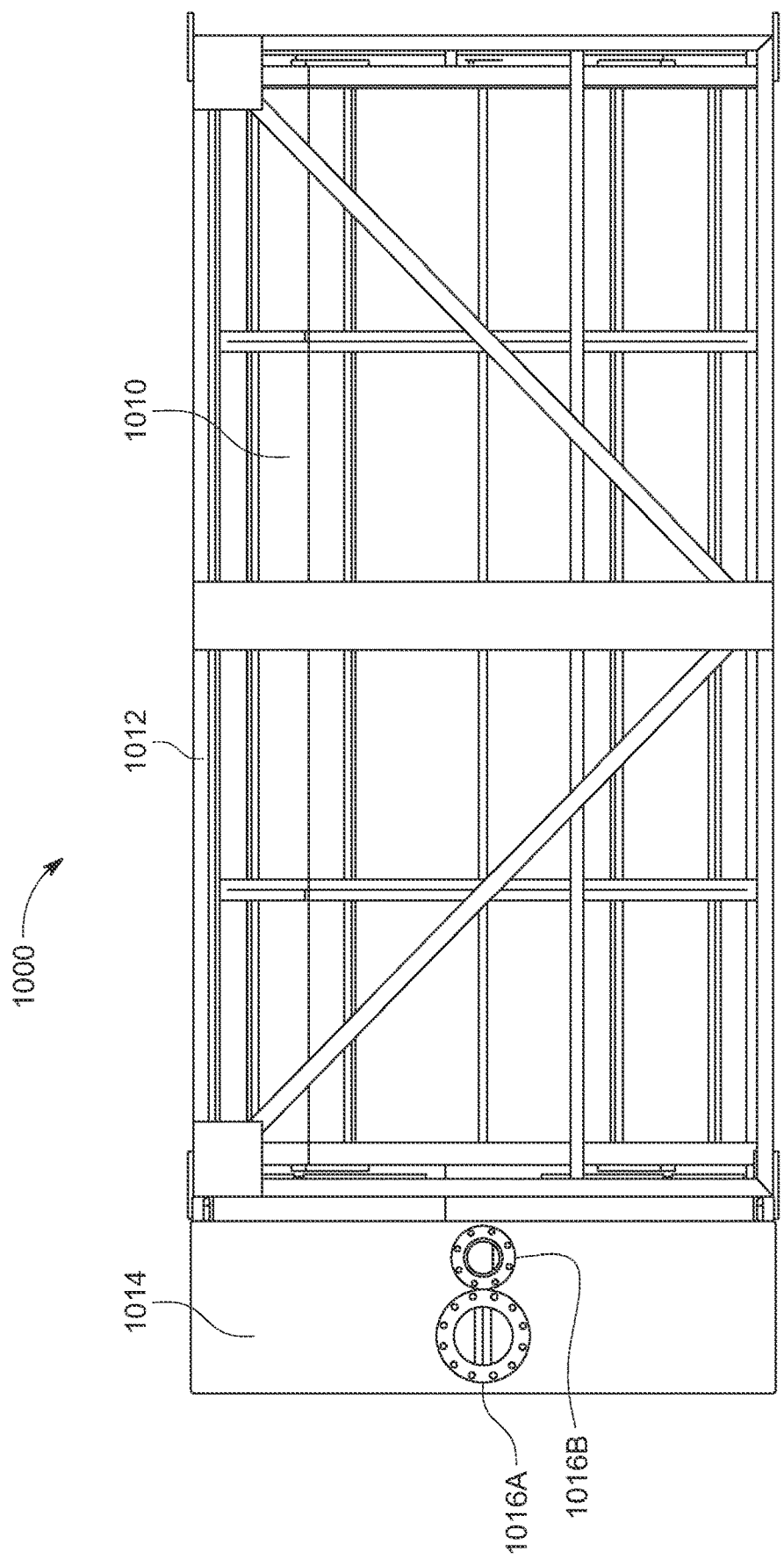
FIG. 19E provides a top view of the automated oyster maturation system of FIG. 19A.
Figure 19F:
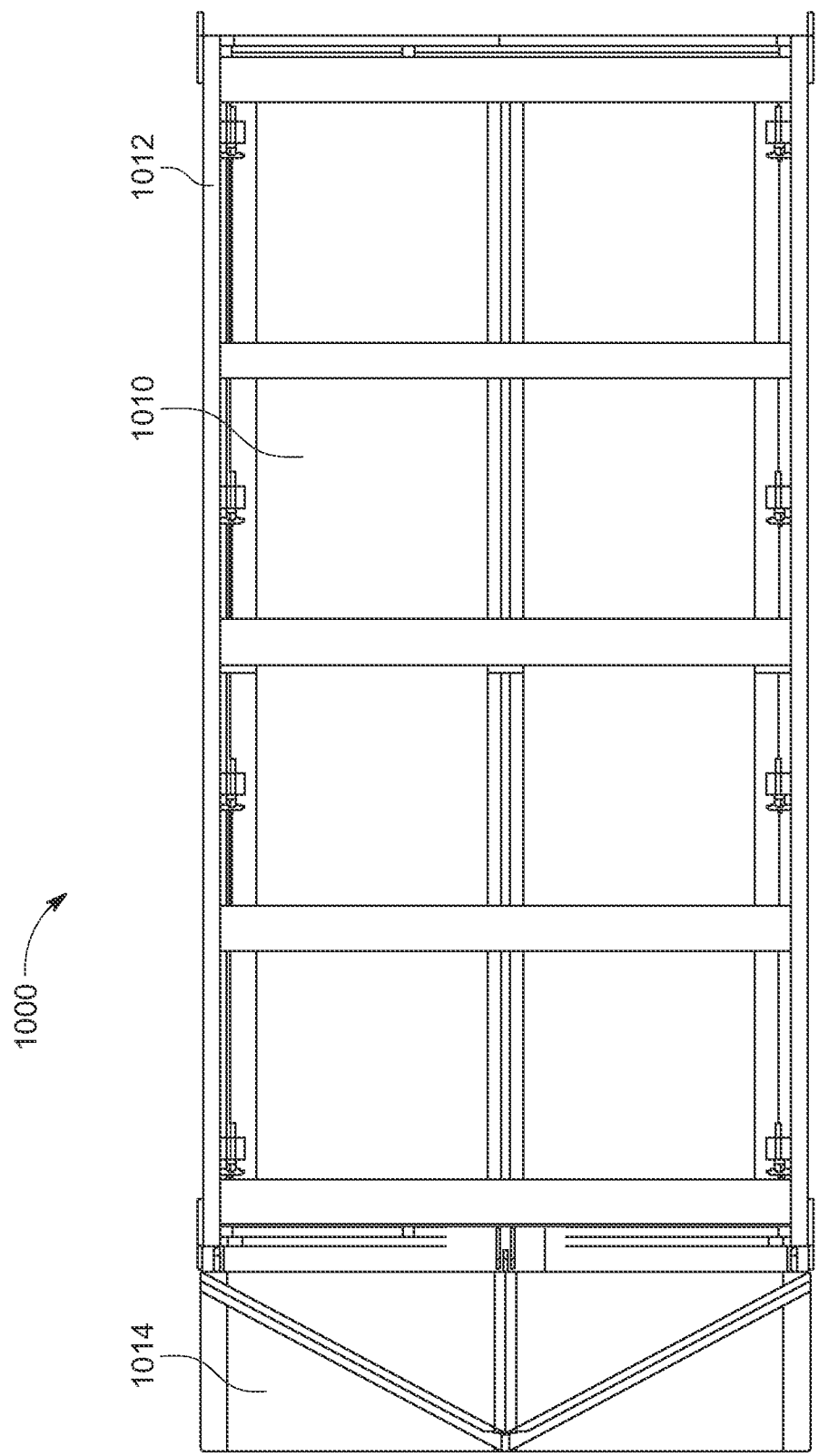
FIG. 19F provides a bottom view of the automated oyster maturation system of FIG. 19A.

As shown in FIG. 18D, in embodiments, the central shaft 940 may be divided into lengthwise sections 940A, 940B, 940C, 940D, each corresponding to a respective lengthwise section 948A, 948B, 948C, 948D of the containment assembly 900. As shown in FIG. 18C, the cross section of each lengthwise section 940A, 940B, 940C, 940D may be divided into a number of pie-shaped compartments 944A, 944B, 944C, 944D, with the number of compartments having a direct relationship to the number of lengthwise sections. For example, in the illustrated embodiments, the central shaft 940 includes four lengthwise sections, in which case the cross-section of each lengthwise section is divided into four equal pie-shaped compartments. It should be appreciated that the number of lengthwise sections and cross-sectional compartments is not limited to any particular number, and in embodiments the number may vary from, for example, two to ten.

In embodiments, one or more of each compartment 944A, 944B, 944C, 944D in each lengthwise section 940A, 940B, 940C, 940D is blocked off. For example, each compartment 944A, 944B, 944C, 944D is blocked off at one point along the corresponding one of the lengthwise sections 940A, 940B, 940C, 940D, where the one point may be, for example, between the ends points of the corresponding one of the lengthwise sections 940A, 940B, 940C, 940D or at the end point of the corresponding one of the lengthwise sections 940A, 940B, 940C, 940D. More specifically, compartment 944A is blocked off within lengthwise section 940A, compartment 944B is blocked off within lengthwise section 940B, compartment 944C is blocked off within lengthwise section 940C, and compartment 944D is blocked off within lengthwise section 940D. It should be appreciated that only one of the compartments (compartment 944A) in the first length-wise section 940A is blocked off within the lengthwise section 940A, while the last length-wise section 940E has all compartments blocked off at the end of the lengthwise section 940E. With this configuration, the cross-section of the entire central shaft 940 may be seen as being made up of pie-shaped compartments, with each pie-shaped compartment extending along the length of the central shaft 940 but blocked off within a respective lengthwise section of the central shaft 940.

In embodiments, each lengthwise section 940A, 940B, 940C, 940D includes corresponding one or more distribution pipes extending radially from the lengthwise section. The entry, friction, and exit losses of these distribution pipes contributes to increased pressure loss compared to just distributed holes along the length of central shaft as in previous embodiments. This helps further improve even seed distribution. The distribution pipes also ensure the seed is directly delivered to the outermost layer and is not damaged by falling through all layers as may occur in previous embodiments.

Specifically, in the embodiment shown in FIG. 18B, lengthwise section 940A includes distribution pipe 942A, lengthwise section 940B includes distribution pipe 942B, lengthwise section 940C includes distribution pipe 942C, and lengthwise section 940D includes distribution pipe 942D. Each set of distribution pipes is in fluid communication with the compartment within the respective lengthwise section that is blocked off within the respective lengthwise section at a point before that compartment is blocked off. For example, the distribution pipe 942C is in fluid communication with compartment 944C of lengthwise section 940C at a point before the compartment 944C is blocked off.

Although only one distribution pipe is included within each lengthwise section in the embodiments illustrated in FIG. 18B, it should be appreciated that the number of distribution pipes within each lengthwise section is not limited to one, and in other embodiments each length-wise section may include, for example, two, three, four, five or six distribution pipes, to name a few.

In embodiments, the distribution pipes 942A, 942B, 942C, 942D are made of flexible and/or formable material, such as, for example, rubber, plastic, or aluminum, to name a few. In embodiments, as shown in FIGS. 18B, 18C, 18D the distribution pipes 942A, 942B, 942C, 942D exit central shaft 940 at different angles but are routed so their axes are co-planar and pass through perforated sheets at the intersections between walls and ramps of the containment assembly 900. Distribution pipes are preferably routed in one of two opposite directions so that during seed injection, the containment can be rotated (e.g., according to encoder readings) such that the openings of the distribution pipes are oriented in the horizontal direction and injected seed tumbles to the bottom of the outside layer and does not block the outlet of the distribution pipes.

In operation, seed flow is divided equally among the compartments 944A, 944B, 944C, 944D at the beginning of the first lengthwise section 940A where flow velocity is the highest and seeds are well-mixed due to turbulence and fully entrained in flow, such that seed settling along the length of the central shaft 940 will not affect seed distribution. As the seed flow progresses through the central shaft 940, the cross-sectional area is progressively reduced due to the blocked off compartments, thereby ensuring that the velocity within the central shaft 940 remains at a sufficient level to further minimize the effect of seed settling along the length of the central shaft 940. In embodiments, the diameter of the central pipe is substantially larger than that In embodiments, the hopper may have angled walls, which provides advantages, such as, for example, simpler manufacturing and minimizing oyster/wall friction to ensure mass flow and complete emptying of the hopper every time. For example, as shown in FIG. 16A, the hopper 727 has the shape of a pure triangular prism with the walls angled from the top corners of the frame all the way to the bottom-center. Providing the hopper 727 with a triangular profile rather than a profile with vertical portions maximizes steepness of the walls. In embodiments, the walls may be angled as such at an angle of 60 degrees or greater to minimize wall friction and risk of bridging.

In embodiments, the hopper may be hung off the end of the frame using, for example, pins and/or screws such that it can be quickly installed and also removed and brought to the surface for harvesting or servicing.

FIGS. 19A-19F illustrate an automated oyster maturation system, generally designated by reference number 1000, according to an exemplary embodiment of the present invention. The system 1000 does not include external components, such as, for example, an inlet assembly, an outlet assembly, legs or other support structures, tethers and a floating platform, to name a few. Instead, the system 1000 is this embodiment may only include specific components, such as, for example, a containment assembly 1010 rotatably mounted within a housing 1012, and a hopper 1014 attached to the housing 1012, to name a few. The hopper 1014 may include fittings 1016A, 1016B configured to allow for installation of the inlet and outlet assemblies. The system 1000 in accordance with this exemplary embodiment may be intended as a deliverable to a customer, so that, for example, the system 1000 may be installed by the customer (or technician) at a selected site by attaching external components as needed. In embodiments, the system 1000 may be delivered as a kit with separate external components, such as, for example, legs, inlet and outlet assemblies, tethers, cables and floating platform, to name a few, that can later be installed at the site.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed is:

1. An automated oyster maturation system comprising:
    (A) a housing;
    (B) a containment assembly rotatably disposed within the housing, the containment assembly comprising:
        (1) an outer cylindrical enclosure;
        (2) one or more sheets of material contained within the outer cylindrical enclosure arranged to form a spiral construction having an outer diameter and an inner diameter, wherein the spiral construction comprises at least three turns, and the spiral construction further comprises:
            (i) a plurality of compartments that are in communication with one another;
            (ii) a plurality of walls that define the plurality of compartments;
            (iii) a plurality of ramps, wherein each of the plurality of ramps is attached to a corresponding wall of the plurality of walls so as to form a plurality of pairs of walls and ramps that provide the spiral construction with a spiral shape;
            (iv) a plurality of openings disposed in the plurality of walls and the plurality of ramps, the plurality of openings comprising a plurality of sets of openings with the openings within each set having diameters of a common size, the common size increasing from the outer diameter to the inner diameter of the spiral construction so that, with every complete rotation of the containment assembly, each oyster will tumble further into the spiral construction and ascend from the oyster's original compartment into an adjacent inner compartment where opening size is larger than in the original compartment such that only oysters which have grown sufficiently remain in the adjacent inner compartment while oysters that have not grown sufficiently yet will fall through the openings of the adjacent inner compartment into the original compartment;
        (3) a hollow shaft having a first end and a second end disposed within an innermost one of the plurality of compartments, wherein the first end of the hollow shaft is configured to receive seed-oysters and wherein the hollow shaft includes a plurality of holes formed in a wall of the hollow shaft between the first end and the second end and sized to allow seed-oysters to pass therethrough;
    (C) an inlet assembly configured to feed seed oysters into the containment assembly, wherein the inlet assembly is operatively connected to the hollow shaft; and
    (D) an ejection assembly configured to eject harvest-ready oysters from the innermost compartment of the plurality of compartments.

2. The automated oyster maturation system of claim 1, wherein the housing is a frame that supports the containment assembly.

3. The automated oyster maturation system of claim 1, wherein the housing is a shipping container which supports and substantially encapsulates the containment assembly.

4. The automated oyster maturation system of claim 1, wherein the oyster maturation system further comprises at least one rotational device disposed within the housing and configured to rotate the containment assembly within the housing.

5. The automated oyster maturation system of claim 4, wherein the at least one rotational device comprises a motor.

6. The automated oyster maturation system of claim 5, wherein the housing comprises rollers upon which the containment assembly rests.

7. The automated oyster maturation system of claim 6, wherein the rollers are driven by the motor.

8. The automated oyster maturation system of claim 4, wherein the at least one rotational device is configured to rotate the containment assembly about a central axis.

9. The automated oyster maturation system of claim 4, wherein the at least one rotational device is configured to rotate the containment assembly periodically.

10. The automated oyster maturation system of claim 4, wherein the at least one rotational device is configured to rotate the containment assembly aperiodically.

11. The automated oyster maturation system of claim 4, wherein the at least one rotational device is further configured to dither the containment assembly within the housing.

12. The automated oyster maturation system of claim 1, wherein the oyster maturation system further comprises a pitch device disposed within the housing and configured to agitate the containment assembly so as to cause oysters within the cylindrical assembly to shift positions.

13. The automated oyster maturation system of claim 1, wherein the spiral construction comprises at least four turns.

14. The automated oyster maturation system of claim 1, wherein the plurality of compartments are in fluidic communication with one another.

15. The automated oyster maturation system of claim 1, wherein the innermost one of the plurality of compartments is configured to hold harvest-ready oysters.

16. The automated oyster maturation system of claim 15, wherein an outermost one of the plurality of compartments is configured to hold seed oysters.

17. The automated oyster maturation system of claim 16, wherein compartments in between the outermost one of the plurality of compartments and the innermost one of the plurality of compartments are configured to hold oysters of increasing sizes, from a size of growth larger than seed-oysters to a size of growth smaller than harvest-ready oysters.

18. The automated oyster maturation system of claim 1, further comprising a hopper that receives harvest-ready oysters ejected from the ejection assembly.

19. The automated oyster maturation system of claim 1, further comprising distribution pipes extending from the hollow shaft.

20. The automated oyster maturation system of claim 19, wherein the hollow shaft is divided into a plurality of compartments that extend along a length of the hollow shaft.

21. The automated oyster system of claim 20, wherein the hollow shaft comprises a plurality of lengthwise sections, and each of the plurality of compartments is blocked off within a respective one of the plurality of lengthwise sections, with a number of blocked off compartments increasing along the length of the hollow shaft.

22. The automated oyster system of claim 21, wherein the distribution pipes comprise a plurality of distribution pipes, and one or more of the plurality of distribution pipes correspond to a respective one of the plurality of lengthwise sections of the hollow shaft.

23. A method of maturing oysters comprising:
   (A) injecting seed-oysters into a containment assembly that is rotatably disposed within a housing, the containment assembly comprising:
      (1) an outer cylindrical enclosure;
      (2) one or more sheets of material contained within the outer cylindrical enclosure and arranged to form a spiral construction having an outer diameter and an inner diameter, wherein the spiral construction comprises at least three turns, and the spiral construction further comprises:
         (i) a plurality of compartments that are in communication with one another;
         (ii) a plurality of walls that define the plurality of compartments;
         (iii) a plurality of ramps, wherein each of the plurality of ramps is attached to a corresponding wall of the plurality of walls so as to form a plurality of pairs of walls and ramps that provide the spiral construction with a spiral shape;
         (iv) a plurality of openings disposed in the plurality of walls and the plurality of ramps, the plurality of openings comprising a plurality of sets of openings with the openings within each set having diameters of a common size, the common size increasing from the outer diameter to the inner diameter of the spiral construction; and
   (B) rotating the containment assembly so that, with every complete rotation of the containment assembly, each oyster will tumble further into the spiral construction and ascend from the oyster's original compartment into an adjacent inner compartment where the opening size is larger than in the original compartment such that only oysters which have grown sufficiently remain in the adjacent inner compartment while oysters that have not grown sufficiently yet will fall through the openings of the adjacent inner compartment into the original compartment.

24. The method of claim 23, wherein the step (A) of injecting the seed-oysters comprises injecting the seed-oysters into a hollow shaft disposed within an innermost one of the plurality of compartments, wherein the hollow shaft comprises a plurality of holes formed in a wall of the hollow shaft and sized to allow seed-oysters to pass therethrough.

25. The method of claim 24, wherein the step (A) of injecting the seed-oysters comprises injecting the seed-oysters via an inlet assembly operatively connected to the hollow shaft.

26. The method of claim 23, further comprising the step of ejecting harvest-ready oysters from the containment assembly from an innermost compartment of the plurality of compartments via an ejection assembly.

\* \* \* \* \*